US010493141B2

(12) United States Patent
Stapleton et al.

(10) Patent No.: US 10,493,141 B2
(45) Date of Patent: Dec. 3, 2019

(54) VIRAL RNA SEGMENTS AS IMMUNOMODULATORY AGENTS AND VACCINE COMPONENTS

(71) Applicant: THE UNIVERSITY OF IOWA RESEARCH FOUNDATION, Iowa City, IA (US)

(72) Inventors: Jack T. Stapleton, Iowa City, IA (US); Nirjal Bhattarai, Coralville, IA (US); James McLinden, Coralville, IA (US); Jinhau Xiang, Iowa City, IA (US); Bev Davidson, Philadelphia, PA (US)

(73) Assignee: THE UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 15/510,315

(22) PCT Filed: Sep. 9, 2015

(86) PCT No.: PCT/US2015/049167
§ 371 (c)(1),
(2) Date: Mar. 10, 2017

(87) PCT Pub. No.: WO2016/044023
PCT Pub. Date: Mar. 24, 2016

(65) Prior Publication Data

US 2018/0000925 A1 Jan. 4, 2018

Related U.S. Application Data

(60) Provisional application No. 62/051,727, filed on Sep. 17, 2014.

(51) Int. Cl.

| | |
|---|---|
| ***A61K 39/00*** | (2006.01) |
| ***A61K 39/395*** | (2006.01) |
| ***A61K 48/00*** | (2006.01) |
| ***C07H 21/02*** | (2006.01) |
| ***C07H 21/04*** | (2006.01) |
| ***A61K 39/12*** | (2006.01) |
| ***C12N 15/117*** | (2010.01) |
| ***C07K 14/08*** | (2006.01) |
| ***C07K 14/18*** | (2006.01) |
| ***C07K 14/47*** | (2006.01) |
| ***C12N 7/04*** | (2006.01) |

(52) U.S. Cl.
CPC .............. *A61K 39/12* (2013.01); *C07K 14/08* (2013.01); *C07K 14/1833* (2013.01); *C07K 14/473* (2013.01); *C12N 7/04* (2013.01); *C12N 15/117* (2013.01); *C12N 2310/17* (2013.01); *C12N 2330/50* (2013.01); *C12N 2760/18711* (2013.01); *C12N 2770/24111* (2013.01); *C12N 2770/24211* (2013.01)

(58) Field of Classification Search
CPC .............. A61K 2300/00; A61K 39/395; A61K 39/39558; A61K 2039/505; A61K 47/48238
See application file for complete search history.

(56) References Cited

U.S. PATENT DOCUMENTS

| | | | |
|---|---|---|---|
| 2005/0266400 A1 | 12/2005 | Dumonceaux et al. | |
| 2010/0179309 A1 * | 7/2010 | Manoharan ........... | C12N 15/111 536/24.5 |
| 2015/0071955 A1 | 3/2015 | Stapleton et al. | |
| 2016/0067331 A1 | 3/2016 | Stapleton et al. | |

FOREIGN PATENT DOCUMENTS

| | | | |
|---|---|---|---|
| CN | 102206256 | | 10/2011 |
| WO | WO 2001/077157 | | 10/2001 |
| WO | WO 2003/051912 | | 6/2003 |
| WO | WO 2004/037202 | | 5/2004 |
| WO | WO 2004/108159 | | 12/2004 |
| WO | WO 2009/120306 | | 10/2009 |
| WO | WO 2013/142167 | | 9/2013 |
| WO | WO213142167 | * | 9/2013 |
| WO | WO2013142167 | * | 9/2013 |

OTHER PUBLICATIONS

Phipps et al., "An octapeptide analogue of HIV gp120 modulates protein tyrosine kinase activity in activated peripheral blood T lymphocytes", Clin Exp Immunol, 1995, 100:412-418.*
Office Communication issued in Singaporean Patent Application No. 11201702116V, dated Apr. 17, 2018.
Petrovic et al., "Hepatitis C virus targets the T cell secretory machinery as a mechanism of immune evasion," *Hepatology*, 53(6):1846-1853, 2011.
Chang et al., "Japanese encephalitis virus non-coding RNA inhibits activation of interferon by blocking nuclear translocation of interferon regulatory factor 3" *Veterinary Microbiology*, 166(1-2):11-21, 2013.
Guo et al., "Alternative capture of noncoding RNAs or protein-coding genes by herpesviruses to alter host T cell function," *Molecular Cell*, 54(1):67-79, 2014.
Stapleton et al., "A novel T cell evasion mechanism in persistent RNA virus infection," *Transactions of the American Clinical and Climatological Association*, 125:14-24, 2014.
Supplementary Partial European Search Report issued in European Application No. 15842717.9, dated Feb. 12, 2018.
Berzsenyi et al., "Down-regulation of intra-hepatic T-cell signaling associated with GB virus C in a HCV/HIV co-infected group with reduced liver disease," *J. Hepatol.*, 5(3):536-544, 2011.

(Continued)

*Primary Examiner* — Barry A Chestnut
(74) *Attorney, Agent, or Firm* — Parker Highlander PLLC

(57) ABSTRACT

The disclosure provides compositions and methods involving viral RNA segments for use in modulating immune responses, including inhibition inflammation related to pathogenic T-cell activation. In addition, modification of the viral sequences responsible for modulating immune response provides for improved vaccine formulations.

20 Claims, 27 Drawing Sheets

Specification includes a Sequence Listing.

(56) References Cited

OTHER PUBLICATIONS

Bhattarai and Stapleton, “GB virus C: the good boy virus?” *Trends Microbiol.*, 20(3):124-130, 2012.
Bhattarai et al., “Conserved Motifs within Hepatitis C Virus Envelope (E2) RNA and Protein Independently Inhibit T Cell Activation,” *PLoS Pathogens*, 1(9):e1005183, DOI:10.1371/journal.ppat.1005183, pp. 1-23, 2015.
Bhattarai et al., “GB virus C envelope protein E2 inhibits TCR-induced IL-2 production and alters IL-2-signaling pathways,” *J. Immunol.*, 189(5):2211-2216, 2012.
Bhattarai et al., “GB virus C particles inhibit T cell activation via envelope E2 protein-mediated inhibition of TCR signaling,” *J. Immunol.*, 190(12):6351-6359, 2013.
Bhattarai et al., “GB virus C viremia is associated with higher levels of double-negative T cells and lower T-cell activation in HIV-infected individuals receiving antiretroviral therapy,” *J. Infect. Dis.*, 206(9):1469-1472, 2012.
Bhattarai et al., “Hepatitis C virus infection inhibits a Src-kinase regulatory phosphatase and reduces T cell activation in vivo,” *PloS Pathogens*, 13(2): e1006232, doi:10.1371/journal.ppat.1006232, pp. 1-20, 2017.
Maidana-Giret et al., “GB virus type C infection modulates T-cell activation independently of HIV-1 viral load,”*AIDS*, 23(17):2277-2287, 2009.
Nattermann et al., “Regulation of CC chemokine receptor 5 in hepatitis G virus infection,”*AIDS*, 17(10):1457-1462, 2003.
PCT International International Search Report and Written Opinion issued in International Application No. PCT/US2015/049167, dated Feb. 2, 2016.
PCT International Invitation to Pay Additional Fees issued in International Application No. PCT/US2015/049167, dated Nov. 20, 2015.
Phipps et al., “An octapeptide analogue of HIV gp120 modulates tyrosine kinase activity in activated peripheral blood T lymphocytes,” *Clin. Exp. Immunol.*, 100(3):412-418, 1995.
Rydze et al., “GB virus C infection is associated with a reduced rate of reactivation of latent HIV and protection against activation-induced T-cell death,” *Antivir. Ther.*, 17(7):1271-1279, 2012.
Schwarze-Zander et al., “GB virus C coinfection in advanced HIV type-1 disease is associated with low CCRS and CXCR4 surface expression on CD4(+) T-cells,”*Antivir. Ther.*, 15(5):745-752, 2010.
Stapleton et al., “GB virus C infection is associated with altered lymphocyte subset distribution and reduced T cell activation and proliferation in HIV-infected individuals,” *PLoS One* 7(11):e50563, 2012.
Stapleton et al., “GBV-C viremia is associated with reduced CD4 expansion in HIV-infected people receiving Haart and interleukin-2 therapy,”*AIDS*, 23(5):605-610, 2009.
Stapleton et al., “The GB viruses: a review and proposed classification of GBV-A, GBV-C (HGV), and GBV-D in genus Pegivirus within the family Flaviviridae,” *J. Gen. Virol.*, 92(Pt. 2):233-246, 2011.

* cited by examiner

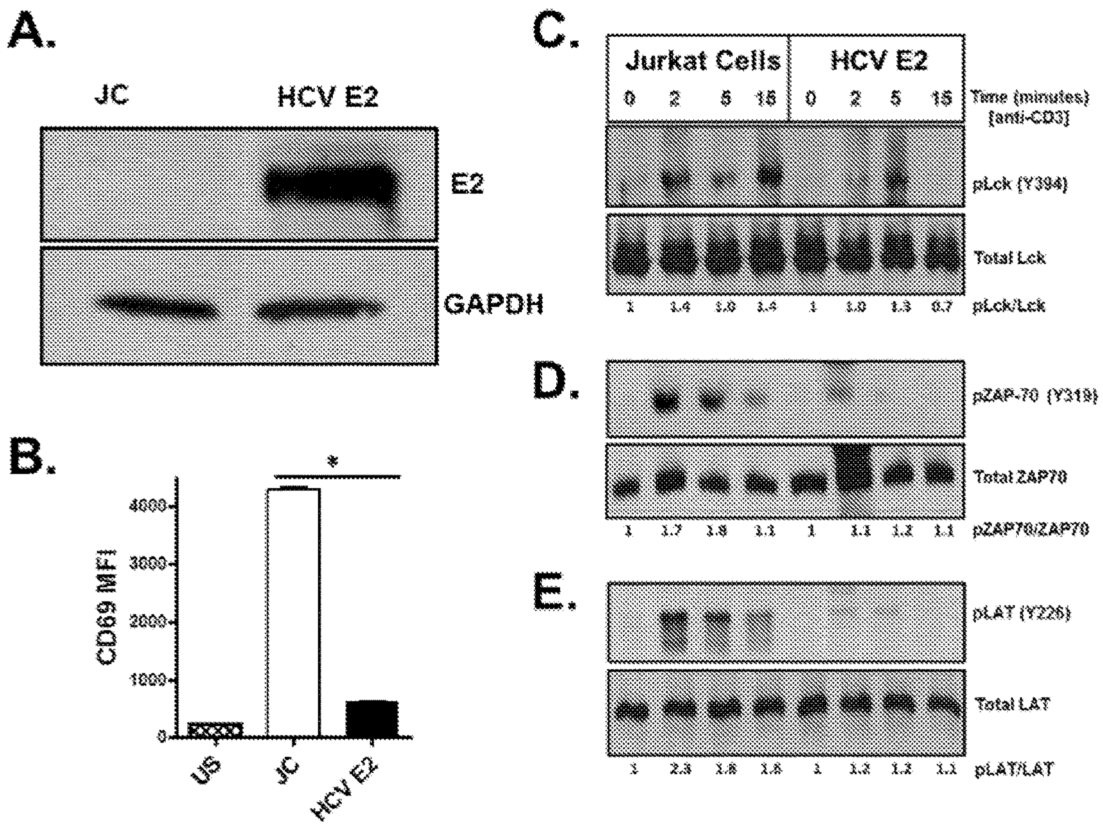
FIGS. 12A-E

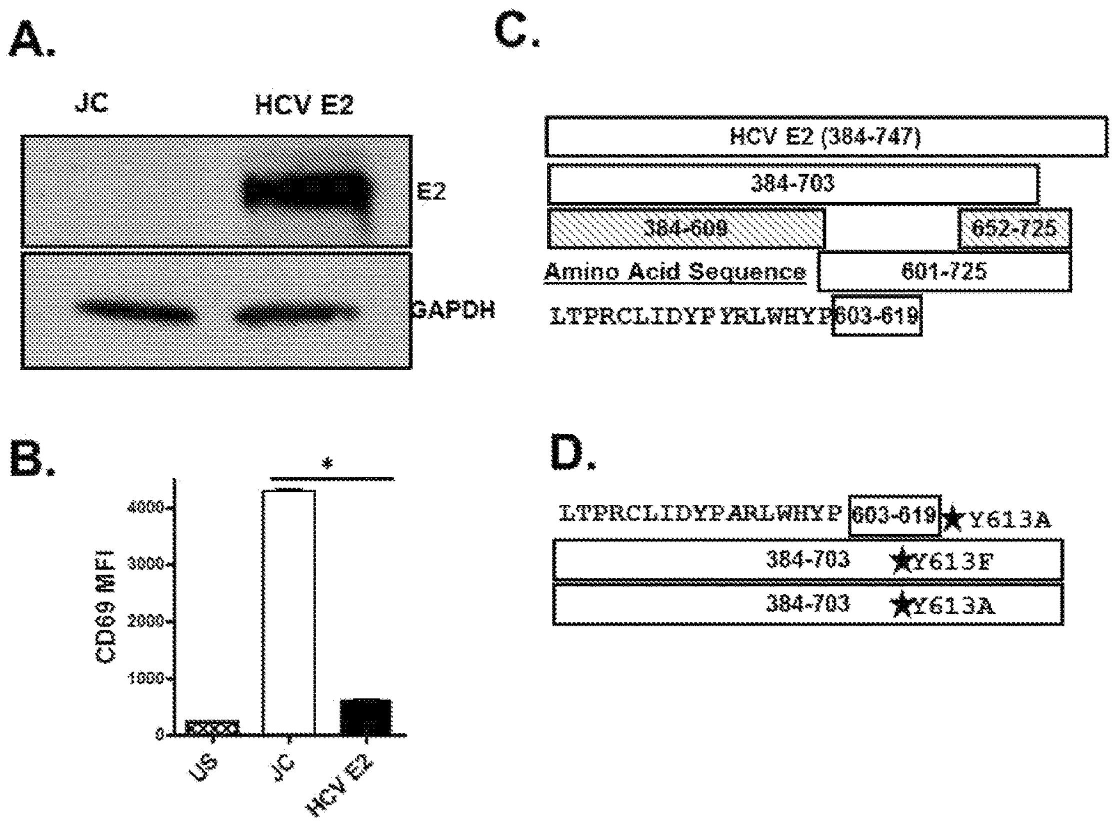
FIGS. 13A-D

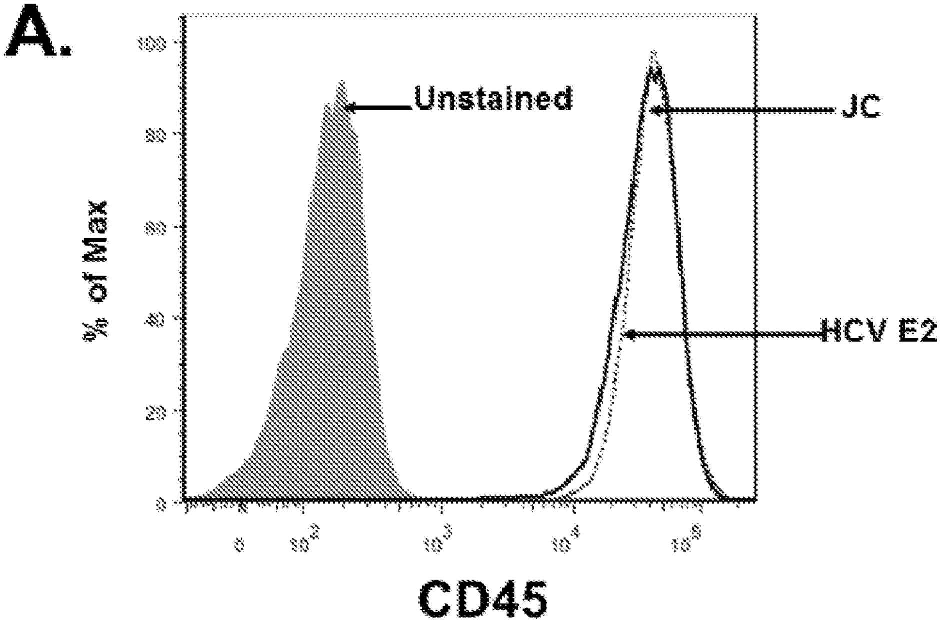
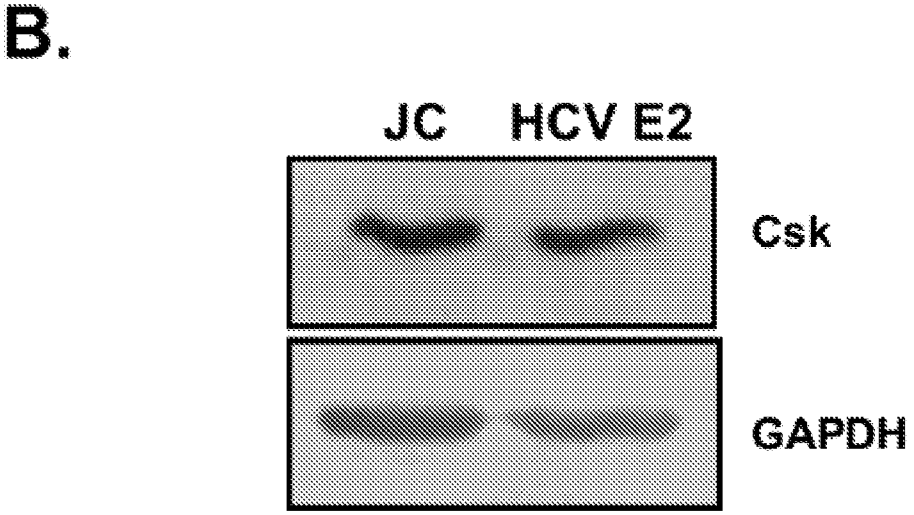
FIGS. 14A-B

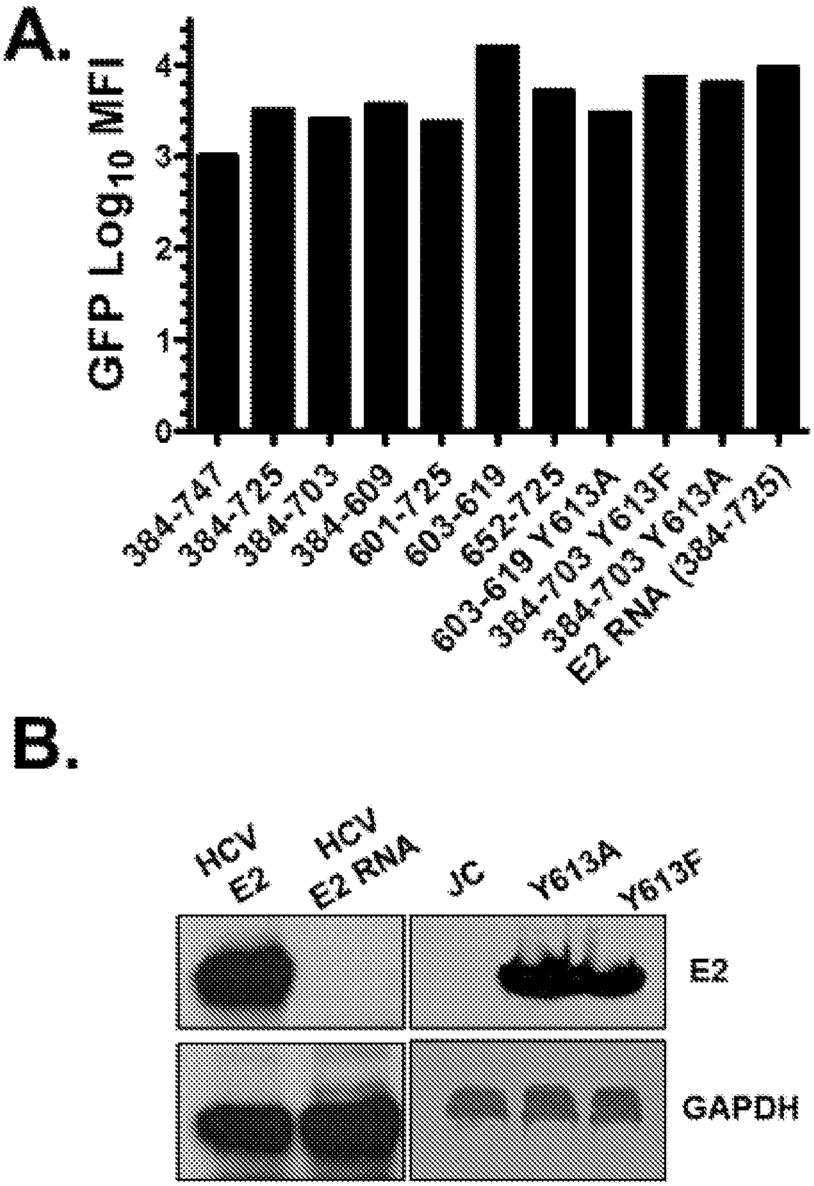
FIGS. 15A-B

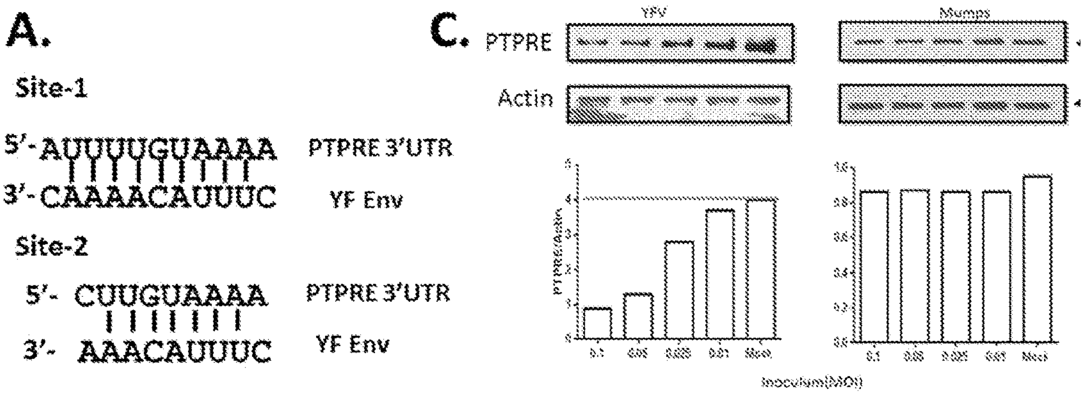
B.
| | | TCR Inhibition | Seed Mismatch |
|---|---|---|---|
| YFV Env - Y274 | CCUUUACAAACT | YES | 0 |
| YFV Env - Y274F | CCUUUTCAAACT | YES | 1 |
| YFV Env - Y274A | CCUUGCCAAACT | NO | 2 |
| YFV Env - Y274G | CCUUGCCAAACT | NO | 2 |
FIGS. 29A-C

SEQUENCE LISTING

<160> NUMBER OF SEQ ID NOS: 43

<210> SEQ ID NO 1
<211> LENGTH: 9401
<212> TYPE: DNA
<213> ORGANISM: Hepatitis C virus

<400> SEQUENCE: 1

```
gccagccccc tgatgggggc gacactccac catgaatcac tcccctgtga ggaactactg      60

tcttcacgca gaaagcgtct agccatggcg ttagtatgag tgtcgtgcag cctccaggac     120

ccccccuccc gggagagcca tagtggtctg cggaaccggt gagtacaccg gaattgccag     180

gacgaccggg tcctttcttg gatcaacccg ctcaatgcct ggagatttgg gcgtgccccc     240

gcaagactgc tagccgagta gtgttgggtc gcgaaaggcc ttgtggtact gcctgatagg     300

gtgcttgcga gtgccccggg aggtctcgta gaccgtgcac catgagcacg aatcctaaac     360

ctcaaaaaaa aaacaaacgt aacaccaacc gtcgcccaca ggacgtcaag ttcccgggtg     420

gcggtcagat cgttggtgga gtttacttgt tgccgcgcag gggccctaga ttgggtgtgc     480

gcgcgacgag aaagacttcc gagcggtcgc aacctcgagg tagacgtcag cctatcccca     540

aggctcgtcg gcccgagggc aggacctggg ctcagcccgg gtacccttgg cccctctatg     600

gcaatgaggg ctgcgggtgg gcgggatggc tcctgtctcc ccgtggctct cggcctagct     660

ggggccccac agacccccgg cgtaggtcgc gcaatttggg taaggtcatc gataccctta     720

cgtgcggctt cgccgacctc atggggtaca taccgctcgt cggcgcccct cttggaggcg     780

ctgccagggc cctggcgcat ggcgtccggg ttctggaaga cggcgtgaac tatgcaacag     840

ggaaccttcc tggttgctct ttctctatct tccttctggc cctgctctct tgcttgactg     900

tgcccgcttc ggcctaccaa gtgcgcaact ccacggggct ttaccacgtc accaatgatt     960

gccctaactc gagtattgtg tacgaggcgg ccgatgccat cctgcacact ccggggtgcg    1020

tcccttgcgt tcgtgagggc aacgcctcga ggtgttgggt ggcgatgacc cctacggtgg    1080

ccaccaggga tggcaaactc cccgcgacgc agcttcgacg tcacatcgat ctgcttgtcg    1140

ggagcgccac cctctgttcg gccctctacg tgggggacct atgcgggtct gtctttcttg    1200

tcggccaact gttcaccttc tctcccaggc gccactggac gacgcaaggt tgcaattgct    1260

ctatctatcc cggccatata acgggtcacc gcatggcatg ggatatgatg atgaactggt    1320

cccctacgac ggcgttggta atggctcagc tgctccggat cccacaagcc atcttggaca    1380

tgatcgctgg tgctcactgg ggagtcctgg cgggcatagc gtatttctcc atggtgggga    1440

actgggcgaa ggtcctggta gtgctgctgc tatttgccgg cgtcgacgcg gaaacccacg    1500

tcaccggggg aagtgccggc cacactgtgt ctggatttgt tagcctcctc gcaccaggcg    1560

ccaagcagaa cgtccagctg atcaacacca acggcagttg gcacctcaat agcacggccc    1620

tgaactgcaa tgatagcctc aacaccggct ggttggcagg gcttttctat caccacaagt    1680

tcaactcttc aggctgtcct gagaggctag ccagctgccg acccccttacc gattttgacc    1740

agggctgggg ccctatcagt tatgccaacg gaagcggccc cgaccagcgc ccctactgct    1800

ggcactaccc cccaaaacct tgcggtattg tgcccgcgaa gagtgtgtgt ggtccggtat    1860
```

-continued

```
attgcttcac tcccagcccc gtggtggtgg gaacgaccga caggtcgggc gcgcccacct   1920
acagctgggg tgaaaatgat acggacgtct tcgtccttaa caataccagg ccaccgctgg   1980
gcaattggtt cggttgtacc tggatgaact caactggatt caccaaagtg tgcggagcgc   2040
ctccttgtgt catcggaggg gcgggcaaca acaccctgca ctgccccact gattgcttcc   2100
gcaagcatcc ggacgccaca tactctcggt gcggctccgg tccctggatc acacccaggt   2160
gcctggtcga ctacccgtat aggctttggc attatccttg taccatcaac tacaccatat   2220
ttaaaatcag gatgtacgtg ggaggggtcg aacacaggct ggaagctgcc tgcaactgga   2280
cgcggggcga acgttgcgat ctggaagaca gggacaggtc cgagctcagc ccgttactgc   2340
tgaccactac acagtggcag gtcctcccgt gttccttcac aaccctacca gccttgtcca   2400
ccggcctcat ccacctccac cagaacattg tggacgtgca gtacttgtac ggggtggggt   2460
caagcatcgc gtcctgggcc attaagtggg agtacgtcgt tctcctgttc cttctgcttg   2520
cagacgcgcg cgtctgctcc tgcttgtgga tgatgctact catatcccaa gcggaggcgg   2580
ctttggagaa cctcgtaata cttaatgcag catccctggc cgggacgcac ggtcttgtat   2640
ccttcctcgt gttcttctgc tttgcatggt atttgaaggg taagtgggtg cccggagcgg   2700
tctacacctt ctacgggatg tggcctctcc tcctgctcct gttggcgttg ccccagcggg   2760
cgtacgcgct ggacacggag gtggccgcgt cgtgtggcgg tgttgttctc gtcgggttga   2820
tggcgctgac tctgtcacca tattacaagc gctatatcag ctggtgcttg tggtggcttc   2880
agtattttct gaccagagtg gaagcgcaac tgcacgtgtg gattcccccc ctcaacgtcc   2940
gaggggggcg cgacgccgtc atcttactca tgtgtgctgt acacccgact ctggtatttg   3000
acatcaccaa attgctgctg gccgtcttcg gacccctttg gattcttcaa gccagtttgc   3060
ttaaagtacc ctactttgtg cgcgtccaag gccttctccg gttctgcgcg ttagcgcgga   3120
agatgatcgg aggccattac gtgcaaatgg tcatcattaa gttaggggcg cttactggca   3180
cctatgttta taaccatctc actcctcttc gggactgggc gcacaacggc ttgcgagatc   3240
tggccgtggc tgtagagcca gtcgtcttct cccaaatgga gaccaagctc atcacgtggg   3300
gggcagatac cgccgcgtgc ggtgacatca tcaacggctt gcctgtttcc gcccgcaggg   3360
gccgggagat actgctcggg ccagccgatg gaatggtctc caaggggtgg aggttgctgg   3420
cgcccatcac ggcgtacgcc cagcagacaa ggggcctcct agggtgcata atcaccagcc   3480
taactggccg ggacaaaaac caagtggagg gtgaggtcca gattgtgtca actgctgccc   3540
aaaccttcct ggcaacgtgc atcaatgggg tgtgctggac tgtctaccac ggggccggaa   3600
cgaggaccat cgcgtcaccc aagggtcctg tcatccagat gtataccaat gtagaccaag   3660
accttgtggg ctggcccgct ccgcaaggta gccgctcatt gacaccctgc acttgcggct   3720
cctcggacct ttacctggtc acgaggcacg ccgatgtcat tcccgtgcgc cggcggggtg   3780
atagcagggg cagcctgctg tcgccccggc ccatttccta cttgaaaggc tcctcggggg   3840
gtccgctgtt gtgccccgcg gggcacgccg tgggcatatt tagggccgcg gtgtgcaccc   3900
gtggagtggc taaggcggtg gactttatcc ctgtggagaa cctagagaca accatgaggt   3960
ccccggtgtt cacggataac tcctctccac cagtagtgcc ccagagcttc caggtggctc   4020
acctccatgc tcccacaggc agcggcaaaa gcaccaaggt cccggctgca tatgcagctc   4080
agggctataa ggtgctagta ctcaacccct ctgttgctgc aacactgggc tttggtgctt   4140
acatgtccaa ggctcatggg atcgatccta acatcaggac cggggtgaga acaattacca   4200
ctggcagccc catcacgtac tccacctacg gcaagttcct tgccgacggc gggtgctcgg   4260
```

-continued

```
ggggcgctta tgacataata atttgtgacg agtgccactc cacggatgcc acatccatct   4320
tgggcatcgg cactgtcctt gaccaagcag agactgcggg ggcgagactg gttgtgctcg   4380
ccaccgccac ccctccgggc tccgtcactg tgccccatcc caacatcgag gaggttgctc   4440
tgtccaccac cggagagatc cctttttacg gcaaggctat ccccctcgaa gtaatcaagg   4500
gggggagaca tctcatcttc tgtcattcaa agaagaagtg cgacgaactc gccgcaaagc   4560
tggtcgcatt gggcatcaat gccgtggcct actaccgcgg tcttgacgtg tccgtcatcc   4620
cgaccagcgg cgatgttgtc gtcgtggcaa ccgatgccct catgaccggc tataccggcg   4680
acttcgactc ggtgatagac tgcaatacgt gtgtcaccca gacagtcgat ttcagccttg   4740
accctacctt caccattgag acaatcacgc tcccccagga tgctgtctcc cgcactcaac   4800
gtcggggcag gactggcagg gggaagccag gcatctacag atttgtggca ccgggggagc   4860
gcccctccgg catgttcgac tcgtccgtcc tctgtgagtg ctatgacgca ggctgtgctt   4920
ggtatgagct cacgcccgcc gagactacag ttaggctacg agcgtacatg aacaccccgg   4980
ggcttcccgt gtgccaggac catcttgaat tttgggaggg cgtctttaca ggcctcactc   5040
atatagatgc ccactttcta tcccagacaa agcagagtgg ggagaacctt ccttacctgg   5100
tagcgtacca agccaccgtg tgcgctaggg ctcaagcccc tcccccatcg tgggaccaga   5160
tgtggaagtg tttgattcgc ctcaagccca ccctccatgg gccaacaccc ctgctataca   5220
gactgggcgc tgttcagaat gaaatcaccc tgacgcaccc agtcaccaaa tacatcatga   5280
catgcatgtc ggccgacctg gaggtcgtca cgagcacctg ggtgctcgtt ggcggcgtcc   5340
tggctgcttt ggccgcgtat tgcctgtcaa caggctgcgt ggtcatagtg ggcagggtcg   5400
tcttgtccgg gaagccggca atcatacctg acagggaagt cctctaccga gagttcgatg   5460
agatggaaga gtgctctcag cacttaccgt acatcgagca agggatgatg ctcgccgagc   5520
agttcaagca gaaggccctc ggcctcctgc agaccgcgtc ccgtcaggca gaggttatcg   5580
cccctgctgt ccagaccaac tggcaaaaac tcgagacctt ctgggcgaag catatgtgga   5640
acttcatcag tgggatacaa tacttggcgg gcttgtcaac gctgcctggt aaccccgcca   5700
ttgcttcatt gatggctttt acagctgctg tcaccagccc actaaccact agccaaaccc   5760
tcctcttcaa catattgggg gggtgggtgg ctgcccagct cgccgccccc ggtgccgcta   5820
ctgcctttgt gggcgctggc ttagctggcg ccgccatcgg cagtgttgga ctggggaagg   5880
tcctcataga catccttgca gggtatggcg cgggcgtggc gggagctctt gtggcattca   5940
agatcatgag cggtgaggtc ccctccacgg aggacctggt caatctactg cccgccatcc   6000
tctcgcccgg agccctcgta gtcggcgtgg tctgtgcagc aatactgcgc cggcacgttg   6060
gcccgggcga gggggcagtg cagtggatga accggctgat agccttcgcc tcccggggga   6120
accatgtttc ccccacgcac tacgtgccgg agagcgatgc agctgcccgc gtcactgcca   6180
tactcagcag cctcactgta acccagctcc tgaggcgact gcaccagtgg ataagctcgg   6240
agtgtaccac tccatgctcc ggttcctggc taagggacat ctgggactgg atatgcgagg   6300
tgttgagcga ctttaagacc tggctaaaag ctaagctcat gccacagctg cctgggatcc   6360
cctttgtgtc ctgccagcgc gggtataagg gggtctggcg agtggacggc atcatgcaca   6420
ctcgctgcca ctgtggagct gagatcactg gacatgtcaa aaacgggacg atgaggatcg   6480
tcggtcctag gacctgcagg aacatgtgga gtgggacctt ccccattaat gcctacacca   6540
cgggcccctg tacccccctt cctgcgccga actacacgtt cgcgctatgg agggtgtctg   6600
```

-continued

```
cagaggaata tgtggagata aggcaggtgg gggacttcca ctacgtgacg ggtatgacta   6660
ctgacaatct caaatgcccg tgccaggtcc catcgcccga atttttcaca gaattggacg   6720
gggtgcgcct acataggttt gcgcccccct gcaagccctt gctgcgggag gaggtatcat   6780
tcagagtagg actccacgaa tacccggtag ggtcgcaatt accttgcgag cccgaaccgg   6840
acgtggccgt gttgacgtcc atgctcactg atccctccca tataacagca gaggcggccg   6900
ggcgaaggtt ggcgaggggga tcacccccct ctgtggccag ctcctcggct agccagctat   6960
ccgctccatc tctcaaggca acttgcaccg ctaaccatga ctcccctgat gctgagctca   7020
tagaggccaa cctcctatgg aggcaggaga tgggcggcaa catcaccagg gttgagtcag   7080
aaaacaaagt ggtgattctg gactccttcg atccgcttgt ggcggaggag gacgagcggg   7140
agatctccgt acccgcagaa atcctgcgga agtctcggag attcgcccag gccctgcccg   7200
tttgggcgcg gccggactat aaccccccgc tagtggagac gtggaaaaag cccgactacg   7260
aaccacctgt ggtccatggc tgtccgcttc cacctccaaa gtcccctcct gtgcctccgc   7320
ctcggaagaa gcggacggtg gtcctcactg aatcaaccct atctactgcc ttggccgagc   7380
tcgccaccag aagctttggc agctcctcaa cttccggcat tacgggcgac aatacgacaa   7440
catcctctga gcccgcccct tctggctgcc cccccgactc cgacgctgag tcctattcct   7500
ccatgccccc cctggagggg gagcctgggg atccggatct tagcgacggg tcatggtcaa   7560
cggtcagtag tgaggccaac gcggaggatg tcgtgtgctg ctcaatgtct tactcttgga   7620
caggcgcact cgtcaccccg tgcgccgcgg aagaacagaa actgcccatc aatgcactaa   7680
gcaactcgtt gctacgtcac cacaatttgg tgtattccac cacctcacgc agtgcttgcc   7740
aaaggcagaa gaaagtcaca tttgacagac tgcaagttct ggacagccat taccaggacg   7800
tactcaagga ggttaaagca gcggcgtcaa aagtgaaggc taacttgcta tccgtagagg   7860
aagcttgcag cctgacgccc ccacactcag ccaaatccaa gtttggttat ggggcaaaag   7920
acgtccgttg ccatgccaga aaggccgtaa cccacatcaa ctccgtgtgg aaagaccttc   7980
tggaagacaa tgtaacacca atagacacta ccatcatggc taagaacgag gttttctgcg   8040
ttcagcctga gaagggggggt cgtaagccag ctcgtctcat cgtgttcccc gatctgggcg   8100
tgcgcgtgtg cgaaaagatg gctttgtacg acgtggttac aaagctcccc ttggccgtga   8160
tgggaagctc ctacggattc caatactcac caggacagcg ggttgaattc ctcgtgcaag   8220
cgtggaagtc caagaaaacc ccaatggggt tctcgtatga tacccgctgc tttgactcca   8280
cagtcactga gagcgacatc cgtacggagg aggcaatcta ccaatgttgt gacctcgacc   8340
cccaagcccg cgtggccatc aagtccctca ccgagaggct ttatgttggg ggccctctta   8400
ccaattcaag gggggagaac tgcggctatc gcaggtgccg cgcgagcggc gtactgacaa   8460
ctagctgtgg taacaccctc acttgctaca tcaaggcccg ggcagcctgt cgagccgcag   8520
ggctccagga ctgcaccatg ctcgtgtgtg gcgacgactt agtcgttatc tgtgaaagcg   8580
cgggggtcca ggaggacgcg gcgagcctga gagccttcac ggaggctatg accaggtact   8640
ccgcccccccc tggggacccc ccacaaccag aatacgactt ggagctcata acatcatgct   8700
cctccaacgt gtcagtcgcc cacgacggcg ctggaaagag ggtctactac ctcacccgtg   8760
accctacaac ccccctcgcg agagctgcgt gggagacagc aagacacact ccagtcaatt   8820
cctggctagg caacataatc atgtttgccc ccacactgtg ggcgaggatg atactgatga   8880
cccatttctt tagcgtcctt atagccaggg accagcttga acaggccctc gattgcgaga   8940
tctacggggc ctgctactcc atagaaccac ttgatctacc tccaatcatt caaagactcc   9000
```

atggcctcag cgcattttca ctccacagtt actctccagg tgaaattaat agggtggccg 9060
catgcctcag aaaacttggg gtaccgccct tgcgagcttg gagacaccgg gcccggagcg 9120
tccgcgctag gcttctggcc agaggaggca gggctgccat atgtggcaag tacctcttca 9180
actgggcagt aagaacaaag ctcaaactca ctccaatagc ggccgctggc cagctggact 9240
tgtccggctg gttcacggct ggctacagcg gggagacat ttatcacagc gtgtctcatg 9300
cccggccccg ctggatctgg ttttgcctac tcctgcttgc tgcaggggta ggcatctacc 9360
tcctccccaa ccgatgaagg ttggggtaaa cactccggcc t 9401

<210> SEQ ID NO 2
<211> LENGTH: 3011
<212> TYPE: PRT
<213> ORGANISM: Hepatitis C virus

<400> SEQUENCE: 2

Met Ser Thr Asn Pro Lys Pro Gln Lys Lys Asn Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Tyr
180 185 190

Gln Val Arg Asn Ser Thr Gly Leu Tyr His Val Thr Asn Asp Cys Pro
195 200 205

Asn Ser Ser Ile Val Tyr Glu Ala Ala Asp Ala Ile Leu His Thr Pro
210 215 220

Gly Cys Val Pro Cys Val Arg Glu Gly Asn Ala Ser Arg Cys Trp Val
225 230 235 240

Ala Met Thr Pro Thr Val Ala Thr Arg Asp Gly Lys Leu Pro Ala Thr
245 250 255

Gln Leu Arg Arg His Ile Asp Leu Leu Val Gly Ser Ala Thr Leu Cys
260 265 270

Ser Ala Leu Tyr Val Gly Asp Leu Cys Gly Ser Val Phe Leu Val Gly
275 280 285

Gln Leu Phe Thr Phe Ser Pro Arg Arg His Trp Thr Thr Gln Gly Cys
290 295 300

-continued

```
Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720
```

-continued

```
Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Arg
        995                 1000                1005

Glu Ile  Leu Leu Gly Pro Ala  Asp Gly Met Val Ser  Lys Gly Trp
    1010                1015                1020

Arg Leu  Leu Ala Pro Ile Thr  Ala Tyr Ala Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Ala Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Pro Lys Gly  Pro Val Ile
    1085                1090                1095

Gln Met  Tyr Thr Asn Val Asp  Gln Asp Leu Val Gly  Trp Pro Ala
    1100                1105                1110

Pro Gln  Gly Ser Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
```

```
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Ile Phe  Arg Ala Ala Val Cys  Thr Arg Gly
    1175                1180                1185

Val Ala  Lys Ala Val Asp Phe  Ile Pro Val Glu Asn  Leu Glu Thr
    1190                1195                1200

Thr Met  Arg Ser Pro Val Phe  Thr Asp Asn Ser Ser  Pro Pro Val
    1205                1210                1215

Val Pro  Gln Ser Phe Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260

Phe Gly  Ala Tyr Met Ser Lys  Ala His Gly Ile Asp  Pro Asn Ile
    1265                1270                1275

Arg Thr  Gly Val Arg Thr Ile  Thr Thr Gly Ser Pro  Ile Thr Tyr
    1280                1285                1290

Ser Thr  Tyr Gly Lys Phe Leu  Ala Asp Gly Gly Cys  Ser Gly Gly
    1295                1300                1305

Ala Tyr  Asp Ile Ile Ile Cys  Asp Glu Cys His Ser  Thr Asp Ala
    1310                1315                1320

Thr Ser  Ile Leu Gly Ile Gly  Thr Val Leu Asp Gln  Ala Glu Thr
    1325                1330                1335

Ala Gly  Ala Arg Leu Val Val  Leu Ala Thr Ala Thr  Pro Pro Gly
    1340                1345                1350

Ser Val  Thr Val Pro His Pro  Asn Ile Glu Glu Val  Ala Leu Ser
    1355                1360                1365

Thr Thr  Gly Glu Ile Pro Phe  Tyr Gly Lys Ala Ile  Pro Leu Glu
    1370                1375                1380

Val Ile  Lys Gly Gly Arg His  Leu Ile Phe Cys His  Ser Lys Lys
    1385                1390                1395

Lys Cys  Asp Glu Leu Ala Ala  Lys Leu Val Ala Leu  Gly Ile Asn
    1400                1405                1410

Ala Val  Ala Tyr Tyr Arg Gly  Leu Asp Val Ser Val  Ile Pro Thr
    1415                1420                1425

Ser Gly  Asp Val Val Val Val  Ala Thr Asp Ala Leu  Met Thr Gly
    1430                1435                1440

Tyr Thr  Gly Asp Phe Asp Ser  Val Ile Asp Cys Asn  Thr Cys Val
    1445                1450                1455

Thr Gln  Thr Val Asp Phe Ser  Leu Asp Pro Thr Phe  Thr Ile Glu
    1460                1465                1470

Thr Ile  Thr Leu Pro Gln Asp  Ala Val Ser Arg Thr  Gln Arg Arg
    1475                1480                1485

Gly Arg  Thr Gly Arg Gly Lys  Pro Gly Ile Tyr Arg  Phe Val Ala
    1490                1495                1500

Pro Gly  Glu Arg Pro Ser Gly  Met Phe Asp Ser Ser  Val Leu Cys
    1505                1510                1515

Glu Cys  Tyr Asp Ala Gly Cys  Ala Trp Tyr Glu Leu  Thr Pro Ala
    1520                1525                1530
```

-continued

```
Glu Thr  Thr Val Arg Leu Arg  Ala Tyr Met Asn Thr  Pro Gly Leu
    1535                 1540                 1545

Pro Val  Cys Gln Asp His Leu  Glu Phe Trp Glu Gly  Val Phe Thr
    1550                 1555                 1560

Gly Leu  Thr His Ile Asp Ala  His Phe Leu Ser Gln  Thr Lys Gln
    1565                 1570                 1575

Ser Gly  Glu Asn Leu Pro Tyr  Leu Val Ala Tyr Gln  Ala Thr Val
    1580                 1585                 1590

Cys Ala  Arg Ala Gln Ala Pro  Pro Pro Ser Trp Asp  Gln Met Trp
    1595                 1600                 1605

Lys Cys  Leu Ile Arg Leu Lys  Pro Thr Leu His Gly  Pro Thr Pro
    1610                 1615                 1620

Leu Leu  Tyr Arg Leu Gly Ala  Val Gln Asn Glu Ile  Thr Leu Thr
    1625                 1630                 1635

His Pro  Val Thr Lys Tyr Ile  Met Thr Cys Met Ser  Ala Asp Leu
    1640                 1645                 1650

Glu Val  Val Thr Ser Thr Trp  Val Leu Val Gly Gly  Val Leu Ala
    1655                 1660                 1665

Ala Leu  Ala Ala Tyr Cys Leu  Ser Thr Gly Cys Val  Val Ile Val
    1670                 1675                 1680

Gly Arg  Val Val Leu Ser Gly  Lys Pro Ala Ile Ile  Pro Asp Arg
    1685                 1690                 1695

Glu Val  Leu Tyr Arg Glu Phe  Asp Glu Met Glu Glu  Cys Ser Gln
    1700                 1705                 1710

His Leu  Pro Tyr Ile Glu Gln  Gly Met Met Leu Ala  Glu Gln Phe
    1715                 1720                 1725

Lys Gln  Lys Ala Leu Gly Leu  Leu Gln Thr Ala Ser  Arg Gln Ala
    1730                 1735                 1740

Glu Val  Ile Ala Pro Ala Val  Gln Thr Asn Trp Gln  Lys Leu Glu
    1745                 1750                 1755

Thr Phe  Trp Ala Lys His Met  Trp Asn Phe Ile Ser  Gly Ile Gln
    1760                 1765                 1770

Tyr Leu  Ala Gly Leu Ser Thr  Leu Pro Gly Asn Pro  Ala Ile Ala
    1775                 1780                 1785

Ser Leu  Met Ala Phe Thr Ala  Ala Val Thr Ser Pro  Leu Thr Thr
    1790                 1795                 1800

Ser Gln  Thr Leu Leu Phe Asn  Ile Leu Gly Gly Trp  Val Ala Ala
    1805                 1810                 1815

Gln Leu  Ala Ala Pro Gly Ala  Ala Thr Ala Phe Val  Gly Ala Gly
    1820                 1825                 1830

Leu Ala  Gly Ala Ala Ile Gly  Ser Val Gly Leu Gly  Lys Val Leu
    1835                 1840                 1845

Ile Asp  Ile Leu Ala Gly Tyr  Gly Ala Gly Val Ala  Gly Ala Leu
    1850                 1855                 1860

Val Ala  Phe Lys Ile Met Ser  Gly Glu Val Pro Ser  Thr Glu Asp
    1865                 1870                 1875

Leu Val  Asn Leu Leu Pro Ala  Ile Leu Ser Pro Gly  Ala Leu Val
    1880                 1885                 1890

Val Gly  Val Val Cys Ala Ala  Ile Leu Arg Arg His  Val Gly Pro
    1895                 1900                 1905

Gly Glu  Gly Ala Val Gln Trp  Met Asn Arg Leu Ile  Ala Phe Ala
    1910                 1915                 1920
```

-continued

```
Ser Arg  Gly Asn His Val Ser  Pro Thr His Tyr Val  Pro Glu Ser
    1925                 1930                 1935

Asp Ala  Ala Ala Arg Val Thr  Ala Ile Leu Ser Ser  Leu Thr Val
    1940                 1945                 1950

Thr Gln  Leu Leu Arg Arg Leu  His Gln Trp Ile Ser  Ser Glu Cys
    1955                 1960                 1965

Thr Thr  Pro Cys Ser Gly Ser  Trp Leu Arg Asp Ile  Trp Asp Trp
    1970                 1975                 1980

Ile Cys  Glu Val Leu Ser Asp  Phe Lys Thr Trp Leu  Lys Ala Lys
    1985                 1990                 1995

Leu Met  Pro Gln Leu Pro Gly  Ile Pro Phe Val Ser  Cys Gln Arg
    2000                 2005                 2010

Gly Tyr  Lys Gly Val Trp Arg  Val Asp Gly Ile Met  His Thr Arg
    2015                 2020                 2025

Cys His  Cys Gly Ala Glu Ile  Thr Gly His Val Lys  Asn Gly Thr
    2030                 2035                 2040

Met Arg  Ile Val Gly Pro Arg  Thr Cys Arg Asn Met  Trp Ser Gly
    2045                 2050                 2055

Thr Phe  Pro Ile Asn Ala Tyr  Thr Thr Gly Pro Cys  Thr Pro Leu
    2060                 2065                 2070

Pro Ala  Pro Asn Tyr Thr Phe  Ala Leu Trp Arg Val  Ser Ala Glu
    2075                 2080                 2085

Glu Tyr  Val Glu Ile Arg Gln  Val Gly Asp Phe His  Tyr Val Thr
    2090                 2095                 2100

Gly Met  Thr Thr Asp Asn Leu  Lys Cys Pro Cys Gln  Val Pro Ser
    2105                 2110                 2115

Pro Glu  Phe Phe Thr Glu Leu  Asp Gly Val Arg Leu  His Arg Phe
    2120                 2125                 2130

Ala Pro  Pro Cys Lys Pro Leu  Leu Arg Glu Glu Val  Ser Phe Arg
    2135                 2140                 2145

Val Gly  Leu His Glu Tyr Pro  Val Gly Ser Gln Leu  Pro Cys Glu
    2150                 2155                 2160

Pro Glu  Pro Asp Val Ala Val  Leu Thr Ser Met Leu  Thr Asp Pro
    2165                 2170                 2175

Ser His  Ile Thr Ala Glu Ala  Ala Gly Arg Arg Leu  Ala Arg Gly
    2180                 2185                 2190

Ser Pro  Pro Ser Val Ala Ser  Ser Ser Ala Ser Gln  Leu Ser Ala
    2195                 2200                 2205

Pro Ser  Leu Lys Ala Thr Cys  Thr Ala Asn His Asp  Ser Pro Asp
    2210                 2215                 2220

Ala Glu  Leu Ile Glu Ala Asn  Leu Leu Trp Arg Gln  Glu Met Gly
    2225                 2230                 2235

Gly Asn  Ile Thr Arg Val Glu  Ser Glu Asn Lys Val  Val Ile Leu
    2240                 2245                 2250

Asp Ser  Phe Asp Pro Leu Val  Ala Glu Glu Asp Glu  Arg Glu Ile
    2255                 2260                 2265

Ser Val  Pro Ala Glu Ile Leu  Arg Lys Ser Arg Arg  Phe Ala Gln
    2270                 2275                 2280

Ala Leu  Pro Val Trp Ala Arg  Pro Asp Tyr Asn Pro  Pro Leu Val
    2285                 2290                 2295

Glu Thr  Trp Lys Lys Pro Asp  Tyr Glu Pro Pro Val  Val His Gly
    2300                 2305                 2310

Cys Pro  Leu Pro Pro Pro Lys  Ser Pro Pro Val Pro  Pro Pro Arg
```

-continued

```
    2315                2320                2325

Lys Lys  Arg Thr Val Val Leu  Thr Glu Ser Thr Leu  Ser Thr Ala
    2330                2335                2340

Leu Ala  Glu Leu Ala Thr Arg  Ser Phe Gly Ser Ser  Ser Thr Ser
    2345                2350                2355

Gly Ile  Thr Gly Asp Asn Thr  Thr Thr Ser Ser Glu  Pro Ala Pro
    2360                2365                2370

Ser Gly  Cys Pro Pro Asp Ser  Asp Ala Glu Ser Tyr  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Ser  Glu Ala Asn Ala Glu  Asp Val Val
    2405                2410                2415

Cys Cys  Ser Met Ser Tyr Ser  Trp Thr Gly Ala Leu  Val Thr Pro
    2420                2425                2430

Cys Ala  Ala Glu Glu Gln Lys  Leu Pro Ile Asn Ala  Leu Ser Asn
    2435                2440                2445

Ser Leu  Leu Arg His His Asn  Leu Val Tyr Ser Thr  Thr Ser Arg
    2450                2455                2460

Ser Ala  Cys Gln Arg Gln Lys  Lys Val Thr Phe Asp  Arg Leu Gln
    2465                2470                2475

Val Leu  Asp Ser His Tyr Gln  Asp Val Leu Lys Glu  Val Lys Ala
    2480                2485                2490

Ala Ala  Ser Lys Val Lys Ala  Asn Leu Leu Ser Val  Glu Glu Ala
    2495                2500                2505

Cys Ser  Leu Thr Pro Pro His  Ser Ala Lys Ser Lys  Phe Gly Tyr
    2510                2515                2520

Gly Ala  Lys Asp Val Arg Cys  His Ala Arg Lys Ala  Val Thr His
    2525                2530                2535

Ile Asn  Ser Val Trp Lys Asp  Leu Leu Glu Asp Asn  Val Thr Pro
    2540                2545                2550

Ile Asp  Thr Thr Ile Met Ala  Lys Asn Glu Val Phe  Cys Val Gln
    2555                2560                2565

Pro Glu  Lys Gly Gly Arg Lys  Pro Ala Arg Leu Ile  Val Phe Pro
    2570                2575                2580

Asp Leu  Gly Val Arg Val Cys  Glu Lys Met Ala Leu  Tyr Asp Val
    2585                2590                2595

Val Thr  Lys Leu Pro Leu Ala  Val Met Gly Ser Ser  Tyr Gly Phe
    2600                2605                2610

Gln Tyr  Ser Pro Gly Gln Arg  Val Glu Phe Leu Val  Gln Ala Trp
    2615                2620                2625

Lys Ser  Lys Lys Thr Pro Met  Gly Phe Ser Tyr Asp  Thr Arg Cys
    2630                2635                2640

Phe Asp  Ser Thr Val Thr Glu  Ser Asp Ile Arg Thr  Glu Glu Ala
    2645                2650                2655

Ile Tyr  Gln Cys Cys Asp Leu  Asp Pro Gln Ala Arg  Val Ala Ile
    2660                2665                2670

Lys Ser  Leu Thr Glu Arg Leu  Tyr Val Gly Gly Pro  Leu Thr Asn
    2675                2680                2685

Ser Arg  Gly Glu Asn Cys Gly  Tyr Arg Arg Cys Arg  Ala Ser Gly
    2690                2695                2700

Val Leu  Thr Thr Ser Cys Gly  Asn Thr Leu Thr Cys  Tyr Ile Lys
    2705                2710                2715
```

```
Ala Arg  Ala Ala Cys Arg Ala  Ala Gly Leu Gln Asp  Cys Thr Met
    2720                 2725                 2730

Leu Val  Cys Gly Asp Asp Leu  Val Val Ile Cys Glu  Ser Ala Gly
    2735                 2740                 2745

Val Gln  Glu Asp Ala Ala Ser  Leu Arg Ala Phe Thr  Glu Ala Met
    2750                 2755                 2760

Thr Arg  Tyr Ser Ala Pro Pro  Gly Asp Pro Pro Gln  Pro Glu Tyr
    2765                 2770                 2775

Asp Leu  Glu Leu Ile Thr Ser  Cys Ser Ser Asn Val  Ser Val Ala
    2780                 2785                 2790

His Asp  Gly Ala Gly Lys Arg  Val Tyr Tyr Leu Thr  Arg Asp Pro
    2795                 2800                 2805

Thr Thr  Pro Leu Ala Arg Ala  Ala Trp Glu Thr Ala  Arg His Thr
    2810                 2815                 2820

Pro Val  Asn Ser Trp Leu Gly  Asn Ile Ile Met Phe  Ala Pro Thr
    2825                 2830                 2835

Leu Trp  Ala Arg Met Ile Leu  Met Thr His Phe Phe  Ser Val Leu
    2840                 2845                 2850

Ile Ala  Arg Asp Gln Leu Glu  Gln Ala Leu Asp Cys  Glu Ile Tyr
    2855                 2860                 2865

Gly Ala  Cys Tyr Ser Ile Glu  Pro Leu Asp Leu Pro  Pro Ile Ile
    2870                 2875                 2880

Gln Arg  Leu His Gly Leu Ser  Ala Phe Ser Leu His  Ser Tyr Ser
    2885                 2890                 2895

Pro Gly  Glu Ile Asn Arg Val  Ala Ala Cys Leu Arg  Lys Leu Gly
    2900                 2905                 2910

Val Pro  Pro Leu Arg Ala Trp  Arg His Arg Ala Arg  Ser Val Arg
    2915                 2920                 2925

Ala Arg  Leu Leu Ala Arg Gly  Gly Arg Ala Ala Ile  Cys Gly Lys
    2930                 2935                 2940

Tyr Leu  Phe Asn Trp Ala Val  Arg Thr Lys Leu Lys  Leu Thr Pro
    2945                 2950                 2955

Ile Ala  Ala Ala Gly Gln Leu  Asp Leu Ser Gly Trp  Phe Thr Ala
    2960                 2965                 2970

Gly Tyr  Ser Gly Gly Asp Ile  Tyr His Ser Val Ser  His Ala Arg
    2975                 2980                 2985

Pro Arg  Trp Ile Trp Phe Cys  Leu Leu Leu Leu Ala  Ala Gly Val
    2990                 2995                 3000

Gly Ile  Tyr Leu Leu Pro Asn  Arg
    3005                 3010
```

<210> SEQ ID NO 3
<211> LENGTH: 50
<212> TYPE: DNA
<213> ORGANISM: Artificial sequence
<220> FEATURE:
<223> OTHER INFORMATION: Synthetic nucleic acid

<400> SEQUENCE: 3
ctcacgccaa ggtgcctgat cgactacccc tacaggctct ggcattatcc 50

<210> SEQ ID NO 4
<211> LENGTH: 51
<212> TYPE: DNA
<213> ORGANISM: Artificial sequence
<220> FEATURE:

<223> OTHER INFORMATION: Synthetic nucleic acid

<400> SEQUENCE: 4
ctcacgccaa ggtgcctgat cgactacccc tacaggctct ggcattaccc c 51

<210> SEQ ID NO 5
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 5
gacaacaacc tttacaaact acatggt 27

<210> SEQ ID NO 6
<211> LENGTH: 17
<212> TYPE: PRT
<213> ORGANISM: Hepatitis C virus

<400> SEQUENCE: 6

Leu Thr Pro Arg Cys Leu Ile Asp Tyr Pro Tyr Arg Leu Trp His Tyr
1 5 10 15

Pro

<210> SEQ ID NO 7
<211> LENGTH: 51
<212> TYPE: DNA
<213> ORGANISM: Hepatitis C virus

<400> SEQUENCE: 7
ctcacgccaa ggtgcctgat cgactacccc tacaggctct ggcattaccc c 51

<210> SEQ ID NO 8
<211> LENGTH: 51
<212> TYPE: DNA
<213> ORGANISM: Hepatitis C virus

<400> SEQUENCE: 8
ttgacacctc gctgcatggt cgactatcca taccggcttt ggcattaccc a 51

<210> SEQ ID NO 9
<211> LENGTH: 51
<212> TYPE: DNA
<213> ORGANISM: Hepatitis C virus

<400> SEQUENCE: 9
ctcacaaaaa ggtgcctgat cgactacccc tacaggctct ggcattacaa a 51

<210> SEQ ID NO 10
<211> LENGTH: 140
<212> TYPE: DNA
<213> ORGANISM: Artificial sequence
<220> FEATURE:
<223> OTHER INFORMATION: Synthetic nucleic acid

<400> SEQUENCE: 10
gccgccagtg tgctggaatt cggctttcct gataccactt acctcaaatg cggctctggg 60
ccctggctca cgccaaggtg cctgatcgac taccccctaca ggctctggca ttacccctgc 120
acactgtagg caccatcaat 140

<210> SEQ ID NO 11

<211> LENGTH: 22
<212> TYPE: RNA
<213> ORGANISM: Hepatitis C virus

<400> SEQUENCE: 11
caaaugccaa auagugauua ga 22

<210> SEQ ID NO 12
<211> LENGTH: 22
<212> TYPE: RNA
<213> ORGANISM: Hepatitis C virus

<400> SEQUENCE: 12
ccccuacagg cucuggcauu ac 22

<210> SEQ ID NO 13
<211> LENGTH: 22
<212> TYPE: RNA
<213> ORGANISM: Hepatitis C virus

<400> SEQUENCE: 13 auaaaugccag ugaauguugc ug 22

<210> SEQ ID NO 14
<211> LENGTH: 22
<212> TYPE: RNA
<213> ORGANISM: Hepatitis C virus

<400> SEQUENCE: 14
ccccuacagg cucuggcauu ac 22

<210> SEQ ID NO 15
<211> LENGTH: 65
<212> TYPE: RNA
<213> ORGANISM: Hepatitis C virus

<400> SEQUENCE: 15
ccccucacgc augacggaca aguacagauc gacuaacccu acuguacuug uccgucaugc 60
acccc 65

<210> SEQ ID NO 16
<211> LENGTH: 9
<212> TYPE: PRT
<213> ORGANISM: Yellow fever virus

<400> SEQUENCE: 16

Asp Asn Asn Leu Tyr Lys Leu His Gly
1 5

<210> SEQ ID NO 17
<211> LENGTH: 9
<212> TYPE: PRT
<213> ORGANISM: Yellow fever virus

<400> SEQUENCE: 17

Phe Gly Asp Ser Tyr Ile Ile Val Gly
1 5

<210> SEQ ID NO 18
<211> LENGTH: 11
<212> TYPE: RNA
<213> ORGANISM: Yellow fever virus

<400> SEQUENCE: 18

-continued auuuuguaaa a 11

<210> SEQ ID NO 19
<211> LENGTH: 11
<212> TYPE: RNA
<213> ORGANISM: Yellow fever virus

<400> SEQUENCE: 19
cuuuacaaaa c 11

<210> SEQ ID NO 20
<211> LENGTH: 9
<212> TYPE: RNA
<213> ORGANISM: Yellow fever virus

<400> SEQUENCE: 20 cuuguaaaa 9

<210> SEQ ID NO 21
<211> LENGTH: 9
<212> TYPE: RNA
<213> ORGANISM: Yellow fever virus

<400> SEQUENCE: 21 cuuuacaaa 9

<210> SEQ ID NO 22
<211> LENGTH: 9
<212> TYPE: RNA
<213> ORGANISM: Yellow fever virus

<400> SEQUENCE: 22 uuuacaaaa 9

<210> SEQ ID NO 23
<211> LENGTH: 12
<212> TYPE: DNA
<213> ORGANISM: Yellow fever virus

<400> SEQUENCE: 23
ccuuuacaaa ct 12

<210> SEQ ID NO 24
<211> LENGTH: 12
<212> TYPE: DNA
<213> ORGANISM: Yellow fever virus

<400> SEQUENCE: 24
ccuuutcaaa ct 12

<210> SEQ ID NO 25
<211> LENGTH: 12
<212> TYPE: DNA
<213> ORGANISM: Yellow fever virus

<400> SEQUENCE: 25
ccuugccaaa ct 12

<210> SEQ ID NO 26
<211> LENGTH: 12
<212> TYPE: DNA
<213> ORGANISM: Yellow fever virus

<400> SEQUENCE: 26
ccuugccaaa ct 12

<210> SEQ ID NO 27
<211> LENGTH: 1089
<212> TYPE: DNA
<213> ORGANISM: Hepatitis C virus

<400> SEQUENCE: 27
gaaacccatg tgaccggcgg caacgcgggc cgtaccaccg cgggcctggt gggcctgctg 60
accccgggcg cgaaacagaa cattcagctg attaacacca acggcagctg gcatattaac 120
agcaccgcgc tgaactgcaa cgaaagcctg aacaccggct ggctggcggg cctgttttat 180
cagcataaat ttaacagcag cggctgcccg gaacgtctgg cgagctgccg tcgtctgacc 240
gattttgcgc agggctgggg cccgattagc tatgcgaacg gcagcggcct ggatgaacgt 300
ccgtattgct ggcattatcc gccgcgtccg tgcggcattg tgccggcgaa aagcgtgtgc 360
ggcccggtgt attgctttac cccgagcccg gtggtggtgg gcaccaccga tcgtagcggc 420
gcgccgacct atagctgggg cgcgaacgat accgatgtgt ttgtgctgaa caacacccgt 480
ccgccgctgg gcaactggtt tggctgcacc tggatgaaca gcaccggctt taccaaagtg 540
tgcggcgcgc cgccgtgcgt gattggcggc gtgggcaaca acaccctgct gtgcccgacc 600
gattgctttc gtaaatatcc ggaagcgacc tatagccgtt gcggcagcgg cccgcgtatt 660
accccgcgtt gcatggtgga ttatccgtat cgtctgtggc attatccgtg caccattaac 720
tataccattt ttaaagtgcg tatgtatgtg ggcggcgtgg aacatcgtct ggaagcggcg 780
tgcaactgga cccgtggcga acgttgcgat ctggaagatc gtgatcgtag cgaactgagc 840
ccgctgctgc tgagcaccac ccagtggcag gtgctgccgt gcagctttac caccctgccg 900
gcgctgagca ccggcctgat tcatctgcat cagaacattg tggatgtgca gtatctgtat 960
ggcgtgggca gcagcattgc gagctgggcg attaaatggg aatatgtggt gctgctgttt 1020
ctgctgctgg cggatgcgcg tgtgtgcagc tgcctgtgga tgatgctgct gattagccag 1080
gcggaagcg 1089

<210> SEQ ID NO 28
<211> LENGTH: 1479
<212> TYPE: DNA
<213> ORGANISM: Yellow fever virus

<400> SEQUENCE: 28
gctcactgca ttggaattac tgacagggat ttcattgagg gggtgcatgg aggaacttgg 60
gtttcagcta ccctggagca agacaagtgt gtcactgtta tggcccctga caagccttca 120
ttggacatct cactagagac agtagccatt gatagacctg ctgaggtgag gaaagtgtgt 180
tacaatgcag ttctcactca tgtgaagatt aatgacaagt gccccagcac tggagaggcc 240
cacctagctg aagagaacga aggggacaat gcgtgcaagc gcacttattc tgatagaggc 300
tggggcaatg gctgtggcct atttgggaaa gggagcattg tggcatgcgc caaattcact 360
tgtgccaaat ccatgagttt gtttgaggtt gatcagacca aaattcagta tgtcatcaga 420
gcacaattgc atgtaggggc caagcaggaa aattggaata ccgacattaa gactctcaag 480
tttgatgccc tgtcaggctc ccaggaagtc gagttcattg ggtatggaaa agctacactg 540
gaatgccagg tgcaaactgc ggtggacttt ggtaacagtt acatcgctga gatggaaaca 600
gagagctgga tagtggacag acagtgggcc caggacttga ccctgccatg gcagagtgga 660
agtggcgggg tgtggagaga gatgcatcat cttgtcgaat ttgaacctcc gcatgccgcc 720
actatcagag tactggccct gggaaaccag gaaggctcct tgaaaacagc tcttactggc 780
gcaatgaggg ttacaaagga cacaaatgac aacaaccttt acaaactaca tggtggacat 840
gtttcttgca gagtgaaatt gtcagctttg acactcaagg ggacatccta caaaatatgc 900
actgacaaaa tgttttttgt caagaaccca actgacactg gccatggcac tgttgtgatg 960
caggtgaaag tgtcaaaagg agccccctgc aggattccag tgatagtagc tgatgatctt 1020
acagcggcaa tcaataaagg cattttggtt acagttaacc ccatcgcctc aaccaatgat 1080
gatgaagtgc tgattgaggt gaacccacct tttggagaca gctacattat cgttgggaga 1140
ggagattcac gtctcactta ccagtggcac aaagagggaa gctcaatagg aaagttgttc 1200
actcagacca tgaaaggcgt ggaacgcctg gccgtcatgg gagacaccgc ctgggatttc 1260
agctccgctg gagggttctt cacttcggtt gggaaaggaa ttcatacggt gtttggctct 1320
gcctttcagg ggctatttgg cggcttgaac tggataacaa aggtcatcat gggggcggta 1380
cttatatggg ttggcatcaa cacaagaaac atgacaatgt ccatgagcat gatcttggta 1440
ggagtgatca tgatgttttt gtctctagga gttggggcg 1479

<210> SEQ ID NO 29
<211> LENGTH: 22
<212> TYPE: DNA
<213> ORGANISM: Artificial sequence
<220> FEATURE:
<223> OTHER INFORMATION: Synthetic primer

<400> SEQUENCE: 29
ctccacccaa tgaatcactc cc 22

<210> SEQ ID NO 30
<211> LENGTH: 20
<212> TYPE: DNA
<213> ORGANISM: Artificial sequence
<220> FEATURE:
<223> OTHER INFORMATION: Synthetic primer

<400> SEQUENCE: 30
gaggtttagg attcgtgctc 20

<210> SEQ ID NO 31
<211> LENGTH: 20
<212> TYPE: DNA
<213> ORGANISM: Artificial sequence
<220> FEATURE:
<223> OTHER INFORMATION: Synthetic primer

<400> SEQUENCE: 31
cgttagtatg agtgtcgtgc 20

<210> SEQ ID NO 32
<211> LENGTH: 20
<212> TYPE: DNA
<213> ORGANISM: Artificial sequence
<220> FEATURE:
<223> OTHER INFORMATION: Synthetic primer

<400> SEQUENCE: 32
gatgcacggt ctacgagacc 20

<210> SEQ ID NO 33

<211> LENGTH: 20
<212> TYPE: DNA
<213> ORGANISM: Artificial sequence
<220> FEATURE:
<223> OTHER INFORMATION: Synthetic primer

<400> SEQUENCE: 33
atcccatcac catcttccag 20

<210> SEQ ID NO 34
<211> LENGTH: 19
<212> TYPE: DNA
<213> ORGANISM: Artificial sequence
<220> FEATURE:
<223> OTHER INFORMATION: Synthetic primer

<400> SEQUENCE: 34
ccatcacgcc acagtttcc 19

<210> SEQ ID NO 35
<211> LENGTH: 17
<212> TYPE: DNA
<213> ORGANISM: Artificial sequence
<220> FEATURE:
<223> OTHER INFORMATION: Synthetic primer

<400> SEQUENCE: 35
attgatggtg cctacag 17

<210> SEQ ID NO 36
<211> LENGTH: 21
<212> TYPE: DNA
<213> ORGANISM: Artificial sequence
<220> FEATURE:
<223> OTHER INFORMATION: Synthetic primer

<400> SEQUENCE: 36
tcctgatacc acttacctca a 21

<210> SEQ ID NO 37
<211> LENGTH: 27
<212> TYPE: DNA
<213> ORGANISM: Yellow fever virus

<400> SEQUENCE: 37
gacaacaacc uuuacaaact acatggt 27

<210> SEQ ID NO 38
<211> LENGTH: 9
<212> TYPE: DNA
<213> ORGANISM: Artificial sequence
<220> FEATURE:
<223> OTHER INFORMATION: Synthetic nucleic acid

<400> SEQUENCE: 38 gcattatcc 9

<210> SEQ ID NO 39
<211> LENGTH: 9
<212> TYPE: RNA
<213> ORGANISM: Artificial sequence
<220> FEATURE:
<223> OTHER INFORMATION: Synthetic nucleic acid

<400> SEQUENCE: 39 gcauuaucc 9

-continued

```
<210> SEQ ID NO 40
<211> LENGTH: 10
<212> TYPE: DNA
<213> ORGANISM: Artificial sequence
<220> FEATURE:
<223> OTHER INFORMATION: Synthetic nucleic acid

<400> SEQUENCE: 40

gcattacccc                                                          10


<210> SEQ ID NO 41
<211> LENGTH: 10
<212> TYPE: RNA
<213> ORGANISM: Artificial sequence
<220> FEATURE:
<223> OTHER INFORMATION: Synthetic nucleic acid

<400> SEQUENCE: 41

gcauuacccc                                                          10


<210> SEQ ID NO 42
<211> LENGTH: 10
<212> TYPE: RNA
<213> ORGANISM: Artificial sequence
<220> FEATURE:
<223> OTHER INFORMATION: Synthetic nucleic acid

<400> SEQUENCE: 42

cuuuacaaaa                                                          10


<210> SEQ ID NO 43
<211> LENGTH: 9
<212> TYPE: DNA
<213> ORGANISM: Artificial sequence
<220> FEATURE:
<223> OTHER INFORMATION: Synthetic nucleic acid

<400> SEQUENCE: 43

ctttacaaa                                                            9
```

VIRAL RNA SEGMENTS AS IMMUNOMODULATORY AGENTS AND VACCINE COMPONENTS

This application is a national phase application under 35 U.S.C. § 371 of International Application No. PCT/US2015/049167, filed Sep. 9, 2015, which claims benefit of priority to U.S. Provisional Application Ser. No. 62/051,727, filed Sep. 17, 2014, the entire contents of each of the above-referenced disclosures are hereby incorporated by reference.

This invention was made with government support under Grant No. AI058740 awarded by the Institutes of Health and Merit Review Grant I01BX000207 awarded by the Department of Veterans Affairs. The government has certain rights in the invention.

Pursuant to 37 C.F.R. 1.821(c), a sequence listing is submitted herewith as an ASCII compliant text file named "IOWAP0117US_ST25.txt", created on Mar. 9, 2017 and having a size of 49 kilobytes. The content of the aforementioned file is hereby incorporated by reference in its entirety.

BACKGROUND

I. Field

The present disclosure relates generally to the fields of molecular biology and virology. More particularly, it concerns methods and compositions to treat inflammatory conditions, in particular those resulting from pathologic T-cell activation. It also relates to improved vaccine formulations and gene therapy methods.

II. Description of Related Art

Hepatitis C virus (HCV) infects more than 120 million people worldwide and is a leading cause of liver disease (Lavanchy 2009 and Rehermann 2009). Spontaneous clearance of HCV infection occurs in 20% to 40% of infected individuals, and is clearance is associated with sustained CD4+ and CD8+ T cell responses (Shoukry et al., 2003, Grakoui et al., 2003, Thimme et al., 2002, Cox et al., 2005, Thimme et al., 2001 and Lauer et al., 2004). Nevertheless, approximately 70% of infected individuals develop chronic viremia that can lead to cirrhosis and hepatocellular carcinoma (Rehermann 2009 and Li and Lemon 2013). One of the hallmarks of chronic HCV infection is an impaired HCV-specific T cell response and delayed onset of HCV-specific humoral and cellular immune responses (Cox et al., 2005, Netski et al., 2005, Chen et al., 1999, Park et al., 2013, Bowen and Walker 2005, Wedemeyer et al., 2002 and Gruener et al., 2001). HCV-specific intrahepatic T cells are associated with a low viral load and are functionally impaired during chronic HCV infection (Spangenberg et al., 2005 and Freeman et al., 2003). In addition, HCV infection is associated with reduced T cell activation (Rehermann 2009, Park et al., 2013 and Rehermann 2007), although the underlying mechanisms for this effect are not clear.

One important component for an effective adaptive immune response is the activation of CD4+ and CD8+ T cells (Medzhitov and Janeway 1998). Numerous factors appear to contribute to the blunted T cell response during HCV infection, including persistent and high antigenic viral load leading to expression of co-inhibitory receptors that result in T cell exhaustion (Radziewicz 2007 and Urbani et al., 2008), expansion of regulatory T cells, the selection of immune escape mutants (Cox et al., 2005, Netski et al., 2005 and Soderholm and Sallberg 2006), and the expression of immune-suppressive cytokines (Terilli and Cox, 2013; Liang, 2013).

HCV replicates primarily in hepatocytes and infection leads to a high plasma viral load (median value approximately $3.5\times10^5$ genome copies/mL) (Schijman et al., 2004 and Matthewsw-Greer et al., 2001). Infected hepatocytes secrete viral particles and extracellular vesicles containing viral RNA and E2 protein (Ramakrishnaiah et al., 2013, Cosset and Dreux 2014 and Masciopinto et al., 2004) which are capable of interacting with and modulating immune cell function (Dreux et al., 2012, Serti et al., 2011 and Tu et al., 2013). In addition, viral RNA is found in T and B lymphocytes of infected individuals (Schmidt et al., 1997, Wang et al., 1992, Fornasieri et al., 2000, Zignego et al., 2007), and the high concentration of HCV RNA containing particles in plasma result in abundant interactions between HCV RNA and proteins with lymphocytes.

It has been reported that the human Pegivirus (HPgV; formally called hepatitis G virus/GB virus C) is associated with a reduction in activation and proliferation of T cells in vivo (Bhattarai et al., 2012, Stapleton et al., 2011, Berzsenyi et al., 2011, Stapleton et al., 2009, Maidana-Giret et al., 2009, Nattermann et al., 2003 and Schwarze-Zander et al., 2010). HPgV particles inhibit T cell activation in vitro by inhibiting lymphocyte-specific tyrosine kinase (Lck), one important and proximal component of the T cell receptor (TCR) signaling pathway (Bhattarai et al., 2013, Bhattarai and Stapleton 2012 and Bhattrarai et al., 2012). A conserved motif within GBV-C envelope protein (E2) that is a predicted Lck substrate site is sufficient for inhibition, and mutation of the conserved tyrosine to alanine reverse the inhibition of T cell activation (Bhattarai et al., 2013, Bhattarai and Stapleton 2012 and Bhattrarai et al., 2012). Since HPgV is a closely related human virus to HCV, the HCV E2 protein sequence was examined and conserved motifs predicted to be Lck substrates were found.

HIV infection is associated with chronic immunoactivation that contributes to HIV mediated immune dysfunction, and immune activation facilitates HIV replication and pathogenesis (Grossman et al., 2006; Hazenberg et al., 2003). Although combination antiretroviral therapy (cART) suppresses HIV plasma viral load (VL), the level of immune activation markers generally do not return to levels observed in HIV-uninfected individuals (Hunt et al., 2008; Vinikoor et al., 2013). In addition, persistent immune activation observed in HIV-treated individuals has been reported to be associated with a reduced response to HIV therapy (Deeks et al., 2004; Hunt et al., 2003). Among HIV-infected subjects, HPgV coinfection is associated reduced immune activation independent of HIV VL or cART (Bhattarai et al., 2012b; Maidana-Giret et al., 2009; Stapleton et al., 2012), suggesting that GBV-C infection alters immune activation pathways. Since HPgV replication in vitro is reduced by T cell activation (Rydze et al., 2012), the development of mechanisms to inhibit immune activation is beneficial for the virus. Understanding mechanisms by which HPgV reduces chronic immune activation in HIV-infected subjects can provide approaches to treat HIV infection and HIV associated chronic immune activation. Indeed, by interfering with T cell activation pathways, many viruses increase the likelihood that it will cause persistent infection. Furthermore, by interfering with antigen presentation this impairs the ability to elicit memory T and B cell responses or high titers of antibodies.

SUMMARY

Thus, in accordance with the present disclosure, there is provided a method of inhibiting immune cell activation comprising administering to a mammalian subject in need thereof a viral RNA segment comprising a T cell immune-inhibitory domain. The viral RNA segment may comprise about 16, 17, 18, 19, 20, 21, 22, 23, 24, 25, 30, 35, 40, 45, 50, 75, 100, 150, 175, 200, 225, 250, 300, 400 or 500 consecutive bases of the T cell immune-inhibitory domain. The viral RNA segment may encode HCV E2 sequences, GBV-C E2 sequences, YFV envelope protein or HIV gp41 or gp120/160 sequences. The viral RNA segment may further encode non-HCV E2 sequences, non-GBV-C E2 sequences, non-YFV env sequences or non-HIV gp41 sequences. The T cell may be a helper T cell suppressor T cell, or a killer T cell. The subject may be a human or a non-human mammal. The immune cell activation may in particular be T cell activation or T cell receptor signaling.

Administering may comprise intravenous, intra-arterial, oral, subcutaneous, topical or intraperitoneal administration. The method may further comprise administering a second anti-inflammatory agent, such as a steroid or a COX-2 inhibitor. The second anti-inflammatory agent may be contacted prior to or after said viral RNA segment, or at the same time as said viral RNA segment. The viral RNA segment may be provided in combination with gene therapy. The viral RNA segment may comprise at least one non-natural base. The viral RNA segment may comprise a Dicer substrate.

The viral RNA segment may be administered at 0.1-500 mg/kg/d. The viral RNA segment may be administered daily or weekly, such as daily for 7 days, 2 weeks, 3 weeks, 4 weeks, one month, 6 weeks, 8 weeks, two months, 12 weeks, or 3 months, or weekly for 2 weeks, 3 weeks, 4 weeks, 6 weeks, 8 weeks, 10 weeks, or 12 weeks. The viral RNA segment may be derived from Human Immunodeficiency Virus envelope gp41 or gp120/160, Yellow Fever Virus envelope protein, Bovine Viral Diarrhea Virus envelope protein, Classical Swine Fever Virus envelope protein, influenza envelope protein, Dengue Virus envelope protein, West Nile Virus envelope protein, and Japanese Encephalitis Virus envelope protein.

In another embodiment, there is provided a composition comprising a viral RNA segment comprising a T cell immune-inhibitory domain, formulated with a pharmaceutically acceptable carrier buffer or diluent. The viral RNA segment may comprise about 10, 11, 12, 13, 14, 15, 16, 17, 18, 19, 20, 21, 22, 23, 24, 25, 27, 30, 35, 40, 45, 50, 51, 75, 100 consecutive bases of the native viral genome from which it is derived. The viral RNA segment may be about 10, 11, 12, 13, 14, 15, 16, 17, 18, 19, 20, 21, 22, 23, 24, 25, 27, 30, 35, 40, 45, 50, 51, 75, 100, 125, 150, 175, 200, 225, 250, 275, 300, 400 or 500 bases in length. The viral RNA segment may be fused to a non-viral sequence. The composition may be formulated for pharmaceutical administration, such as topical, cutaneous, subcutaneous, alimentrary or parenteral administration.

In yet another embodiment, there is provided a method of inducing an immune response in a mammalian subject comprising administering to said subject a viral RNA segment wherein said viral RNA segment comprises one or more modified T cell immune-inhibitory domains. The modified site may comprise Dicer substrate. The RNA virus may be from the Reoviridae, Atroviridae, Caliciviridae, Hepeviridae, Picornaviridae, Togaviridae, Flaviviridae, Coronaviridae, Orthomyxoviridae, Arenaviridae, Bunyaviridae, Paramyxoviridae, Filoviridae, Rabdoviridae, or Retroviridae family. The RNA virus may be GBV-C, Hepatitis C Virus, Human Immunodeficiency Virus, influenza virus, Dengue Virus, West Nile Virus, Japanese Encephalitis Virus, Bovine Viral Diarrhea Virus, Classical Swine Fever Virus or Yellow Fever Virus. The viral RNA segment may be free from other viral sequences.

The viral RNA segment may be delivered via expression from an expression vector, such as a viral expression vector. The viral RNA segment may be comprised in lipid vehicle or nanoparticle. The viral RNA segment may be administered with a second viral RNA segment from a distinct serotype or strain of said virus. The viral RNA segment may be administered more than once. The viral RNA segment may be formulated with an adjuvant. The viral RNA segment may comprise a modification to an immunomodulatory domain in a viral glycoprotein. The viral RNA segment may be from a HCV E2-coding region, and HIV gp41- or gp120/160-coding region or a GBV-C E2-coding region. The site comprises a dicer substrate. The subject may be a human subject or a non-human animal subject.

Also provided is a vaccine comprising a viral RNA segment having a modification in a T cell immune-inhibitory domain. The modification may comprise a deleted segment or a mutated segment. The viral RNA segment may comprise about 10, 11, 12, 13, 14, 15, 16, 17, 18, 19, 20, 21, 22, 23, 24, 25, 27, 30, 35, 40, 45, 50, 51, 75, or 100 consecutive residues of the native viral genome from which it is derived. The viral RNA segment may be about 10, 11, 12, 13, 14, 15, 16, 17, 18, 19, 20, 21, 22, 23, 24, 25, 27, 30, 35, 40, 45, 50, 51, 75, 100, 125, 150, 175, 200, 219 or 250 bases in length. The viral RNA segment may be fused to a non-viral sequence. The vaccine may be formulated with an adjuvant. The viral RNA segment may be from an HCV E2-, YFV Env, HIV 41-, HIV pg120/160 or GBV-C E2-coding region.

Another embodiment comprises a method of performing gene transfer into a subject comprising administering to said subject an expression cassette comprising a heterologous gene segment under the control of a promoter operable in cells of said subject, wherein said expression cassette further comprises a viral RNA segment comprising a T cell immune-inhibitory domain. The viral RNA segment may comprise about 10, 11, 12, 13, 14, 15, 16, 17, 18, 19, 20, 21, 22, 23, 24, 25, 27, 30, 35, 40, 45, 50, 51, 75, 100 consecutive bases of the native viral genome from which it is derived. The viral RNA segment may be about 10, 11, 12, 13, 14, 15, 16, 17, 18, 19, 20, 21, 22, 23, 24, 25, 27, 30, 35, 40, 45, 50, 51, 75, 100, 125, 150, 175, 200, 225, 250, 275, 300, 400 or 500 bases in length. The viral RNA segment may be fused to a non-viral sequence. The composition may be formulated for pharmaceutical administration, such as topical, cutaneous, subcutaneous, alimentrary or parenteral administration.

In yet another embodiment, there is provided a method of inducing an immune response in a mammalian subject comprising administering to said subject a viral RNA segment wherein said viral RNA segment comprises one or more modified T cell immune-inhibitory domains. The modified site may comprise Dicer substrate. The RNA virus may be from the Reoviridae, Atroviridae, Caliciviridae, Hepeviridae, Picornaviridae, Togaviridae, Flaviviridae, Coronaviridae, Orthomyxoviridae, Arenaviridae, Bunyaviridae, Paramyxoviridae, Filoviridae, Rabdoviridae, or Retroviridae family. The RNA virus may be GBV-C, Hepatitis C Virus, Human Immunodeficiency Virus, influenza virus, Dengue Virus, West Nile Virus, Japanese Encephalitis Virus, Bovine Viral Diarrhea Virus, Classical Swine Fever Virus or Yellow Fever Virus. The viral RNA segment may be free from other viral sequences. The viral RNA segment may comprise a Dicer substrate.

In yet another embodiment, the target of the HCV RNA has been identified as a novel T cell immune modulator. This target is a phosphatase (protein tyrosine phosphatase receptor type E or epsilon, abbreviated PTPRE). PTPRE is reduced by both HCV RNA envelope E2 and YFV envelope RNA, and complete knockdown of this gene renders the cells non-viable. However, HCV and YFV RNA does not have complete complementarity, and thus merely reduces PTPRE protein expression, which in turn reduces T cell activation and functional responses. Since this partial T cell inhibition does not lead to profound immune deficiency, but does impair T cell responses, PTPRE is identified as a novel target for immune suppressant therapy. Threus, partial inhibition using nucleic acid-based methodologies (miRNA, siRNA, shRNA, antisense, etc.) can be achieved using only routine experimentation, i.e., starting with molecules having complete or high complementarity, and making sequential changes to reduce complementarity, thereby adjusting the level of inhibition such that immune function is blunted, but not completely eliminated (i.e., rendering the cells non-viable). It is expected that in contexts involving inhibitory RNAs that rely on a "seed sequence" for recognition, the seed sequence will remain completely or highly complementary, with other sequences being reduced in complementarity. For example, seed sequence complementarity might be greater than about 80%, while other regions would be 20-60% complementary.

Also provided are pharmaceutical compositions comprising a nucleic acid having the sequence:

```
                                        (SEQ ID NO: 3)
CTCACGCCAAGGTGCCTGATCGACTACCCCTACAGGCTCTGGCATTATCC,
                                        (SEQ ID NO: 4)
CTCACGCCAAGGTGCCTGATCGACTACCCCTACAGGCTCTGGCATTACCCC
or
                                        (SEQ ID NO: 5)
GACAACAACCTTTACAAACTACATGGT.
```

The pharmaceutical composition may also comprise a nucleic acid sequence selected from GCATTATCC (SEQ ID NO: 38), GCAUUAUCC (SEQ ID NO: 39), GCATTACCCC (SEQ ID NO: 40), GCAUUACCCC (SEQ ID NO: 41), CUUUACAAAA (SEQ ID NO: 42), or CTTTACAAA (SEQ ID NO: 43), wherein said nucleic acid consists essentially of at least about 20 base pairs and no more than about 55 base pairs. Specific lengths include 22, 27 and 51 nucleotides.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are recited, it is understood that the steps are not required to be performed in the particular order recited unless one of skill in the art is not be able to practice the method in a different order.

Other objects, features, and advantages of the present disclosure will become apparent from the following detailed description. It should be understood, however, that the detailed description and the specific examples, while indicating some embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 2C). Analysis of CFSE positive serum EV (FIG. 2D) and uptake of $CFSE^+$ EV by primary human T cells (FIG. 2E) as determined by flow cytometry. HCV RNA was detected using RT-PCR in EVs from HCV-positive serum, and in human PBMCs incubated with HCV-positive but not negative serum (FIG. 2F). HCV RNA US=unstimulated cells. MFI=mean fluorescent intensity. Data represent the average of three technical replicates with standard deviation and each study was independently performed three times using different donors with similar results. $*P<0.05$; $**P<0.01$.

FIG. 4B (603-619=SEQ ID NO: 6)), the zeta-chain-associated protein kinase (ZAP)-70 (Y319; FIG. 4C) and linker for activation of T cells (LAT, Y226; FIG. 4D (603-619=SEQ ID NO: 6)) was analyzed in HCV E2 expressing Jurkat cells compared to the controls (JC) following TCR activation using anti-CD3. IL-2 released in truncated or substitution mutant HCV E2 proteins expressing Jurkat cells are shown in FIG. 4E. The amino acid numbers relate to their location on the HCV polyprotein. Phospho-blots for Lck, ZAP-70 and LAT was performed at least three times with consistent results. Data represent the average of three technical replicates. The standard deviation is shown. All studies were repeated at least three times with consistent results. *P<0.01, ns=not significant.

FIG. 5D demonstrates the partial sequence of the plasmid (pCR2.1) and HCV E2 RNA amplification product, followed by the oligonucleotide linker sequence (SEQ ID NO: 10). Data represent the average of three technical replicates. The standard deviation is shown. Each study was repeated at least three times with consistent results. *P<0.01; ns=not significant.

FIGS. 12A-E. HCVcc and HCVpp inhibits TCR signaling in purified CD3+ T cells.

FIGS. 13A-D. Expression of HCV and effect of E2 on the activation of TCR signaling molecules (603-619=SEQ ID NO: 6).

FIGS. 14A-B. Effect of HCV E2 protein on Lck regulatory proteins.

FIGS. 15A-B. Expression of GFP and HCV E2 proteins in Jurkat cells.

FIGS. 29A-C. YFV TCR inhibition. YFV RNA sequence aligns with two PTPRE 3'utr sequences (FIG. 29A; Site 1—PTPRE 3'UTR=SEQ ID NO: 18, YF Env=SEQ ID NO: 19; Site 2—PTPRE 3'UTR=SEQ ID NO: 20, YF Env=SEQ ID NO: 21). Mutations show that mutation of 2 nucleosides in the seed sequence (UUUACAAAA; SEQ ID NO: 22) restored TCR signaling (FIG. 29B; Y274=SEQ ID NO: 23; Y274F=SEQ ID NO: 24; Y274A=SEQ ID NO: 25; Y274G=SEQ ID NO: 26). YFV, but not mumps virus infection reduced PTPRE protein levels in MRC-5 cells (FIG. 29C).

DESCRIPTION OF ILLUSTRATIVE EMBODIMENTS

Figure 1:
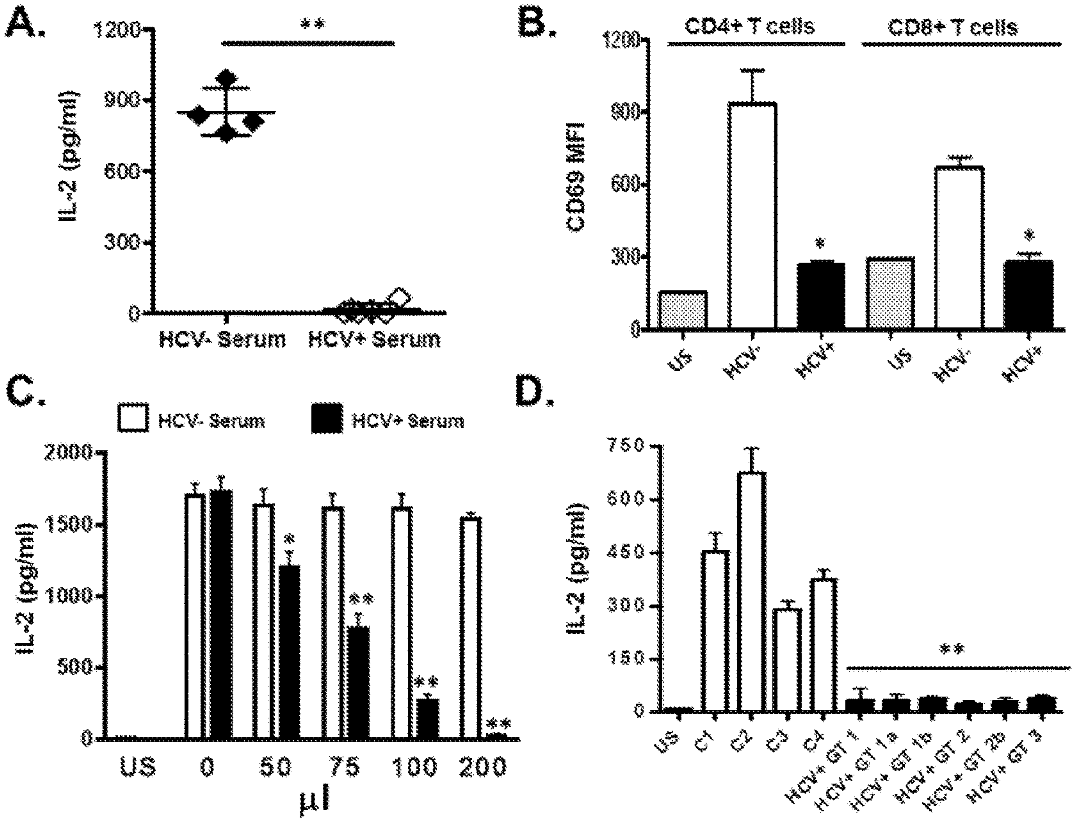
FIGS. 1A-D. HCV serum particles inhibit T cell receptor (TCR) signaling in primary human T lymphocytes. Healthy donor PBMCs were incubated with serum obtained from HCV positive (HCV+) humans infected with various genotypes and subtypes (GT; 1, 1a, 1b, 2, 2b, and 3) or HCV negative control serum (C1-C4) and IL-2 release (FIG. 1A) and CD69 surface expression (FIG. 1B) were measured following TCR stimulation with anti-CD3/CD28. CD69 MFI represents the average of four HCV negative and six HCV-positive sera samples. The standard deviation is shown. TCR-induced IL-2 release by human PBMCs incubated with various doses of pooled HCV positive or HCV negative serum (FIG. 1C). IL-2 release by purified primary human CD3+ T cells incubated with HCV-positive sera from genotypes (GT; 1, 1a, 1b, 2, 2b, and 3) or HCV negative serum (C1-C4) (FIG. 1D). US=unstimulated cells. MFI=mean fluorescent intensity. Data represent the average of three technical replicates. The standard deviation is shown, and each study was independently performed three times using different donors with similar results. $*P<0.05$; $**P<0.01$.

Previously, potential mechanisms by which GBV-C and other RNA viruses reduce immunoactivation was examined. A novel viral mechanism that inhibits T cell receptor (TCR) signaling via competition for the lymphocyte-specific protein tyrosine kinase (Lck) mediated by the persistent human Pegivirus GBV-C envelope glycoprotein E2 was found. Additional data showing that hepatitis C virus (HCV) and yellow fever virus (YFV, 17D strain) similarly inhibit T cell activation, and both the envelope glycoprotein and the envelope coding region of both of these viruses interfere with T cell activation was provided. Highly conserved RNA sequences in both viruses have been identified that are predicted to be processed into a microRNA. These sequences target PTPRE, or Receptor-type tyrosine-protein phosphatase epsilon, an enzyme that in humans is encoded by the PTPRE gene. The protein encoded by this gene is a member of the protein tyrosine phosphatase (PTP) family. PTPs are known to be signaling molecules that regulate a variety of cellular processes including cell growth, differentiation, mitotic cycle, and oncogenic transformation. Two alternatively spliced transcript variants of this gene have been reported, one of which encodes a receptor-type PTP that possesses a short extracellular domain, a single transmembrane region, and two tandem intracytoplasmic catalytic domains; another one encodes a PTP that contains a distinct hydrophilic N-terminus, and thus represents a non-receptor-type isoform of this PTP. Studies of the similar gene in mice suggested the regulatory roles of this PTP in RAS related signal transduction pathways, cytokines induced SATA signaling, as well as the activation of voltage-gated K+ channels.

While the Lck kinase is involved in these studies of GBV-C and HCV, additional T cell inhibitory signaling molecules are also involved for HCV. Furthermore, bioinformatic predictions for other human pathogens are provided showing that they share this immunomodulatory feature, including west Nile virus (WNV), dengue viruses (DENV), Japanese encephalitis virus (JEV), Influenza A and B, and HIV. A major problem with subunit vaccines for many of these viruses is that they are poor immunogens and elicit low levels of antibody and poor memory responses. Thus, it has been posited that by identification of the T cell interacting domains of the envelope proteins, followed by mutation of important amino acids needed to interfere with T and B cell responses, they can generate more potent vaccines with improved longevity of protection.

GBV-C and the related HCV are cytoplasmic human RNA viruses that cause persistent infection. GBV-C modulates global T cell activation as determined by measurement of surface markers upregulated on CD4+ and CD8+ T cells following activation (Nattermann et al., 2003; Maidana et al., 2009; Xiang et al., 2004; Xiang et al., 2006; Schwarze-Zander et al., 2010; Stapleton et al., 2012). The effect is modest, and GBV-C infected humans are not characterized by side effects of immunosuppression (reviewed in Bhattarai & Stapleton, 2012). In contrast, HCV has been reported to be associated with an increased susceptibility to other infections, particularly HBV, bacterial infections, and schistosomiasis (reviewed in Hahn, 2003). Although anti-HCV envelope antibodies can protect chimpanzees from infection (Farci et al., 1996), immune responses to HCV envelope are weak (Fournillier et al., 2001; Cerny and Chisari, 1999). Several reasons for this have been proposed including virion or E2 association with lipids, heavy glycosylation, and marked antigenic variation (Fournillier et al., 2001).

Numerous clinical studies find an association between GBV-C infection and reduced levels of T and B cell activation (Bowen, and Walker, 2005; Lauer and Walker, 2001; Kanto et al., 1999; Krishnada et al., 2010; Kobayashi et al., 1998; Semmo et al., 2005; Eckels et al., 1999; Serti et al., 2011; Doganiuc et al., 2003; Tomova et al., 2009; Masciopinto et al., 2004). Expression of the GBV-C E2 protein in a CD4+ T cell line resulted in a block in IL-2 release, and upregulation of activation markers CD69 and CD25 following stimulation through the T cell receptor (TCR) (Bhattarai et al., 2012b). Furthermore, addition of recombinant E2 to primary human CD4 and CD8 cells blocked these three measures of TCR signaling (Bhattarai et al., 2012b).

While GBV-C replicates in T and B lymphocytes (Xiang et al., 2000; George et al., 2006), a very low proportion of lymphocytes in peripheral blood are infected (on average, <1%). Thus, infection alone is unlikely to cause the global reduction in TCR-mediated activation. It has been found that serum microvesicles obtained from GBV-C-infected people block T cell activation compared to serum microvesicles from GBV-C uninfected. It has further been reported that CD4+ T cell lines expressing E2 protein produce exosomes containing E2 which reduced T cell activation (Bhattarai et al., 2013). Previous reports indicate that HCV produces exosomes, and that E2 is incorporated in these via its interactions with the E2 receptor CD81 (Masciopinto et al., 2004), a common component of exosomes.

It is disclosed herein that HCV particles directly interfere with T cell receptor (TCR) signaling in human T cells, even in absence of viral replication. HCV particles obtained from either serum of infected humans or cell-culture inhibited TCR signaling. The inhibition of TCR signaling is mediated at least in part by the HCV envelope (E2) coding RNA and protein. HCV E2 RNA inhibited proximal TCR signaling by reducing activation of lymphocyte-specific tyrosine kinase (Lck). HCV E2 protein inhibited distal TCR signaling by reducing nuclear translocation of activated NFAT. Conserved nucleotide sequences in the RNA region coding for HCV E2 were involved in proximal TCR signaling inhibition, while inhibition of distal TCR signaling involved Lck mediated phosphorylation of a conserved tyrosine in HCV E2 protein (Y613). Both proximal and distal TCR signaling defects were reversed by mutation of the nucleotides in E2 RNA or Y613 in E2 protein. These data indicate that HCV particles can directly interfere with TCR signaling.

I. VIRUSES

GBV-C envelope glycoprotein contains binding sites and substrate sites that compete with lymphocyte kinases leading to impaired activation. Hepatitis C virus (HCV) and yellow fever virus (YFV) envelopes similarly impair lymphocyte activation. It suggested that this may explain the poor immunogenicity and memory responses to immunization with recombinant envelope proteins. Using these sites as immunosuppressive agents is therefore proposed. Further, by identification and mutation of these immunomodulatory sites, envelope glycoproteins will be more immunogenic and will induce improved memory T and B cell responses.

As such, the disclosure involves two aspects, both stemming from the identification of viral envelope sequences that inhibit T cell activation. These sequences can be used to reduce host immune responses in situations where such is desired, or they can be altered and then used in the context of improved vaccination to prevent, control or limit viral infection.

This will apply for all human and animal RNA viruses including vertebrate dsRNA viruses of the family Reoviridae, and ssRNA viruses of the families Atroviridae, Caliciviridae, HEV, Picornaviridae, Togaviridae, Flaviviridae, Coronaviridae, Orthomyxoviridae, Arenaviridae, Bunyaviridae, Paramyxoviridae, Filoviridae, Rabdoviridae, and Retroviridae.

A. Hepatitis C Virus

HCV primarily replicates in the hepatocyte (Major et al., 1997), but is also found in association with a variety of peripheral blood cells (PBC's) (Major et al., 1997; Schmidt et al., 1997). Although controversial, it appears that HCV replicates to some extent in PBCs, and inefficient in vitro cultivation can be achieved in T- and B-cell lines (Major et al., 1997; Bartenschlager et al., 2000).

The mechanism by which HCV attaches and enters cells has not been clear. Two cellular surface receptors have been shown to interact with HCV or the HCV envelope glycoprotein E2 in vitro, leading to speculation that either may represent the HCV cellular receptor (Pileri et al., 1998; Monazahian et al., 1999; Agnello et al., 1999; Flint et al., 1999; Wuenschmann et al., 2000). It has been reported that recombinant HCV E2 binds to human CD81 (Pileri et al., 1998; Flint et al., 1999; Flint and Maidens et al., 1999; Hadlock et al., 2000; Owsianka et al., 2001; Flint and McKeating, 2000; Petracca et al., 2000; Patel et al., 2000). CD81 is a member of the tetraspanin superfamily of cell surface molecules, and is expressed on virtually all nucleated cells (Levy and Maecker, 1998). Initial studies suggested that E2 binding to CD81 may be responsible for the binding of HCV to target cells in vivo. However, although E2 has repeatedly been reported to bind CD81, only two studies presented evidence that HCV particles derived from human serum bind to this surface molecule (Pileri et al., 1998; Hadlock et al., 2000).

It has been reported that, although HCV E2 binds specifically to CD81 (Wuenschmann et al., 2000), the binding of HCV particles purified from plasma was not inhibited by soluble CD81, and the extent of virus binding correlated with the level of LDLr expression (Wuenschmann et al., 2000). Additional lines of evidence argue that CD81 is not the HCV receptor. HCV E2 has a higher affinity for marmoset CD81 than human CD81, yet marmosets are not susceptible to HCV. The affinity for HCV E2 to CD81 was found to be significantly lower than predicted for a true viral receptor (Petracca et al., 2000). Using an RT-PCR based detection method, plasma-derived HCV and HCV E2 bound to U937 subcloned cells that lack expression of CD81 (Hamaia and Allain, 2001). These data suggest that CD81 is not the primary cell receptor for HCV.

Nevertheless, HCV E2 does interact with CD81, and the E2 regions involved in CD81 binding are highly conserved (Pileri et al., 1998; Flint et al., 1999; Flint and Maidens et al., 1999; Hadlock et al., 2000; Owsianka et al., 2001; Flint and McKeating, 2000; Petracca et al., 2000; Patel et al., 2000)), suggesting a functional role for CD81-E2 interactions in HCV replication (Pileri et al., 1998; Flint et al., 1999; Flint and Maidens et al., 1999; Hadlock et al., 2000; Owsianka et al., 2001; Flint and McKeating, 2000). The extremely low density of HCV found in gradient centrifugation of infectious serum suggested an association with VLDL and LDL (Hijikata et al., 1993; Bradley et al., 1991; Prince et al., 1996). Infectious virus was found at the same densities as VLDL and LDL and coprecipitated with LDL (Monazahian et al., 1999; Bradley et al., 1991; Prince et al., 1996; Thomssen and Thiele, 1993; Xiang et al., 1998). Subsequent studies (Monazahian et al., 1999; Bradley et al., 1991; Prince et al. 1996; Xiang et al., 1998) reported an interaction between HCV or HCV-LDL complexes with the low density lipoprotein receptor (LDLr) (Wuenschmann et al., 2000; Prince et al., 1996; Thomssen and Thiele, 1993; Xiang et al., 1998; Thomssen et al., 1992).

HCV present in the plasma of infected people has also been reported to interact with very-low-density (VLDL) and low-density lipoproteins (LDL). The liver synthesizes VLDL which consists of triaglycerols, cholesterol, phospholipids and the apoprotein apoB-100, VLDL's released into the blood, where it acquires additional lipoproteins $C_{II}$ and apoE from high-density lipoproteins (HDL). VLDL is digested by Lipoprotein Lipase (LPL), an enzyme found attached to capillary endothelial cells, to form intermediate density lipoproteins (IDL) and LDL, and apoB-100 is the only remaining apoprotein in LDL. The low-density lipoprotein receptor (LDLr) recognizes both apoE and apoB-100 and can therefore bind VLDL, IDL and chylomicron remnants in addition to LDL. (Marks et al., 1996).

HCV-RNA containing material in serum, presumably virus particles, separate into very low density particles (<1.06 g/cm$^3$) by gradient sedimentation, suggesting that HCV associates with VLDL and LDL (Monazahian et al., 1999; Thomssen et al., 1993; Xiang et al., 1998; Prince et al., 1996; Bradley et al., 1991). In addition, particles with densities of 1.11-1.18 g/cm$^3$ have been described (Xiang et al., 1998; Prince et al., 1996; Bradley et al., 1991; Hijikata et al., 1993). Chimpanzee infectivity studies reported that the very low density HCV particles were highly infectious, whereas the particles of higher density were not infectious (Bradley, 2000). HCV and GBV-C have different particle types, and that the functional effects of E2 protein and HCV RNA may vary between particle types (Monazahian et al., 1999; Xiang et al., 1998; Prince et al., 1996; Bradley et al., 1991). Thomssen et al. (1993) showed that HCV coprecipitated with LDL and demonstrated an interaction of HCV or HCV-LDL complexes with the LDLr (Wuenschmann et al., 2000; Thomssen et al., 1993; Xiang et al., 1998; Prince et al., 1996; Thomssen et al., 1992).

Monazahian et al. (1999) reported that expression of recombinant human LDLr in murine cells lacking human CD81 confirmed binding of HCV to these cells, and Agnello et al. (1999) reported that HCV bound to and entered fibroblasts containing LDLr, but not LDLr deficient fibroblasts, using an in situ hybridization method. Using flow cytometry, it was reported that plasma-derived HCV bound to cells expressing LDLr, but not to cells lacking the LDLr (Wuenschmann et al., 2000). No interactions between viral envelope proteins (E1 or E2) and the LDL receptor have been reported (Wuenschmann et al., 2000). Monazahian et al. (1999) found that in vitro translated HCV E1 and E2 proteins, labeled with $^{35}$S-methionine co-precipitated with VLDL, LDL and HDL (Monazahian et al., 2000).

HCV E2 is the outer protein of the viral envelope and may participate in the binding of viruses to the target cells. The protein starts at amino acid 394 of the HCV polyprotein, and extends to amino acid 747. It has a hypervariable region at the amino terminus of the protein, and the carboxy terminus includes a transmembrane domain.

Due to the deficiencies in the prior art, there remains a need for more effective treatments to lower LDL levels in a subject. There also remains a need for new and useful methods of reducing, controlling or preventing HCV infection in a subject. The presently claimed disclosure overcomes the deficiencies in the prior art by disclosing new and useful methods for reducing LDL levels in a subject. The present disclosure also discloses new and useful methods of identifying HCV inhibitors and methods of treating HCV infection.

The viral genomic sequence of HCV is known, as are methods for obtaining the sequence. See, International Publication Nos. WO 89/04669; WO 90/11089; and WO 90/14436. Hepatitis C Virus (HCV) HCV is an enveloped virus containing a positive-sense single-stranded RNA genome of approximately 9.5 kb. The genomic sequence of HCV is approximately 9401 base pairs in length (SEQ ID NO: 1). The peptide sequence for HCV can be obtained from Genbank Accession No. M62321. The viral genome consists of a lengthy 5' untranslated region (UTR), a long open reading frame encoding a polyprotein precursor of approximately 3011 amino acids (SEQ ID NO: 2) and a short 3' UTR. The 5' UTR is a highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). The polyprotein precursor is cleaved by both host and viral proteases to yield mature viral structural and non-structural proteins. Viral structural proteins include a nucleocapsid core protein and two envelope glycoproteins, E1 and E2 (U.S. Pat. No. 6,326,151).

HCV utilizes the low density lipoprotein receptor (LDLr) for cell binding and entry (Wuenschmann et al., 2000; Monazahian et al., 1999; Agello et al., 1999). It has previously been indicated that the HCV envelope glycoprotein (HCV E2 glycoprotein) binds to the lipid moiety of human lipoproteins, and the lipid-virus complex uses the natural receptor for LDL to bind to cells. The HCV E2 glycoprotein starts at amino acid 394 of the HCV polyprotein, and extends to amino acid 747. It has a hypervariable region at the amino terminus of the protein, and the carboxy terminus includes a transmembrane domain. HCV enters the cell via endocytosis using the LDL receptor. HCV E2 glycoprotein interactions with LDL result not only in CD81-independent binding to cells (Wuenschmann et al., 2000), but also to enhancement in LDL binding and uptake by the cells.

B. Other Viruses

1. Yellow Fever Virus

Yellow fever is caused by the yellow fever virus, a 40 to 50 nm wide enveloped RNA virus belonging to the family Flaviviridae. The positive sense single-stranded RNA is approximately 11,000 nucleotides long and has a single open reading frame encoding a polyprotein. Host proteases cut this polyprotein into three structural (C, prM, E) and seven non-structural proteins (NS1, NS2A, NS2B, NS3, NS4A, NS4B, NS5); the enumeration corresponds to the decreased pH induces the fusion of the endosomal membrane with the virus envelope. Thus, the capsid reaches the cytosol, decays and releases the genome. Receptor binding as well as membrane fusion are catalyzed by the protein E, which changes its conformation at low pH, which causes a rearrangement of the 90 homodimers to 60 homotrimers.

After entering the host cells, the viral genome is replicated in the rough endoplasmic reticulum (ER) and in the so-called vesicle packets. At first, an immature form of the virus particle is produced inside the ER, whose M-protein is not yet cleaved to its mature form and is therefore denoted as prM (precursor M) and forms a complex with protein E. The immature particles are processed in the Golgi apparatus by the host protein furin, which cleaves prM to M. This releases E from the complex which can now take its place in the mature, infectious virion.

The yellow fever virus is mainly transmitted through the bite of the yellow fever mosquito *Aedes aegypti*, but other mosquitoes such as the "tiger mosquito" (*Aedes albopictus*) can also serve as a vector for the virus. Like other Arboviruses which are transmitted via mosquitoes, the yellow fever virus is taken up by a female mosquito which sucks the blood of an infected person or primate. Viruses reach the stomach of the mosquito, and if the virus concentration is high enough, the virions can infect epithelial cells and replicate there. From there they reach the haemocoel (the blood system of mosquitoes) and from there the salivary glands. When the mosquito next sucks blood, it injects its saliva into the wound, and thus the virus reaches the blood of the bitten person. There are also indications for transovarial and transstadial transmission of the yellow fever virus within *A. aegypti*, i.e., the transmission from a female mosquito to her eggs and then larvae. This infection of vectors without a previous blood meal seems to play a role in single, sudden breakouts of the disease.

2. HIV

HIV is a member of the genus Lentivirus, part of the family of Retroviridae. Lentiviruses have many morphologies and biological properties in common. Many species are infected by lentiviruses, which are characteristically responsible for long-duration illnesses with a long incubation period. Lentiviruses are transmitted as single-stranded, positive-sense, enveloped RNA viruses. Upon entry into the target cell, the viral RNA genome is converted (reverse transcribed) into double-stranded DNA by a virally encoded reverse transcriptase that is transported along with the viral genome in the virus particle. The resulting viral DNA is then imported into the cell nucleus and integrated into the cellular DNA by a virally encoded integrase and host co-factors. Once integrated, the virus may become latent, allowing the virus and its host cell to avoid detection by the immune system. Alternatively, the virus may be transcribed, producing new RNA genomes and viral proteins that are packaged and released from the cell as new virus particles that begin the replication cycle anew.

HIV infects vital cells in the human immune system such as helper T cells (specifically $CD4^+$ T cells), macrophages, and dendritic cells. HIV infection leads to low levels of $CD4^+$ T cells through a number of mechanisms including: apoptosis of uninfected bystander cells, direct viral killing of infected cells, and killing of infected $CD4^+$ T cells by CD8 cytotoxic lymphocytes that recognize infected cells. When $CD4^+$ T cell numbers decline below a certain level, cell-mediated immunity is lost, and the body becomes progressively more susceptible to opportunistic infections.

Two types of HIV have been characterized: HIV-1 and HIV-2. HIV-1 is the virus that was initially discovered and termed both LAV and HTLV-III. It is more virulent, more infective, and is the cause of the majority of HIV infections globally. The lower infectivity of HIV-2 compared to HIV-1 implies that fewer of those exposed to HIV-2 will be infected per exposure. Because of its relatively poor capacity for transmission, HIV-2 is largely confined to West Africa.

HIV is different in structure from other retroviruses. It is roughly spherical with a diameter of about 120 nm, around 60 times smaller than a red blood cell, yet large for a virus. It is composed of two copies of positive single-stranded RNA that codes for the virus's nine genes enclosed by a conical capsid composed of 2,000 copies of the viral protein p24. The single-stranded RNA is tightly bound to nucleocapsid proteins, p7, and enzymes needed for the development of the virion such as reverse transcriptase, proteases, ribonuclease and integrase. A matrix composed of the viral protein p17 surrounds the capsid ensuring the integrity of the virion particle.

This is, in turn, surrounded by the viral envelope that is composed of two layers of fatty molecules called phospholipids taken from the membrane of a human cell when a newly formed virus particle buds from the cell. Embedded in the viral envelope are proteins from the host cell and about 70 copies of a complex HIV protein that protrudes through the surface of the virus particle. This protein, known as Env, consists of a cap made of three molecules called glycoprotein (gp) 120, and a stem consisting of three gp41 molecules that anchor the structure into the viral envelope. This glycoprotein complex enables the virus to attach to and fuse with target cells to initiate the infectious cycle. Both these surface proteins, especially gp120, have been considered as targets of future treatments or vaccines against HIV.

The RNA genome consists of at least seven structural landmarks (LTR, TAR, RRE, PE, SLIP, CRS, and INS), and nine genes (gag, pol, and env, tat, rev, nef, vif, vpr, vpu, and sometimes a tenth tev, which is a fusion of tat env and rev), encoding 19 proteins. Three of these genes, gag, pol, and env, contain information needed to make the structural proteins for new virus particles. For example, env codes for a protein called gp160 that is broken down by a cellular protease to form gp120 and gp41. The six remaining genes, tat, rev, nef, vif, vpr, and vpu (or vpx in the case of HIV-2), are regulatory genes for proteins that control the ability of HIV to infect cells, produce new copies of virus (replicate), or cause disease.

The two Tat proteins (p16 and p14) are transcriptional trans activators for the LTR promoter acting by binding the TAR RNA element. The TAR may also be processed into microRNAs that regulate the apoptosis genes ERCC1 and IER3. The Rev protein (p19) is involved in shuttling RNAs from the nucleus and the cytoplasm by binding to the RRE RNA element. The Vif protein (p23) suppresses the action of APOBEC3G (a cell protein that deaminates DNA:RNA hybrids and/or interferes with the Pol protein). The Vpr protein (p14) arrests cell division at G2/M. The Nef protein (p27) down-regulates CD4 (the major viral receptor), as well as the MHC class I and class II molecules.

Nef also interacts with SH3 domains. The Vpu protein (p16) influences the release of new virus particles from infected cells. The ends of each strand of HIV RNA contain an RNA sequence called the long terminal repeat (LTR).

Regions in the LTR act as switches to control production of new viruses and can be triggered by proteins from either HIV or the host cell. The Psi element is involved in viral genome packaging and recognized by Gag and Rev proteins. The SLIP element (TTTTTT) is involved in the frameshift in the Gag-Pol reading frame to make functional Pol.

HIV differs from many viruses in that it has very high genetic variability. This diversity is a result of its fast replication cycle, with the generation of about $10^{10}$ virions every day, coupled with a high mutation rate of approximately $3\times10^{-5}$ per nucleotide base per cycle of replication and recombinogenic properties of reverse transcriptase. This complex scenario leads to the generation of many variants of HIV in a single infected patient in the course of one day. This variability is compounded when a single cell is simultaneously infected by two or more different strains of HIV. When simultaneous infection occurs, the genome of progeny virions may be composed of RNA strands from two different strains. This hybrid virion then infects a new cell where it undergoes replication. As this happens, the reverse transcriptase, by jumping back and forth between the two different RNA templates, will generate a newly synthesized retroviral DNA sequence that is a recombinant between the two parental genomes. This recombination is evident when it occurs between subtypes.

Three groups of HIV-1 have been identified on the basis of differences in the envelope (env) region: M, N, and O. Group M is the major type and is subdivided into eight subtypes (or clades), based on the whole genome, which are geographically distinct. The most prevalent are subtypes B (found mainly in North America and Europe), A and D (found mainly in Africa), and C (found mainly in Africa and Asia); these subtypes form branches in the phylogenetic tree representing the lineage of the M group of HIV-1. Coinfection with distinct subtypes gives rise to circulating recombinant forms (CRFs). In 2000, the last year in which an analysis of global subtype prevalence was made, 47.2% of infections worldwide were of subtype C, 26.7% were of subtype A/CRF02_AG, 12.3% were of subtype B, 5.3% were of subtype D, 3.2% were of CRF_AE, and the remaining 5.3% were composed of other subtypes and CRFs. Most HIV-1 research is focused on subtype B; few laboratories focus on the other subtypes. The existence of a fourth group, "P", has been hypothesised based on a virus isolated in 2009. The strain is apparently derived from gorilla SIV (SIVgor), first isolated from western lowland gorillas in 2006. The genetic sequence of HIV-2 is only partially homologous to HIV-1 and more closely resembles that of SIVsmm.

3. Influenza

The influenza virus is an RNA virus of the family Orthomyxoviridae, which comprises five genera: Influenzavirus A, Influenzavirus B, Influenzavirus C, Isavirus and Thogotovirus. The Influenzavirus A genus has one species, influenza A virus. Wild aquatic birds are the natural hosts for a large variety of influenza A. Sometimes viruses are transmitted to other species and may then cause devastating outbreaks in domestic poultry or give rise to human influenza pandemics. The type A viruses are significant virulent human pathogens among the three influenza types and cause severe disease. The influenza A virus can be subdivided into different subtypes based on the antibody response to these viruses.

Influenzaviruses A, B and C are very similar in structure. The virus particle is 80-120 nanometers in diameter and usually roughly spherical, although filamentous forms can occur. This particle is made of a viral envelope containing two main types of glycoproteins, wrapped around a central core. The central core contains the viral RNA genome and other viral proteins that package and protect this RNA. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to HA and NA. These different types of HA and NA form the basis of the H and N distinctions in, for example, H5N1.

Influenza viruses bind through hemagglutinin onto sialic acid sugars on the surfaces of epithelial cells; typically in the nose, throat and lungs of mammals and intestines of birds. The cell imports the virus by endocytosis. In the acidic endosome, part of the hemagglutinin protein fuses the viral envelope with the vacuole's membrane, releasing the viral RNA (vRNA) molecules, accessory proteins and RNA-dependent RNA polymerase into the cytoplasm. These proteins and vRNA form a complex that is transported into the cell nucleus, where the RNA-dependent RNA polymerase begins transcribing complementary positive-sense vRNA. The vRNA is either (a) exported into the cytoplasm and translated, or (b) remains in the nucleus. Newly-synthesised viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza viruses, the host cell dies.

Because of the absence of RNA proofreading enzymes, the RNA-dependent RNA polymerase makes a single nucleotide insertion error roughly every 10 thousand nucleotides, which is the approximate length of the influenza vRNA. Hence, the majority of newly-manufactured influenza viruses are mutants, causing "antigenic drift." The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

4. Other Viruses

The present disclosure contemplates the use of RNA segments deriving from other envelope proteins including West Nile virus, Japanese Encephalitis virus, Dengue virus and Classical Swine Fever virus (CSFV).

II. VIRAL RNA SEGMENTS AS IMMUNOSUPPRESSIVE AGENTS

In certain aspects, the disclosure is directed to viral RNA segments, such as those encoding an HCV E2 protein or its homolog from other viruses. The provision of RNA segments can be used to modulate immune function. It is contemplated that the compositions and methods disclosed herein may be utilized to express all or part of the RNA segments thereof. In certain embodiments, compositions of the disclosure may include RNAs encoding certain proteins. The RNA segments may comprise about 10, 11, 12, 13, 14, 15, 16, 17, 18, 19, 20, 21, 22, 23, 24, 25, 27, 30, 35, 40, 45, 50, 51, 75, 100, 150, 175, 200, 225, 250, 275, 300, 350, 400, 450 or 500 consecutive bases of an RNA genome, for example, from an envelope sequence. Determination of which RNA segments possess activity may be achieved using functional assays measuring T-cell activation and proliferation as well as cytokine production, which are familiar to those of skill in the art. An exemplary HCV E2 coding region (from strain H77) is shown below:

```
                                          (SEQ ID NO: 27)
GAAACCCATGTGACCGGCGGCAACGCGGGCCGTACCACCGCGGGCCTGGT

GGGCCTGCTG------------ACCCCGGGCGCGAAACAGAACATTCAGC

TGATTAACACCAACGGCAGCTGGCATATTAACAGCACCGCGCTGAACTGC

AACGAAAGCCTGAACACCGGCTGGCTGGCGGGCCTGTTTTAT---CAGCA

TAAATTTAACAGCAGCGGCTGCCCGGAACGTCTGGCGAGCTGCCGTCGTC

TGACCGATTTTGCGCAGGGCTGGGGCCCGATTAGCTATGCG---------

------AACGGCAGCGGCCTGGATGAACGTCCGTATTGCTGGCATTATCC

GCCGCGTCCGTGCGGCATTGTGCCGGCGALAAGCGTGTGCGGCCCGGTGT

ATTGCTTTACCCCGAGCCCGGTGGTGGTGGGCACCACC---GATCGTAGC

GGCGCGCCGACCTATAGCTGGGGCGCGAACGATACCGATGTGTTTGTGCT

GAACAAC---ACCCGTCCGCCGCTGGGCAACTGGTTTGGCTGCACCTGGA

TGAACAGCACCGGCTTTACCAAAGTGTGCGGCGCGCCGCCGTGCGTGATT

GGCGGCGTGGGCAACAAC------------------ACCCTGCTGTGCCC

GACCGATTGCTTTCGTAAATATCCGGAAGCGACCTATAGCCGTTGCGGCA

GCGGCCCGCGTATTACCCCGCGTTGCATGGTGGATTATCCGTATCGTCTG

TGGCAT---TATCCGTGCACCATTAACTATACCATTTTTAAAGTGCGTAT

GTATGTGGGCGGCGTGGAACATCGTCTGGAAGCGGCGTGCAACTGGACCC

GTGGCGAACGTTGCGATCTGGAAGATCGTGATCGTAGCGAACTGAGCCCG

CTGCTGCTGAGCACCACCCAGTGGCAGGTGCTGCCGTGCAGCTTTACCAC

CCTGCCGGCGCTGAGCACCGGCCTGATTCATCTGCATCAGAACATTGTGG

ATGTGCAGTATCTGTATGGCGTGGGCAGCAGCATTGCGAGCGTGGCGATT

AAATGGGAATATGTGGTGCTGCTGTTTCTGCTGCTGGCGGATGCGCGTGT

GTGCAGCTGCCTGTGGATGATGCTGCTGATTAGCCAGGCGGAAGCG
```

An exemplary YFV envelope encoding sequence is shown below:

```
                                          (SEQ ID NO: 28)
GCTCACTGCATTGGAATTACTGACAGGGATTTCATTGAGGGGGTGCATGG

AGGAACTTGGGTTTCAGCTACCCTGGAGCAAGACAAGTGTGTCACTGTTA

TGGCCCCTGACAAGCCTTCATTGGACATCTCACTAGAGACAGTAGCCATT

GATAGACCTGCTGAGGTGAGGAAAGTGTGTTACAATGCAGTTCTCACTCA

TGTGAAGATTAATGACAAGTGCCCCAGCACTGGAGAGGCCCACCTAGCTG

AAGAGAACGAAGGGGACAATGCGTGCAAGCGCACTTATTCTGATAGAGGC

TGGGGCAATGGCTGTGGCCTATTTGGGAAAGGGAGCATTGTGGCATGCGC

CAAATTCACTTGTGCCAAATCCATGAGTTTGTTTGAGGTTGATCAGACCA

AAATTCAGTATGTCATCAGAGCACAATTGCATGTAGGGGCCAAGCAGGAA

AATTGGAATACCGACATTAAGACTCTCAAGTTTGATGCCCTGTCAGGCTC

CCAGGAAGTCGAGTTCATTGGGTATGGAAAAGCTACACTGGAATGCCAGG

TGCAAACTGCGGTGGACTTTGGTAACAGTTACATCGCTGAGATGGAAACA

GAGAGCTGGATAGTGGACAGACAGTGGGCCCAGGACTTGACCCTGCCATG

GCAGAGTGGAAGTGGCGGGGTGTGGAGAGAGATGCATCATCTTGTCGAAT

TTGAACCTCCGCATGCCGCCACTATCAGAGTACTGGCCCTGGGAAACCAG

GAAGGCTCCTTGAAAACAGCTCTTACTGGCGCAATGAGGGTTACAAAGGA

CACAAATGACAACAACCTTTACAAACTACATGGTGGACATGTTTCTTGCA

GAGTGAAATTGTCAGCTTTGACACTCAAGGGGACATCCTACAAAATATGC

ACTGACAAAATGTTTTTTGTCAAGAACCCAACTGACACTGGCCATGGCAC

TGTTGTGATGCAGGTGAAAGTGTCAAAAGGAGCCCCCTGCAGGATTCCAG

TGATAGTAGCTGATGATCTTACAGCGGCAATCAATAAAGGCATTTTGGTT

ACAGTTAACCCCATCGCCTCAACCAATGATGATGAAGTGCTGATTGAGGT

GAACCCACCTTTTGGAGACAGCTACATTATCGTTGGGAGAGGAGATTCAC

GTCTCACTTACCAGTGGCACAAAGAGGGAAGCTCAATAGGAAAGTTGTTC

ACTCAGACCATGAAAGGCGTGGAACGCCTGGCCGTCATGGGAGACACCGC

CTGGGATTTCAGCTCCGCTGGAGGGTTCTTCACTTCGGTTGGGAAAGGAA

TTCATACGGTGTTTGGCTCTGCCTTTCAGGGGCTATTTGGCGGCTTGAAC

TGGATAACAAAGGTCATCATGGGGGCGGTACTTATATGGGTTGGCATCAA

CACAAGAAACATGACAATGTCCATGAGCATGATCTTGGTAGGAGTGATCA

TGATGTTTTTGTCTCTAGGAGTTGGGGCG
```

In particular, a segment from this coding region is believed to be a substrate for the Dicer enzyme, and thus RNA regions having this motif are particularly contemplated. Prediction models identify a number of RNA sequences that should serve as substrates for Dicer. Using the program miR-FIND (bioinfo.51donate.com/microrna/mir-find), a search of the HCV envelope (E2)-coding RNA/YFV env-coding sequences that purportedly inhibit T cell receptor signaling identified several potential Dicer sites, differing in number between different genotypes. Conserved ribonucleotides in the genotype 2a isolate (underlined) in the HCV E2 coding region:

(SEQ ID NO: 3)
CTCACGCCAAGGTGCCTGATCGACTACCCCTACAGGCTCTGGcattatcC
or (SEQ ID NO: 4)
CTCACGCCAAGGTGCCTGATCGACTACCCCTACAGGCTCTGGcattacccC The intervening sequences can vary, as it has been observed that the genotype 3 virus E2 coding region, which has some sequence diversity in this region, also inhibits T cell receptor signaling and T cell activation. It is apparent that the RNA is sufficient to inhibit T cell activation, as including a frameshift insertion at the start of the coding region did not abrogate the inhibition. Furthermore, it is clear that the RNA structure is needed, as mutation to remove the conserved sequence only rescued T cell signaling when mutations were made that change the RNA structure. Restoring the structure with alternative mutations restored the T cell inhibitory effect. The lower case letters represent the putative seed sequence, with the final capitalized C possibly being included. A comparable sequence for YFV is shown below (with lower case letters representing the seed sequence):

(SEQ ID NO: 37)
GACAACAACcuuuacaaaCTACATGGT

Thus, in certain embodiments, the RNA segment comprises at least about 51 bases of the HCV E2 protein and is 100 bases or less in length and containing a T-cell inhibitory domain, i.e., the seed sequence, or at least about 27 bases of the YFV Env protein and is 100 bases or less in length and containing a T-cell inhibitory domain, i.e., the seed sequence. Certain embodiments of the disclosure include various RNA segment encoding HCV/YFV polypeptides, in particular HCV E2 protein and YFV Nnv protein. For example, all or part of an HCV E2 protein/YFV Env protein encoding RNA may be used in various embodiments of the disclosure. In certain embodiments, the RNA segment may comprise, but is not limited to about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 225, about 220 or more bases, and any range derivable therein.

It also will be understood that sequences may include additional bases, and yet still be essentially as set forth in one of the sequences disclosed herein, so long as the sequence meets the criteria set forth above, including the maintenance of biological activity (e.g., immunosuppression). Theses sequences may be termed "heterologous."

Embodiments of the disclosure include various viral RNA segments and derivatives thereof. RNA segment variants can be substitutional, insertional or deletion variants. Deletion variants lack one or more bases of the native sequence that are not essential for function or immunosuppressive activity. Insertional mutants typically involve the addition of material at a non-terminal point in the RNA segment. Terminal additions, sometimes called fusions, are also contemplated.

The term "biologically functional equivalent" is well understood in the art and is further defined in detail herein. Accordingly, sequences may have from about 70% to about 80%; or from about 81% to about 90%; or from about 91% to about 99%; of bases that are identical to the native sequence.

The present disclosure may employ RNA segments that comprise modified, non-natural and/or unusual bases. Certain oligonucleotide modifications can improve stability against nuclease degradation has been achieved by introducing a phosphorothioate (P═S) backbone linkage at the 3' end for exonuclease resistance and 2' modifications (2'-OMe, 2'-F and related) for endonuclease resistance. A motif having entirely of 2'-O-methyl and 2'-fluoro nucleotides has shown enhanced plasma stability and increased in vitro potency. Sequences containing a 4'-thioribose modification have been shown to have a stability 600 times greater than that of natural RNA. Crystal structure studies reveal that 4'-thioriboses adopt conformations very similar to the C3'-endo pucker observed for unmodified sugars in the native duplex. Stretches of 4'-thio-RNA were well tolerated in both the guide and nonguide strands.

In the boranophosphate linkage, a non-bridging phosphodiester oxygen is replaced by an isoelectronic borane ($BH_3$) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs.

Certain terminal conjugates have been reported to improve or direct cellular uptake. Chemically-stabilized siRNAs with partial phosphorothioate backbone and 2'-β-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an NAA by means of a pyrrolidine linker does not result in a significant loss of gene-silencing activity in cell culture. These studies demonstrate that cholesterol conjugation significantly improves in vivo pharmacological properties of NAAs.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the disclosure concerns isolated nucleic acid segments and recombinant vectors incorporating DNA sequences encoding viral envelope polypeptides or peptides. These polypeptides/peptides include within their amino acid sequence a contiguous amino acid sequence in accordance with, or essentially corresponding to viral envelope polypeptides. Also envisioned are variants that have modification in one or more kinase sites within these polypeptides.

The nucleic acid segments used in the present disclosure, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length being limited solely by the ease of preparation and use in the intended recombinant DNA protocol.

A. Vectors Carrying HCV E2 Sequences or Other Viral Envelope Regions

The present disclosure also encompasses the use of vectors to provide the RNA segment. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). In particular embodiments, gene therapy or immunization vectors are contemplated. One of skill in the art would be well equipped to construct a vector through standard recombinant techniques, which are described in Maniatis et al., 1988 and Ausubel et al., 1994, both incorporated herein by reference.

The term "expression vector" or "expression construct" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment. The promoter may be heterologous or exogenous, i.e., from a different source than viral sequence. In some examples, a prokaryotic promoter is employed for use with in vitro transcription of a desired sequence. Prokaryotic promoters for use with many commercially available systems include T7, T3, and Sp6.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse $\alpha$(XI) collagen (Tsumaki, et al., 1998), D1A dopamine receptor gene (Lee et al., 1997), insulin-like growth factor II (Wu et al., 1997), human platelet endothelial cell adhesion molecule-1 (Almendro et al., 1996).

2. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. For proteins, it is well known that the initiation codon needs to be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may include donor and/or acceptor splicing sites to ensure proper processing of the transcript for protein expression. See Chandler et al., 1997, herein incorporated by reference.

5. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, the terminator comprises a signal for the cleavage of the RNA, and in other embodiments the terminator signal promotes polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Some embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

8. Selectable and Screenable Markers

In certain embodiments of the disclosure, the cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

C. Introduction of Nucleic Acids into Cells

In certain embodiments, a nucleic acid may be introduced into a cell. There are a number of ways in which nucleic acid molecules such as vectors may be introduced into cells. The ability of certain viruses to enter cells via receptor-mediated endocytosis, to integrate into host cell genome and express viral transcripts stably and efficiently have made them attractive candidates for the transfer of foreign genes into mammalian cells (Ridgeway, 1988; Nicolas and Rubenstein, 1988; Baichwal and Sugden, 1986; Temin, 1986).

"Viral expression vector" is meant to include those vectors containing sequences of that virus sufficient to express a polynucleotide that has been cloned therein. A number of such viral vectors have already been thoroughly researched, including adenovirus, adeno-associated viruses, retroviruses, herpesviruses, and vaccinia viruses.

Delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. Several non-viral methods for the transfer of expression vectors into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), liposome (Ghosh and Bachhawat, 1991; Kaneda et al., 1989) and receptor-mediated transfection (Wu and Wu, 1987; Wu and Wu, 1988). Some of these techniques may be successfully adapted for in vivo or ex vivo use.

In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro, but it may be applied to in vivo use as well.

III. IMMUNOSUPPRESSIVE THERAPY

A. Inflammatory Conditions

The present disclosure relates to the use of viral RNA segment for the modulation of immune responses, particularly those relating to pathologic inflammation. In one embodiment, the pathologic inflammation relates to interleukin-2 (IL-2) expression. IL-2 has multiple, sometimes opposing, functions during an inflammatory response. It is a potent inducer of T cell proliferation and T-helper 1 (Th1) and Th2 effector T cell differentiation and provides T cells with a long-lasting competitive advantage resulting in the optimal survival and function of memory cells. In a regulatory role, IL-2 is important for the development, survival, and function of regulatory T cells, it enhances Fas-mediated activation-induced cell death, and it inhibits the development of inflammatory Th17 cells. Thus, in its dual and contrasting functions, IL-2 contributes to both the induction and the termination of inflammatory immune responses.

The present disclosure would therefore seek to intervene in those diseases where, for example, IL-2 is activating T cells and leading to inflammatory states. Such diseases include autoimmune diseases like multiple sclerosis, psoriasis, inflammatory bowel disorders, early arthritis, juvenile arthritis, rheumatoid arthritis, enteropathic arthritis, psoriatic arthritis, ankylosing spondylitis, familial Mediterranean fever, amyotrophic lateral sclerosis, systemic lupus erythematosus, ulcerative colitis, inflammatory bowel disease, Sjögren's syndrome, or Crohn's disease. Other inflammatory conditions include cardiovascular disease, trauma, or pancreatitis.

B. Gene Therapy

In one embodiment, the disclosure contemplates including immunosuppressive sequences from one or more of the viruses mentioned herein nucleic acid constructs used for gene therapy. One problem with gene therapy is achieving sustained expression, which generally requires multiple administrations. Whether from a single administration or multiple ones, immune reactions against the delivery vector/vehicle can result. Therefore, including immunomodulatory domains described herein is suggested herein in gene therapy vectors as a way to blunt unwanted and limiting host immune reactions against the gene therapeutic modality.

C. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render proteins stable. Buffers also will be employed when RNA segment are introduced into a patient. Aqueous compositions of the present disclosure comprise an effective amount of the RNA segment dissolved or dispersed in a pharmaceutically acceptable carrier or aqueous media. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The percentage of active compound in any pharmaceutical preparation is dependent upon both the activity of the compound. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. The form should be sterile and should be fluid to the extent that easy injection is possible. It should be stable under the conditions of manufacture and storage and should be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention or control of the action of microorganisms can be brought about by various antibacterial and antifungal agents, for example, parabens, chlorobutanol, phenol, sorbic acid, thimerosal, phenylmercuric nitrate, m-cresol, and the like. In some embodiments isotonic solutions, for example, sugars or sodium chloride may be used. Prolonged absorption of the injectable compositions can be brought about by the use in the compositions of agents delaying absorption, for example, aluminum monostearate, and gelatin.

Sterile injectable solutions are prepared by incorporating the active compounds in the needed amount in the appropriate solvent with various other ingredients enumerated above, as necessary, followed by sterile filtration. Generally, dispersions are prepared by incorporating the various sterilized active ingredients into a sterile vehicle which contains the basic dispersion medium and the other ingredients from those enumerated above. In the case of sterile powders for the preparation of sterile injectable solutions, the methods of preparation can be vacuum drying and freeze-drying techniques that yield a powder of the active ingredient plus any additional desired ingredient from a previously sterile-filtered solution thereof.

The present disclosure contemplates a viral RNA immunosuppressive segment, and nucleic acid molecules coding therefor. In some embodiments, pharmaceutical compositions are administered to a subject. Different aspects of the present disclosure involve administering an effective amount of an aqueous composition. Such compositions will generally be dissolved or dispersed in a pharmaceutically acceptable carrier or aqueous medium. Those of skill in the art are well aware of how to administer agents, as well as gene delivery to in vivo and ex vivo situations.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present disclosure can be formulated for parenteral administration, e.g., formulated for injection via the intravenous, intramuscular, intrathoracic, sub-cutaneous, or even intraperitoneal routes. Administration by i.v. or i.m. is specifically contemplated.

The active compositions may be formulated as neutral or salt forms. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, it may be desirable to provide a continuous supply of compositions to the patient. For intravenous or intraarterial routes, this is accomplished by drip system. For various approaches, delayed release formulations could be used that provided limited but constant amounts of the therapeutic agent over and extended period of time. For internal application, continuous perfusion may be used. This could be accomplished by catheterization followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

RNA segments may be administered in a dose that can vary from 0.01, 0.05, 0.1, 0.5, 1, 5, 10, 20, 30, 40, 50, 60, 70, 80, 90, 100 mg/kg of weight to 50, 60, 70, 80, 90, 100, 110, 120, 130, 140, 150, 160, 170, 180, 190, 200 mg/kg of weight in one or more daily, weekly, monthly, or yearly administrations during one or various days, weeks, months, or years. The RNA segments can be administered by parenteral injection (intravenous, intraperitoneal, intramuscular, subcutaneous, intracavity or transdermic).

In many instances, it will be desirable to have multiple administrations of the RNA segments of the disclosure. The compositions of the disclosure may be administered 1, 2, 3, 4, 5, 6, 7, 8, 9, 10, or more times. The administrations will normally be at from one to twelve week intervals, more usually from one to four week intervals.

Dosages commonly used for formulations that provide passive immunity are in the range of from 0.5 mL to 10 mL per dose, or in the range of 2 mL to 5 mL per dose. Repeated doses to deliver the appropriate amount of active compound are common. Both the age and size by weight of the recipient should be considered when determining the appropriate dosage of active ingredient and volume to administer.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal.

D. Combinations with Anti-Inflammatories

It is common in many fields of medicine to treat a disease with multiple therapeutic modalities, often called "combination therapies." Inflammatory diseases are no exception. To treat inflammatory disorders using the methods and compositions of the present disclosure, one would generally contact a target cell or subject with a viral RNA immunosuppressive segment and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes a viral immunosuppressive segment and the other includes the other agent.

Alternatively, the immunosuppressive RNA segment may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either a viral immunosuppressive segment or the other therapy will be desired. Various combinations may be employed, where the viral RNA segment is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | | B/B/A/A | B/A/B/A | B/A/A/B | B/B/B/A |
| A/A/A/B | B/A/A/A | A/B/A/A | | A/A/B/A | A/B/B/B | B/A/B/B | B/B/A/B |

Other combinations are contemplated.

Agents or factors suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

IV. VACCINES

In an embodiment of the present disclosure, a method of inducing an enhanced immune response to the engineered viral RNA segments rather than native RNAs to prevent, control or limit viral infection is provided. Modified viral RNA segments lacking one or more immunosuppressive sites will be used in subunit or whole virus immunization. An effective amount of a vaccine composition, generally, is defined as that amount sufficient to detectably and repeatedly ameliorate, reduce, minimize or limit the extent of the disease or condition or symptoms thereof. More rigorous definitions may apply, including elimination, eradication or cure of disease.

A. Administration

The compositions of the present disclosure may be used in vivo to modify or modulate an immune response, and thus constitute therapeutic and prophylactic vaccines. Thus, the compositions can be formulated for parenteral administration, e.g., formulated for injection via the intradermal, intravenous, intramuscular, subcutaneous, or intraperitoneal routes. Administration by intradermal and intramuscular routes is specifically contemplated. The vaccine can also be administered by a topical route directly to the mucosa, for example by nasal drops or mist, inhalation, or by nebulizer.

Some variation in dosage and regimen will necessarily occur depending on the age and medical condition of the subject being treated, as well as the route chosen. The person responsible for administration will, in any event, determine the appropriate dose for the individual subject. In many instances, it will be desirable to have multiple administrations of the vaccine. Thus, the compositions of the disclosure may be administered 1, 2, 3, 4, 5, 6, 7, 8, 9, 10, or more times. The administrations will normally be at from one to twelve week intervals, more usually from one to six week intervals. Periodic re-administration will be desirable with recurrent exposure to the pathogen.

The administration may use various "unit doses." Unit dose is defined as containing a predetermined-quantity of the therapeutic composition. The quantity to be administered, and the particular route and formulation, are within the skill of those in the clinical arts.

B. Measuring Immune Responses

One of ordinary skill would know various assays to determine whether an immune response against a vaccine was generated. The phrase "immune response" includes both cellular and humoral immune responses. Various B lymphocyte and T lymphocyte assays are well known, such as ELISAs, cytotoxic T lymphocyte (CTL) assays, such as chromium release assays, proliferation assays using peripheral blood lymphocytes (PBL), tetramer assays, and cytokine production assays. See Benjamini et al. (1991), hereby incorporated by reference.

C. Injectable Formulations

One method for the delivery of a pharmaceutical according to the present disclosure is via injection. However, the pharmaceutical compositions disclosed herein may alternatively be administered intravenously, intradermally, intramuscularly, or even intraperitoneally as described in U.S. Pat. Nos. 5,543,158; 5,641,515 and 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery.

Solutions of the vaccine as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent or control the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). The form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The prevention or control of microorganisms can be brought about by various antibacterial and antifungal agents, for example, parabens, chlorobutanol, phenol, sorbic acid, thimerosal, and the like. In some embodiments isotonic agents, for example, sugars or sodium chloride may be used. Prolonged absorption of the injectable compositions can be brought about by the use in the compositions of agents delaying absorption, for example, aluminum monostearate and gelatin. Sterile aqueous media that can be employed will be known to those of skill in the art in light of the present disclosure. For example, one dosage may be dissolved in 1 mL of isotonic NaCl solution and either added to 1000 mL of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the needed amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and any of the other ingredients from those enumerated above. In the case of sterile powders for the preparation of sterile injectable solutions, the methods of preparation can be vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous injectable composition that contains a protein as an active ingredient is well understood in the art.

D. Inhalable or Aerosol Formulations

A particular mode of administration contemplated for the RNA segments of the present disclosure is via inhalation and/or administration to the nasal mucosa, i.e., intranasal administration. A variety of commercial vaccines (influenza, measles) are currently administered using a nasal mist formulation. The methods of the present disclosure can be carried out using a delivery similar to that used with the Flu-Mist® product, which employs the BD AccuSpray® System (Becton Dickinson). Also useful for this route are nebulizers, such as jet nebulizers and ultrasonic nebulizers.

E. Additional Vaccine Components

In other embodiments of the disclosure, the antigenic composition may comprise an additional immunostimulatory agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination.

1. Adjuvants

As also well known in the art, the immunogenicity of a particular immunogen composition can be enhanced by the use of non-specific stimulators of the immune response, known as adjuvants. Adjuvants have been used to promote a generalized increase in immunity against unknown antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. Suitable molecule adjuvants include all acceptable immunostimulatory compounds, such as cytokines, toxins or synthetic compositions.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants that may also be used include IL-1, IL-2, IL-4, IL-7, IL-12, γ-interferon, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (CARBOPOL®) used as an about 0.25% solution. Adjuvant effect may also be made my aggregation of the antigen in the vaccine by heat treatment with temperatures ranging between about 70° C. to about 101° C. for a 30-second to 2-minute period, respectively. Aggregation by reactivating with pepsin-treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is muramyl dipeptide (N-acetylmuramyl-L-alanyl-D-isoglutamine; MDP), a bacterial peptidoglycan. The effects of MDP, as with the majority of adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the disclosure. Hemocyanin from keyhole limpet (KLH) can be used in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides such as chitin and chitosan, including deacetylated chitin can be used.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present disclosure.

BCG (*bacillus* Calmette-Guerin, an attenuated strain of *Mycobacterium*) and BCG-cell wall skeleton (CWS) may also be used as adjuvants, with or without trehalose dimycolate. Trehalose dimycolate may be used itself. Trehalose dimycolate administration has been reported to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is TICE BCG (Organon Inc., West Orange, N.J.).

Amphipathic and surface active agents, e.g., saponin and derivatives such as QS21 (Cambridge Biotech), form yet another group of adjuvants for use with the immunogens of the present disclosure. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present disclosure.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of CWS and trehalose dimycolate, without detoxified endotoxins, are also envisioned to be useful, as described in U.S. Pat. No. 4,520,019.

Those of skill in the art will know the different kinds of adjuvants that can be conjugated to cellular vaccines in accordance with this disclosure and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the disclosure (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

2. Biological Response Modifiers

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/$m^2$) (Johnson/Mead, NJ), cytokines such as γ-interferon, IL-2, or IL-12 or genes encoding proteins involved in immune helper functions, such as B-7.

3. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines (e.g., IFN's) are also known to have chemoattractant effects and could also be classified under the term chemokines.

V. EXAMPLES

The following examples are included to demonstrate certain embodiments of the disclosure. It should be appreciated by those of skill in the art that the techniques disclosed in the examples which follow represent techniques that were determined to function well in the practice of the disclosure, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Cells and Viruses.

Human hepatocellular carcinoma cell line (Huh-7.5; kindly provided by Dr. Charles Rice, The Rockefeller University) was cultured in Dulbecco's modified Eagle's medium (DMEM) containing 10% fetal bovine serum, 1% penicillin-streptomycin and 1% L-glutamine at 37° C. in a 5% $CO_2$. HCV positive human serum infected with genotypes (1, 1a, 1b, 2, 2b and 3) or negative control serum was prepared from blood obtained from patients or from healthy blood donors. Huh 7 cells containing replicons consisting of either the full length HCV genome or the NS2-5 region of the genomes were kindly provided by Dr. Ralf Bartenschlager (University of Heidelberg) and maintained as described (Lohmann et al., 1999 and Quinkert et al., 2005). Serum extracellular vesicles (EV) were purified from serum using the ExoQuick reagent (Systems Biosciences) according to the manufacturer's instructions. Specifically, human sera was incubated with the Exoquick reagent for 1 hr (4° C.) and centrifuged 30 min (10,000 g) as recommended. The pellet was resuspended in RPMI and stored at −20° C. until use. This reagent has been reported to yield EVs from both cell culture supernatant and human serum (Fabbri et al., 2012). Cell culture derived, infectious HCV particles (HCVcc) were obtained by transfecting Huh7.5 cells with in vitro transcribed HCV RNA from J6/JFH infectious clone (kindly provided by Dr. Takaji Wakita, Tokyo Metropolitan Institute of Neuroscience, and Dr. Charles Rice, Rockefeller University) as described by others (Lindenbach et al., 2005). Cell culture supernatant was harvested 72 hrs following transfection and concentrated. The HCV titer in the culture supernatant was $4.98\times10^7$ (copies/mL). $4.98\times10^7$ particles were added to $1\times10^6$ cells. HCV (E1-E2) pseudotyped HIV particles (HCVpp) or HIV gag particles without a viral envelope (GAGpp) were generated in HEK 293T cells using pNL4-3-Luc.R-E- (NIRRRP catalog #3417) as described (Mohr et al., 2010). HCVcc, HCVpp and GAGpp in supernatants were concentrated using Amicon 100K filter units (Millipore) and HCVpp/GAGpp were quantified using p24 ELISA (Zeptometrix Inc.).

Expression of HCV Envelope Protein.

Coding regions of HCV E2 protein from J6/JFH plasmid (aa 384-747) (Lindenbach et al., 2005) or from a genotype 3 isolate obtained from a patient from the University of Iowa were amplified and ligated into a modified pTRE2-HGY plasmid (Clontech, Inc.) as previously described (Xiang et al., 2012). HCV sequences were confirmed by sequencing plasmid DNA (University of Iowa DNA Core Facility). The modified plasmid generates a bicistronic message encoding the HCV E2 sequence followed by stop codons, the encephalomyocarditis virus (EMC) internal ribosomal entry site (IRES) directing the translation of GFP. Jurkat (tet-off) cell lines (Clontech, Inc) were transfected (Nucleofector II, Lonza Inc.) and cell lines were selected for hygromycin and G418 resistance. GFP positive cells were bulk sorted (BD FACS Aria, (University of Iowa Flow Cytometry Facility) and GFP expression was assessed by flow cytometry (BD LSR II). HCV E2 protein expression was determined by immunoblot using human monoclonal antibodies (HC33-1, kindly provided by Dr. Steven Foung, Stanford University). All cell lines were maintained in RPMI 1640 supplemented with 10% heat-inactivated fetal calf serum, 2 mM L-glutamine, 100 IU/mL penicillin, and 100 μg/mL streptomycin with hygromycin and G418 (200 μg/mL).

Cell Isolation and Stimulation.

Peripheral blood mononuclear cells (PBMCs) were prepared from blood obtained from healthy donors by Ficoll-gradient centrifugation. PBMCs were incubated with HCV positive or negative serum (100 μl for each unless otherwise stated) overnight. $CD3^+$ (T) cells were enriched by positive selection using magnetic system according to manufacturer's instructions (Miltenyi Biotec, Auburn, Calif.), and purity assessed by flow cytometry. PBMCs ($1\times10^6$ cells/mL) were stimulated with plate-bound anti-CD3 (100 ng/mL, OKT3 clone, eBioscience) and soluble CD28 antibody (100 ng/mL, clone CD28.2, BD Biosciences). Jurkat cells ($5\times10^6$ cells/mL) were stimulated with anti-CD3 and soluble CD28 (both at 5 μg/mL) or phorbol-12-myristate-13-acetate (PMA, 50 ng/mL) and ionomycin (1 μg/mL) (P+I). Cellular receptor expression and cytokine release were measured 24 hours post-stimulation by flow cytometry and ELISA respectively. For Lck inhibition, Jurkat cells were incubated with Lck inhibitor II (EMD Millipore) at 100 μg/mL overnight before stimulating with P+I.

Flow Cytometry:

Cell surface receptor expression was measured with CD69 (APC), or CD45 (PE) antibodies (BD Biosciences) using the manufacturer's recommendations. Cells were incubated on ice for 1 hour, washed 3 times with PBS and fixed in 2% paraformaldehyde (Polysciences). Purified extracellular cellular vesicles (EV) were stained with either anti-CD63 exo-flow staining kit (Systems Biosciences) or CFSE dye (5 μM) for 15 minutes at 37° C. EVs were washed in PBS four times and concentrated using Amicon 100K filter units (Millipore). Data was acquired on BD LSR II flow cytometer using single stained CompBeads (BD Biosciences) for compensation. At least 10,000 total events were collected in each study and the FlowJo software program (Tree Star Inc.) was used for data analysis. All flow cytometry studies were repeated at least three times with consistent results.

HCV PCR.

After overnight incubation, PBMCs were incubated in trypsin for 1 minute and washed twice with RPMI. Total RNA was isolated (RNeasy Kit, Qiagen) and cDNA was made with HCV 5' UTR specific primers or random hexamers. For first round RT-PCR, the outer primers were sense 5'CTCCACCCAATGAATCACTCCC (SEQ ID NO: 29) and antisense 5'GAGGTTTAGGATTCGTGCTC (SEQ ID NO: 30). For nested PCR, the primers were sense 5'CGTTAGTATGAGTGTCGTGC (SEQ ID NO: 31) and antisense 5'GATGCACGGTCTACGAGACC (SEQ ID NO: 32). The final product size was 250 bp. GAPDH primers used were sense 5'ATCCCATCACCATCTTCCAG (SEQ ID NO: 33) and antisense 5'CCATCACGCCACAGTTTCC (SEQ ID NO: 34) which generates a product size of 383 bp.

HCV E2 derived small RNAs were identified as follows, total RNA from Jurkat cells expressing HCV E2 was isolated (RNeasy Kit, Qiagen). RNA was ligated to a pre-adenylated DNA universal miRNA cloning linker (New England Biolabs) using T4 RNA ligase 2 (New England Biolabs) according to the manufacture's protocol. Ligated RNA was purified using RNA columns (Qiagen) and cDNA transcribed using a DNA linker primer (5'-ATTGATGGTGCCTACAG-3' (SEQ ID NO: 35)). PCR was carried out using HCV E2 primer (5'-TCCTGATACCACTTACCTCAA-3' (SEQ ID NO: 36)) and DNA linker primer. PCR products were cloned into TA cloning vector (Invitrogen) and DNA sequences were obtained by sequencing plasmid (University of Iowa DNA Core Facility).

ELISA and Immunoblot Analyses.

IL-2 cytokine released into cell culture supernatant was quantified using human IL-2 ELISA kit (BD Biosciences) according to the manufacturer's instructions. Jurkat cells were stimulated with anti-CD3 (5 μg/mL) for the indicated times prior to addition of cell lysis buffer (Cell Signaling). Following PMA/Ionomycin stimulation for 15 min, nuclear proteins were isolated using nuclear protein isolation kit (NEPER, Thermo Scientific) following manufacturer's instructions. Proteins were separated by polyacrylamide gel electrophoresis and transferred to nitrocellulose membranes (BIORAD). Membranes were incubated in protein-free blocking buffer (Thermo Scientific) for 1 hour at room temperature followed by incubation with primary antibodies. Proteins were detected with Amersham ECL (GE Healthcare) using a Kodak Imager. Primary antibodies used were: NFAT and pLAT (Y226; BD Biosciences); total LAT (Biolegend); pZAP70 (Y319); total ZAP70; pLck (Y394/pSrcY416); total Lck (Y394); Csk; YY1 (all from Cell Signaling Technology); PTPRE (Origene, clone 4B2). Immunoblots were quantified by ImageJ.

In Vitro Kinase Assay.

Phosphorylation of HCV E2 protein by Lck was measured by incubating recombinant E2 protein (eEnzyme) with or without human Lck (R&D Systems) and CD45 (Enzo Life Sciences) as recommended by the manufacturer. Samples were subjected to immunoblot analysis as described above. Phosphorylation was determined by immunoblot analysis with phosphotyrosine antibodies (Invitrogen) and HCV E2 protein was identified using anti-HCV E2 human monoclonal antibodies described above.

Immunoprecipitation.

Jurkat cells stably expressing HCV E2 (aa 384-715 of the HCV polyprotein) with a C-terminal influenza hemagluttinin (HA) tag were stimulated with 10 μg/mL of anti-CD3 for 15 min and lysed (25 mM Tris, 150 mM NaCl, 5% Glycerol, 1 mM EDTA, 1% NP40; 1 hr on ice). Cell lysates were incubated with anti-HA agarose beads (Thermo Scientific) or NFAT antibodies conjugated to protein G beads at 4° C. overnight. Beads were pelleted and washed 3 times in lysis buffer. Bound proteins were eluted in 2× LaemmLi sample buffer prior to immunoblot analysis.

Statistics:

Statistics were performed using GraphPad software V4.0 (GraphPad Software Inc.). Two-sided Student's t test was used to compare results between test and controls. P values less than 0.05 were considered statistically significant.

Ethics Statement:

This study was approved by the University of Iowa Institutional Review Board. All subjects (healthy donors and subjects with viral infections) provided written informed consent.

Example 2—Results

HCV Particles Inhibit TCR Signaling in Primary Human T Cells.

Figure 10:
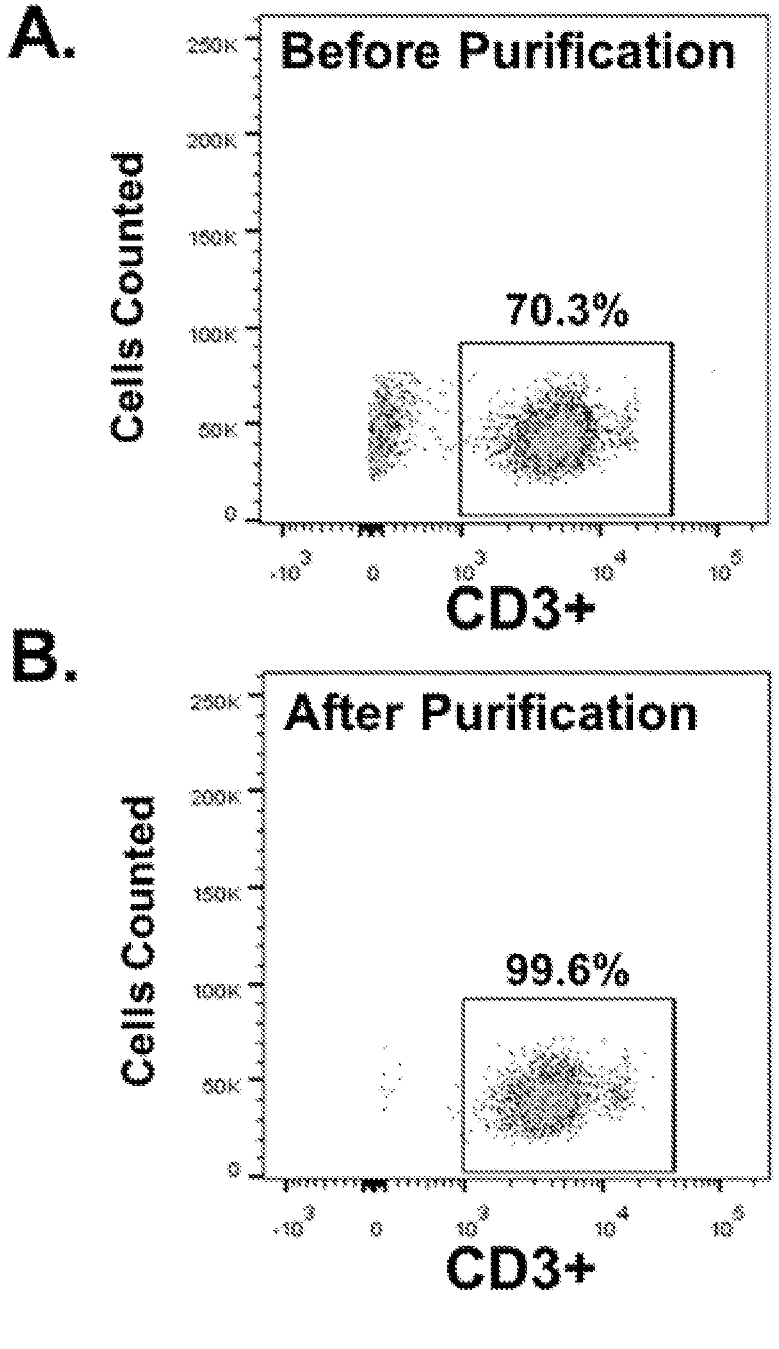
FIGS. 10A-B. Purity of CD3+ T lymphocytes following purification.

Serum from HCV-infected subjects (genotypes 1, 1a, 1b, 2, 2b and 3; RNA concentration range $1\times10^5$ to $1\times10^6$ RNA genome equivalents [GE] per mL), or HCV uninfected controls were incubated with PBMCs obtained from healthy blood donors. Following TCR stimulation with anti-CD3/CD28, signaling was quantified by measuring IL-2 release into culture supernatants or by measuring CD69 expression on these primary CD4+ and CD8+ T lymphocytes. All HCV RNA positive sera inhibited IL-2 release (FIG. 1A) and CD69 surface expression (FIG. 1B) in a dose-dependent manner (FIG. 1C) compared to HCV-uninfected controls. Testing purified T cells (>99% pure, FIG. 10) confirmed that HCV RNA positive sera inhibited T cell activation in the absence of other cell types as measured by IL-2 release (FIG. 1D).

To remove serum factors that may interfere with TCR signaling, serum extracellular vesicles (EV) were prepared using a commercial reagent (Exoquick, Systems Biosciences). This method of purification yields well characterized EV consistent with exosomes from human serum (Fabbri et al., 2012). Exosomes are reported to contain HCV envelope proteins, HCV RNA and to transmit HCV infection in vitro (Ramakrishnaiah et al., 2013; Cosset and Dreux, 2014; Masciopinto et al., 2004; Bukong et al., 2014 and Dreux et al., 2012). Purified HCV RNA-containing EV contained CD63 and CD81 but did not contain CD69 and CD25 (FIG. 11A), supporting an endocytic source of origin. Incubation of PBMCs with EV from HCV-infected individuals inhibited IL-2 release and CD69 expression (FIGS. 2A-B, respectively) compared to HCV-negative control EV. Although this method of preparation yields EVs with characteristics of exosomes, the possibility that some viral particles are included in the preparation cannot be excluded.

Figure 2:
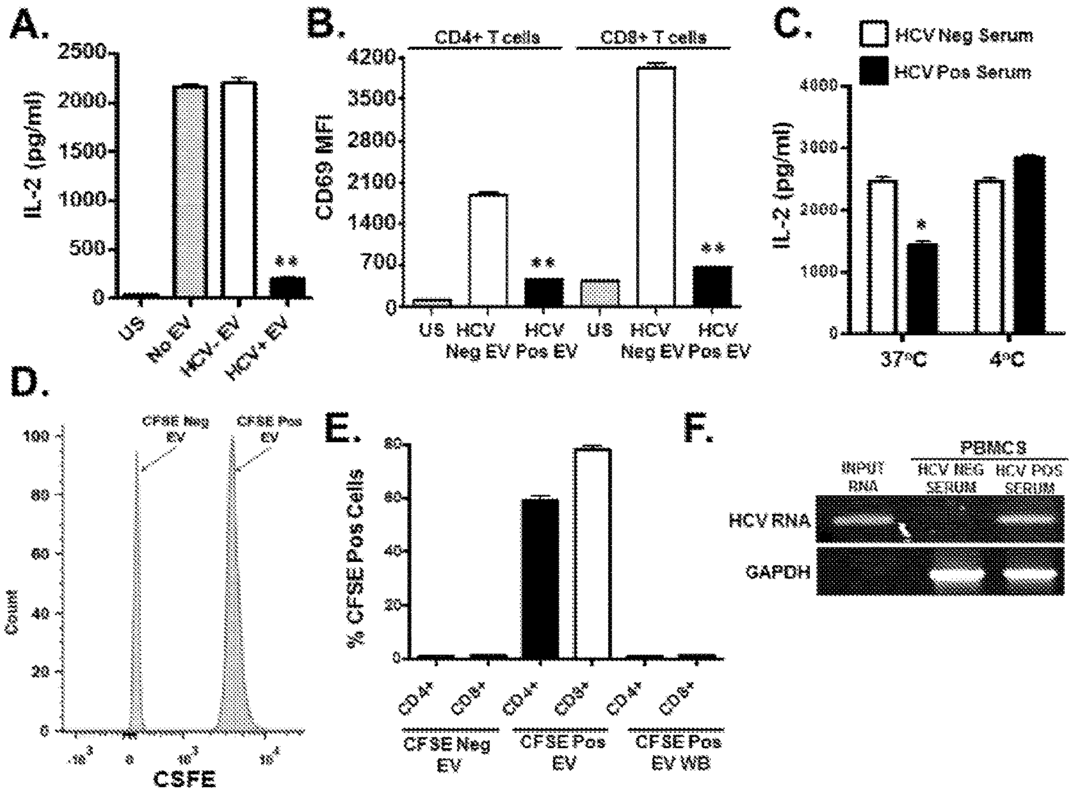
FIGS. 2A-F. HCV serum derived extracellular vesicles (EV) inhibit T cell receptor (TCR) signaling in primary human T lymphocytes. Healthy donor PBMCs were incubated with pooled serum extracellular vesicles (EV) obtained from HCV-infected patient sera (HCV+EV; GT 1, 1a, 1b, 2, 2b and 3). TCR induced IL-2 (FIG. 2A) and CD69 surface expression (FIG. 2B) was measured. TCR induced IL-2 release by human T cells incubated with HCV-positive or negative serum for two hours at 37° C. or 4° C.
Figure 11:
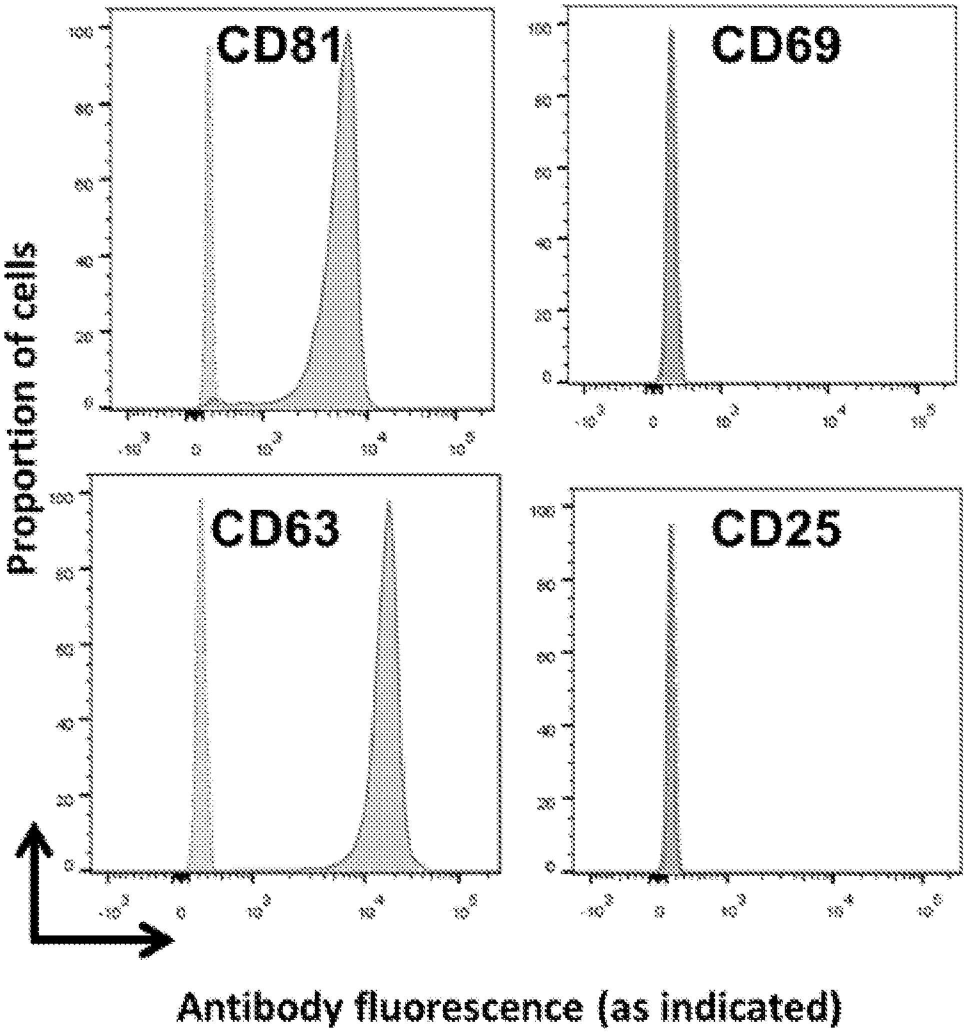
FIG. 11. Characterization of extracellular vesicles (EVs) purified from serum and quantification of HCV RNA.

To further examine EV interactions with lymphocytes, sera from HCV infected or uninfected subjects were incubated with purified T cells at 37° C. or at 4° C. Following two hour incubation and wash (at room temperature), cells were stimulated with anti-CD3/CD28. HCV positive sera significantly inhibited TCR signaling at 37° C. but not 4° C. (FIG. 2C). The extent of inhibition was less, presumably due to the shortened incubation compared to earlier studies. To assess EV fusion with cells, serum EVs from HCV positive or negative subjects were labelled with carboxyfluorescein succinimidyl ester (CFSE) (FIG. 2D) prior to incubation with primary human PBMCs. EV transferred CFSE to both CD4+ and CD8+ T cells during overnight incubation (FIG. 2E). Since CFSE is a cell-permeable dye and trace amounts of CFSE could lead to a positive result, cells were also incubated in the final wash buffer (EV wash) and CFSE was not detected in these cells (FIG. 2E). Further, HCV RNA was transferred from EV to PBMCs during the same incubation (FIG. 2F). Thus serum-derived HCV particles fused with and transferred viral RNA into T cells. To exclude the possibility that serum mediated T cell uptake of virus or EV's in vitro, HCV RNA was amplified from T cells purified from PBMCs (>97% pure) as described above. HCV RNA was present in both PBMCs and purified T cells obtained from HCV-infected subjects, whereas viral RNA was not detected in HCV-uninfected subject (FIG. 11B).

Figure 3:
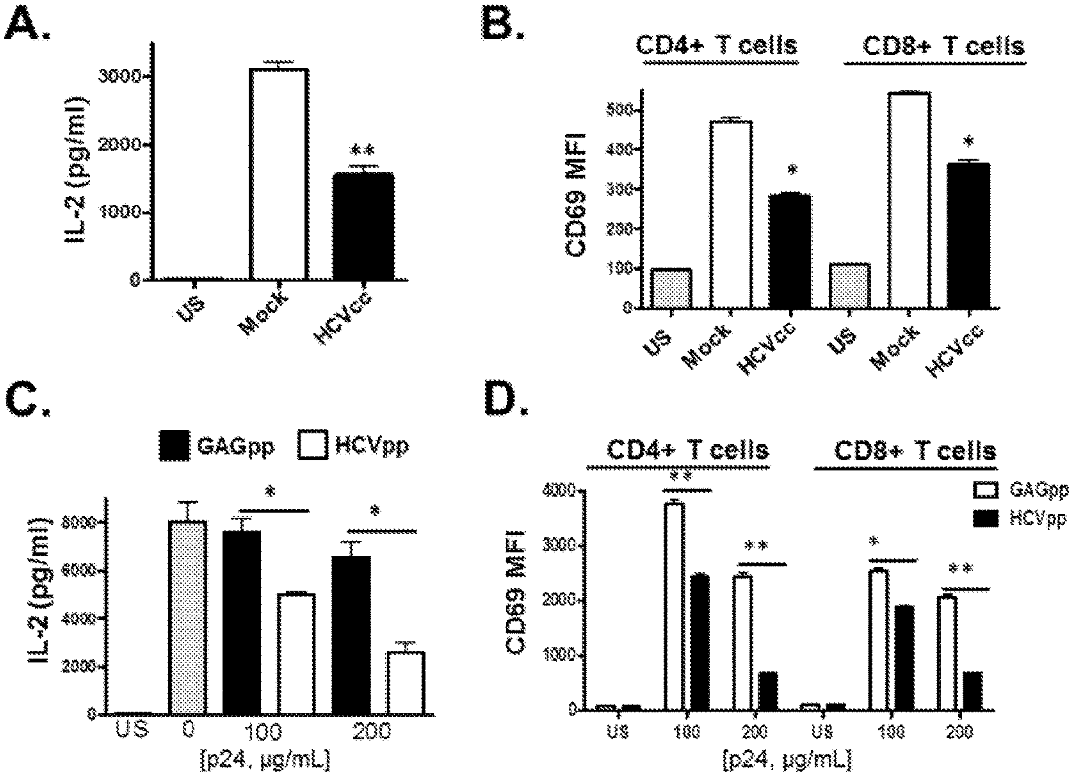
FIGS. 3A-D. HCV cell culture derived particles (HCVcc) and HCV envelope pseudotyped retrovirus particles (HCVpp) inhibit T cell receptor (TCR) signaling in primary human T cells. HCVcc produced in Huh7.5 cells inhibited TCR-mediated IL-2 release (FIG. 3A) and CD69 surface expression (FIG. 3B) in human peripheral blood mononuclear cells compared to cells incubated in mock-transfected Huh7.5 cell culture supernatant fluids following TCR stimulation with anti-CD3/CD28. Similarly, HCVpp's inhibited TCR-mediated IL-2 release (FIG. 3C) and CD69 surface expression (FIG. 3D) compared to cells incubated in retrovirus GAG particles in a dose-related manner. US=unstimulated cells. MFI=mean fluorescent intensity. Data represent the average of three technical replicates. The standard deviation is shown. Each study was independently performed three times using different donors with similar results. $*P<0.05$; $**P<0.01$.

Next, infectious HCV particles generated in a hepatocyte cell line (Huh7.5 cells) were incubated with PBMCs prior to TCR stimulation. Similar to serum-derived EV, cell culture infectious HCV particles (HCVcc) inhibited TCR signaling in CD4+ and CD8+ T cells (FIGS. 3A-B). Viral replication was not required, as replication defective retrovirus particles pseudotyped with the HCV E1 and E2 (HCVpp) also inhibited TCR signaling in a dose-dependent manner compared to non-enveloped retrovirus particles (GAGpp; FIGS. 3C-D). HCVcc's and HCVpp's also inhibited TCR signaling in purified CD3+ T cells (>99% pure, FIG. 12), thus the mechanism of TCR signaling inhibition by HCV particles does not require the presence of other immune cells.

In summary, incubation of primary human PBMCs with i) serum from HCV-infected individuals, ii) HCV RNA and CD63/CD81 containing serum-derived EV, iii) HCVcc and iv) HCVpp reduced TCR-mediated activation in primary human CD4+ and CD8+ T cells compared to controls.

HCV E2 Coding RNA Inhibits Proximal TCR Signaling Pathways.

Since HCVpp particles contain essentially only HCV E1 and E2, the major HCV envelope glycoprotein (E2) was examined for its ability to inhibit T cell activation through the TCR. Since HCV does not replicate well, if at all, in lymphocytes, Jurkat (CD4+) T cell lines stably expressing HCV E2 protein (FIG. 13A) were generated. In the cells expressing full-length E2 (aa 384-747), significantly less TCR-mediated activation as determined by IL-2 release (FIG. 4A) or surface CD69 increase (FIG. 13B) was observed compared to control Jurkat cells only expressing GFP. The most proximal kinase in the TCR signaling cascade is the lymphocyte-specific protein tyrosine kinase (Lck) (Davis and van der Merwe, 2011). Inactive Lck is phosphorylated at tyrosine 505 (Y505) by the c-src tyrosine kinase (Csk). Following TCR engagement, Y505 is dephosphorylated by many tyrosine phosphatases including CD45, resulting in conformational changes and subsequent auto-trans-phosphorylation at tyrosine 394 (Y394). Phosphorylated Lck (Y394) is the active kinase used for subsequent downstream signaling.

Figure 4:
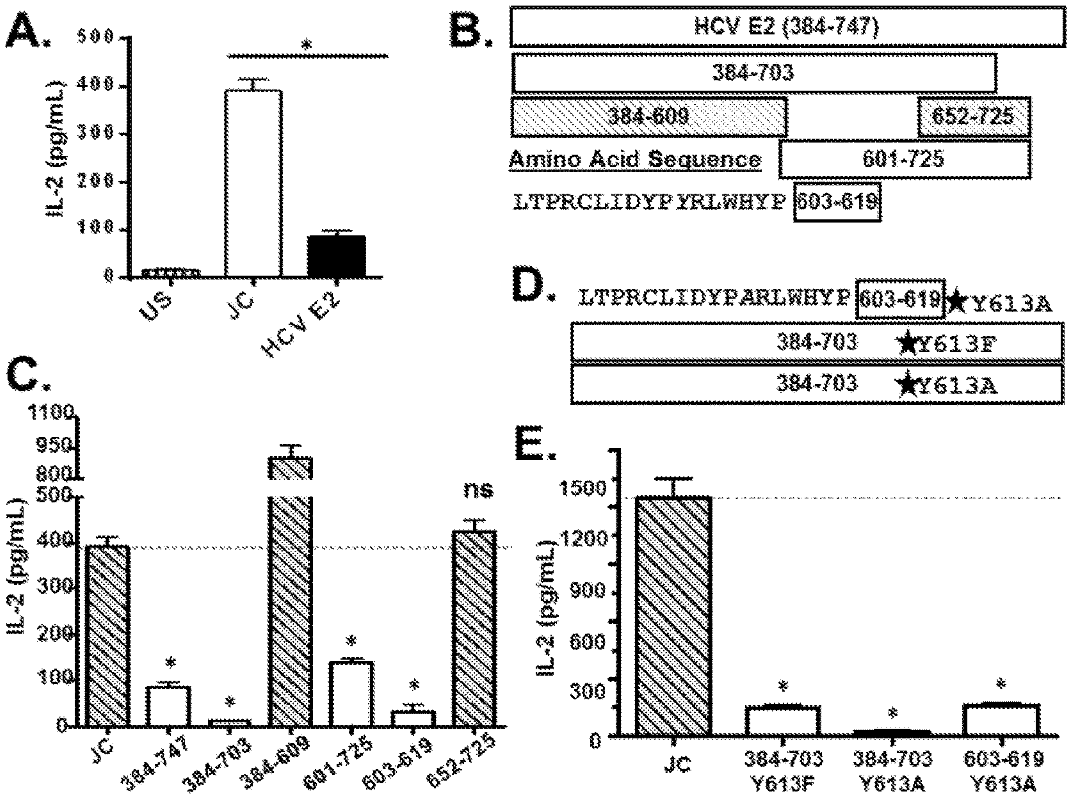
FIGS. 4A-E. HCV envelope protein E2 inhibits T cell receptor (TCR)-mediated signaling. Jurkat control cells (JC) or Jurkat cells stably expressing HCV E2 protein were stimulated with anti-CD3 and anti-CD28. Twenty-four hours later, IL-2 release (FIG. 4A) was measured. Phosphorylation and activation of the lymphocyte specific tyrosine kinase (Lck Y394.

Following TCR stimulation, Lck phosphorylation (Y394) was reduced in Jurkat cells expressing HCV E2 protein compared to controls (FIG. 13B). Activated Lck is needed for activation of both zeta-chain-associated protein kinase (ZAP)-70 and the linker for activation of T cells (LAT). Consistent with reduced Lck activation, ZAP-70 and LAT phosphorylation were reduced in HCV E2 expressing cells compared to controls (FIGS. 4C-D). This inhibition was not due reduced CD45 and Csk expression levels, as they were similar in HCV E2 expressing cells and control cells (FIGS. 14A and 14B, respectively).

To characterize HCV E2 region(s) required for inhibition of TCR signaling, a series of Jurkat cell lines expressing truncated E2 proteins were generated (FIG. 13C). HCV E2 expression in individual cell lines was comparable (FIG. 15A). IL-2 release following TCR stimulation was reduced in all cell lines expressing an E2 fragment containing aa 603 to 619 (FIG. 4E). In contrast, IL-2 release was not inhibited in cells expressing HCV E2 protein that did not contain this region.

Using kinase-specific phosphorylation substrate prediction models, the tyrosine at HCV E2 aa 613 (Y613) was predicted to be an Src/Lck substrate (FIG. 13C) (Xue et al., 2008). This region (aa 603-619) is highly conserved and the Y613 is conserved in more than 600 isolates representing all HCV genotypes (world-wide-web at hcv.lanl.gov). Previous studies found that a conserved tyrosine in the related human Pegivirus (HPgV) is needed TCR-signaling inhibition, and mutation of this residue restores TCR signaling (Bhattarai et al., 2013). Thus, HCV E2 Y613 was mutated to alanine (Y613A) in the context of the peptide (HCV aa 603-619), or to alanine or phenylalanine (Y613A, Y613F) in the context of the E2 protein with the C-terminal transmembrane domain truncated (FIGS. 13D, 15A-B). Y613 mutation did not restore TCR signaling following TCR stimulation (FIG. 4E).

To determine if E2 protein was required for TCR inhibition, a Jurkat cell line expressing HCV E2 RNA coding sequences with a frame-shift mutation was generated. This cell line expressed HCV E2 RNA, but not E2 protein (FIGS. 15A-B). Surprisingly, expression HCV E2 RNA was sufficient to inhibit TCR signaling (FIGS. 5A-B). Thus, E2 RNA encoding aa 603-619 was required and sufficient for inhibition of T cell activation mediated by TCR engagement.

HCV has considerable sequence diversity among isolates, including the sequences encoding E2 aa 603-619 (world-wide-web at hcv.lanl.gov). The HCV E2 RNA and protein expression from a different HCV isolate (genotype 3; GT-3), containing 13 nt differences in the RNA coding aa 603-619 were examined (FIG. 5C). Like GT-2a, GT-3 E2 RNA inhibited TCR-mediated IL-2 release (FIG. 5A). Despite some sequence diversity, 4 cytosine residues are conserved in more than 600 HCV isolates representing all genotypes (FIG. 5C). A Jurkat cell line expressing a HCV E2 RNA was generated having the cytosine residues mutated to adenosine (FIG. 5C), and TCR signaling as measured by IL-2 release and phosphorylation of Lck following anti-CD3/CD28 was restored in cells expressing this mutation (FIGS. 5A-B).

Figure 16:
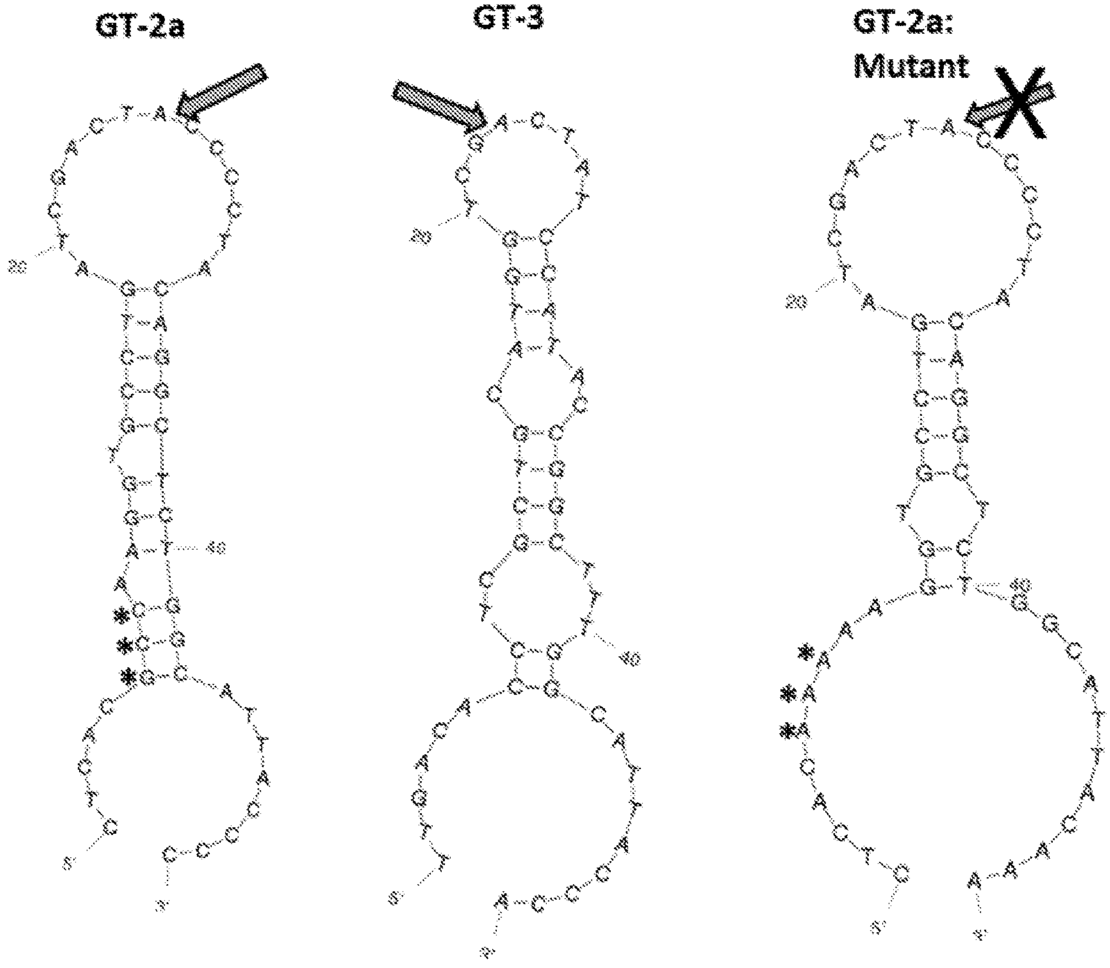
FIG. 16. Predicted structure and Dicer cleavage sites for HCV E2 RNA motif that inhibits proximal TCR signaling (GT-2a=SEQ ID NO: 7; GT-3=SEQ ID NO: 8; GT-2a mutant=SEQ ID NO: 9).

Bioinformatics analyses predicted the conserved nucleotides within the HCV E2 603-619 coding RNA sequences are needed to generate an RNA structure that would be processed by Dicer, the cytoplasmic endoribonuclease involved in the microRNA (miRNA) pathway (FIG. 16) (Ahmed et al., 2013). Mutation of the conserved cytosines that rescued TCR signaling resulted into RNA structure that did not fold into a Dicer substrate (FIG. 16). Previous studies identified interactions between HCV RNA and miRNA pathway including Dicer (Shimakami et al., 2012 and Randall et al., 2007) and HCV virus-derived, small RNAs (vd-sRNAs) are found in HCV infected cells, including RNAs from the E2 coding region (Parameswaran et al., 2010). To determine if vd-sRNAs were present in E2 expressing cells, total cellular RNA was analyzed for the presence of small, E2 derived RNAs as described in the Methods. Following amplification and sequence analysis of RNA species present in these cells, a vd-sRNA containing the T cell inhibitory RNA region encoding HCV E2 aa 590-621 was identified (FIG. 5D). Thus, full length HCV E2 RNA was processed into TCR inhibitory vd-sRNAs in these cells.

Figure 17:
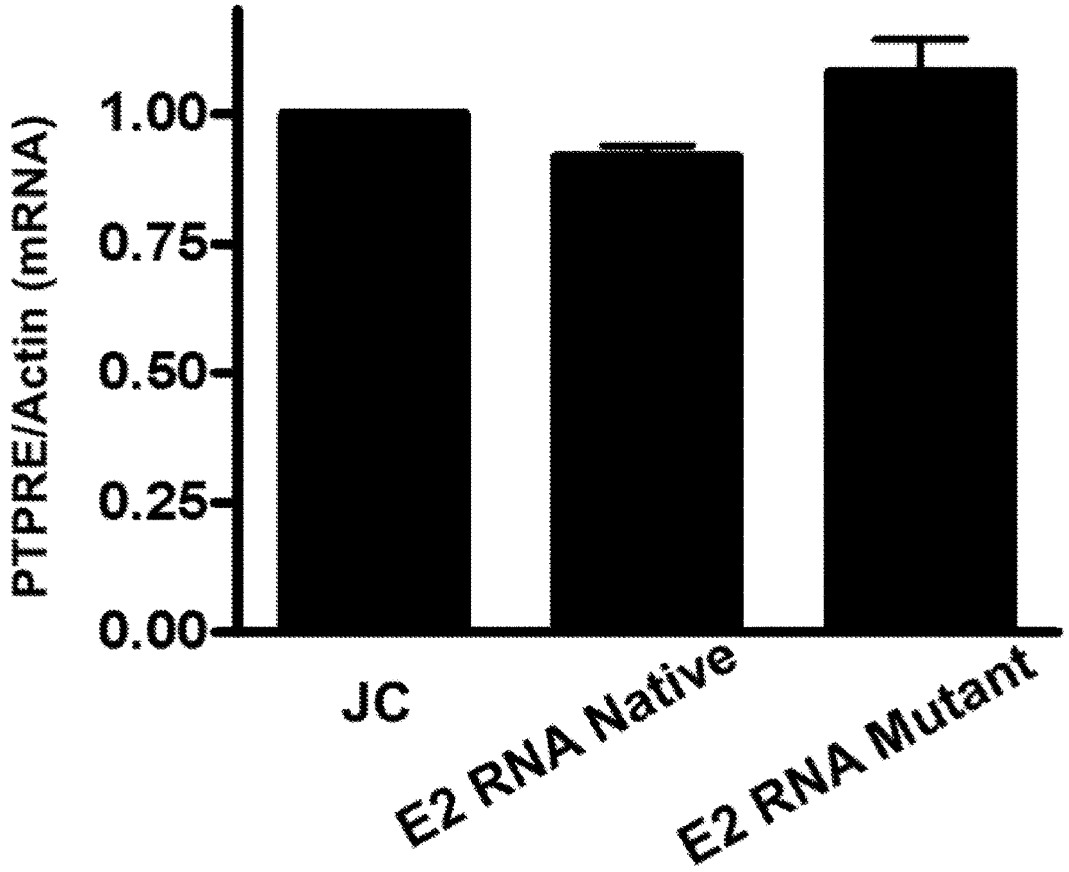
FIG. 17. PTPRE mRNA is not altered by HCV E2 RNA.

To understand the mechanism by which vd-sRNA inhibits TCR signaling, additional analyses were performed to identify potential targets for this vd-sRNA sequence. Two conserved sites complementarity to vd-sRNA were found within the 3' untranslated region (UTR) of a protein tyrosine phosphatase type E (PTPRE; FIG. 6A). PTPRE regulates Src family kinases, of which Lck is a member (Lewis et al., 2005; Roskoski, 2005; Gil-Henn and Elson, 2003; Granot-Attas et al., 2009 and Toledano-Katchalski and Elson, 1999). PTPRE mRNA expression levels were similar in control and HCV E2 RNA expressing cells (FIG. 17); however, Jurkat cells expressing E2 RNA had significantly reduced PTPRE protein levels compared to controls (FIG. 15B). The upper band represents the full-length PTPRE with transmembrane domain (isoform 1) and the lower band represents cytoplasmic PTPRE (isoform 2) (FIG. 15B). Mutation of the conserved nucleotides in E2 RNA to remove the predicted Dicer substrates restored PTPRE protein expression (FIG. 6B) and TCR signaling (FIGS. 5A-B). PTPRE protein levels were also reduced in human hepatoma (Huh) cells containing full length HCV RNA in replicons (FL) compared to parent Huh cells or Huh7 containing HCV replicons expressing only nonstructural proteins (NS) (FIG. 6B).

To determine the specificity and HCV E2 coding RNA requirements for PTPRE knockdown, the PTPRE 3'UTR sequence was inserted into the 3'UTR of GFP in an expression plasmid. GFP expression in 293T cells was reduced by co-transfection of HCV E2 coding plasmid compared to GFP without PTPRE 3'UTR (FIG. 6C). Furthermore, incubation of 293T cells in HCV RNA containing serum led to reduced GFP expression compared to cells incubated in control (HCV RNA negative) serum (FIG. 6D). Thus, HCV RNA encoding envelope E2 directly targets PTPRE and inhibits its expression.

To further examine the specificity of the HCV E2 RNA for targeting cellular genes, the predicted seed sequence for PTPRE was replaced with a sequence targeting a cellular gene expressed in the Jurkat cells (CXCR4) (FIG. 6E). A Jurkat cell line was generated as before, and CXCR4 expression were examined. Replacing PTPRE targeting sequence with CXCR4 significantly reduced CXCR4 expression (FIG. 6F).

Together, these data demonstrate that HCV E2 RNA expressed in vitro is processed into short RNA that inhibits PTPRE expression in human hepatocyte (Huh 7) and T (Jurkat) cells, and inhibits TCR-mediated Src (Lck) signaling. Addition of HCV RNA-containing serum to 293 cells also inhibits PTPRE expression, thus this effect is highly likely to be biologically relevant.

Together, these data demonstrate that HCV E2 RNA expressed in vitro is processed into short RNA that inhibits PTPRE expression in human hepatocyte (Huh 7) and T (Jurkat) cells, and inhibits TCR-mediated Src (Lck) signaling. Addition of HCV RNA-containing serum to 293 cells also inhibits PTPRE expression, thus this effect is highly likely to be biologically relevant.

HCV E2 Protein Inhibits Distal TCR Signaling.

T cell activation can be initiated in vitro by stimulating downstream of TCR using phorbol-12-myristate-13-acetate (PMA) and ionomycin (P+I). To determine if HCV E2 RNA inhibited proximal and distal TCR-mediated signaling, Jurkat cells were stimulated with P+I, and cells expressing just HCV RNA did not inhibit distal signaling (FIG. 7A). Thus, the viral RNA was specific for proximal signaling inhibition.

Figure 18:
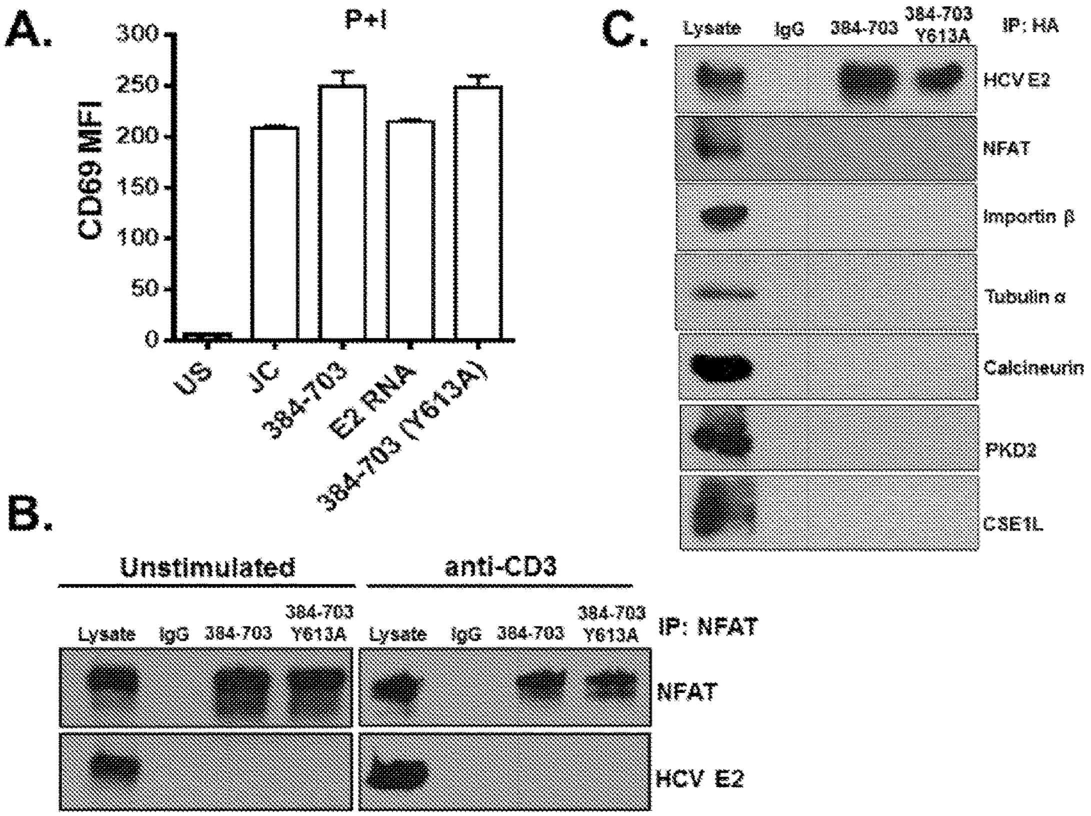
FIGS. 18A-C. HCV E2 protein, signaling to CD69, and interactions with NFAT regulatory molecules.
Figure 19:
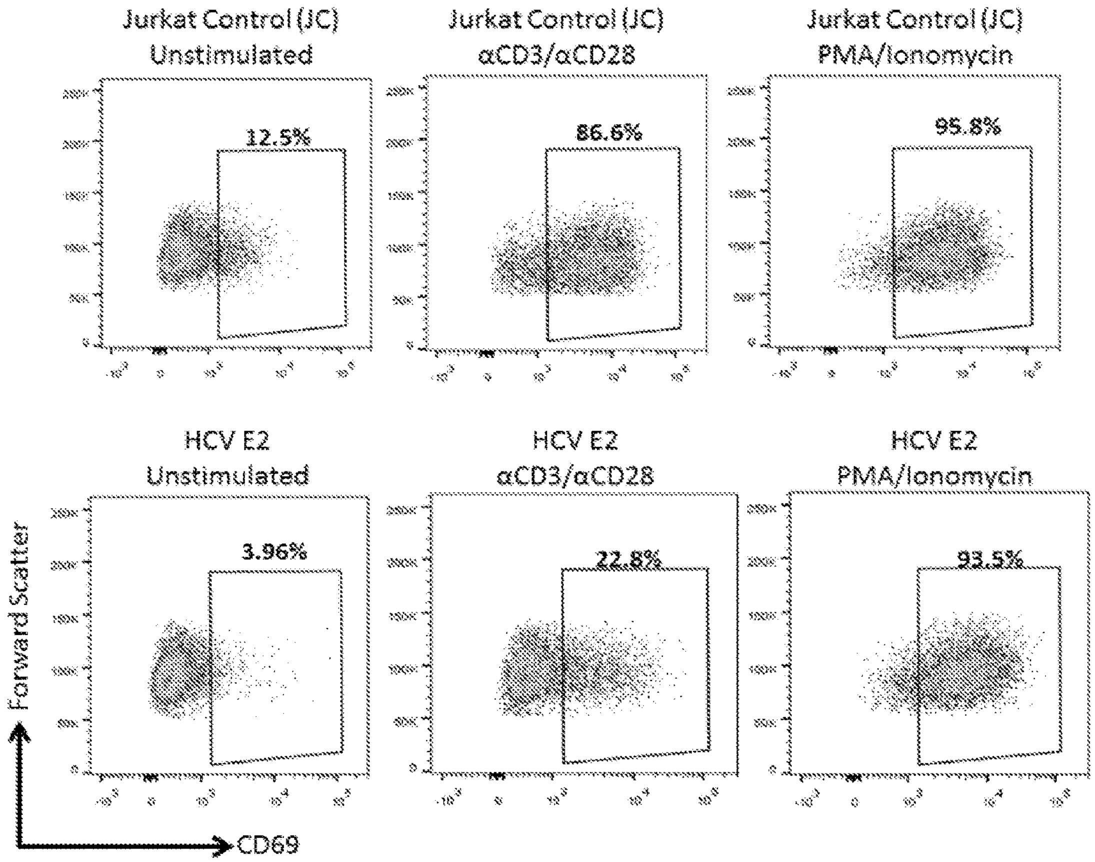
FIG. 19. HCV E2 protein inhibits proximal, but not distal activation of CD69.
Figure 20:
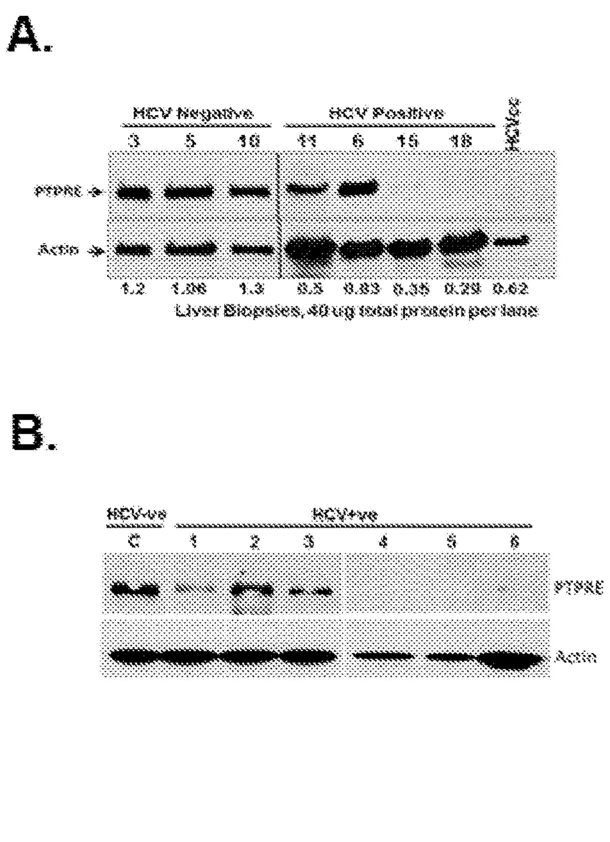
FIGS. 20A-B. HCV E2 vsRNA-1 expression inhibits PTPRE in vivo. PTPRE protein levels in representative liver biopsy (FIG. 20A) and peripheral blood mononuclear cell samples (PBMCs, FIG. 20B). Control liver tissue (HCV negative) represents liver biopsies from individual with other forms of liver disease but without HCV infection. Control PBMCs ($HCV^{+}$) are from healthy donors who are not infected with HCV, HIV, or HBV (FIG. 20B). Actin housekeeping gene controls demonstrate the amount of cellular protein loaded in the gel.
FIG. 20C shows the ratio of PTPRE to Actin in liver tissues from HCV negative and positive people, and PTPRE:Actin ratio in PBMCs from additional HCV infected subjects.

Surprisingly, HCV E2 protein expression with (aa 384-747), and without (aa 384-703) the transmembrane domain inhibited distal signaling following P+I activation (FIG. 7A). Inhibition was specific for the NFAT pathway, as P+I stimulation did not inhibit CD69 expression in either HCV E2 RNA or E2 protein expressing cells (FIGS. 18A and 19). Near full length E2 (384-703) was required, as Jurkat cells expressing truncated E2 (384-609) or (601-725) did not inhibit distal signaling (FIG. 7A). The conserved E2 Y613 was also required, as mutation of the predicted Lck substrate site (Y613F, Y613A) in the context of the near full-length protein restored P+I-mediated IL-2 release (FIG. 7A).

The Y613 of HCV E2 protein is a predicted Lck substrate, thus phosphorylation of this residue was tested. In vitro recombinant HCV E2 was phosphorylated by Lck and dephosphorylated by CD45 (FIG. 7B), and HCV E2 expressed in Jurkat cells was phosphorylated following TCR stimulation (FIG. 7C). Thus, HCV E2 served as an Lck substrate and phosphorylation occurred at Y613, as the Y613A mutant was not phosphorylated following TCR engagement (FIG. 7C). To assess the role of Lck mediated phosphorylation of HCV E2 in NFAT signaling, Jurkat cells were treated with Lck inhibitor overnight. P+I mediated IL-2 release was rescued in HCV E2 expressing cells treated with Lck inhibitor suggesting Lck-mediated phosphorylation of HCV E2 at Y613 was required to inhibit distal TCR signaling (FIG. 7D). Together, these data identified a novel role of T cell specific kinase Lck in phosphorylating conserved tyrosine (Y613) on HCV E2 for inhibition of E2 mediated distal TCR signaling.

Figure 8:
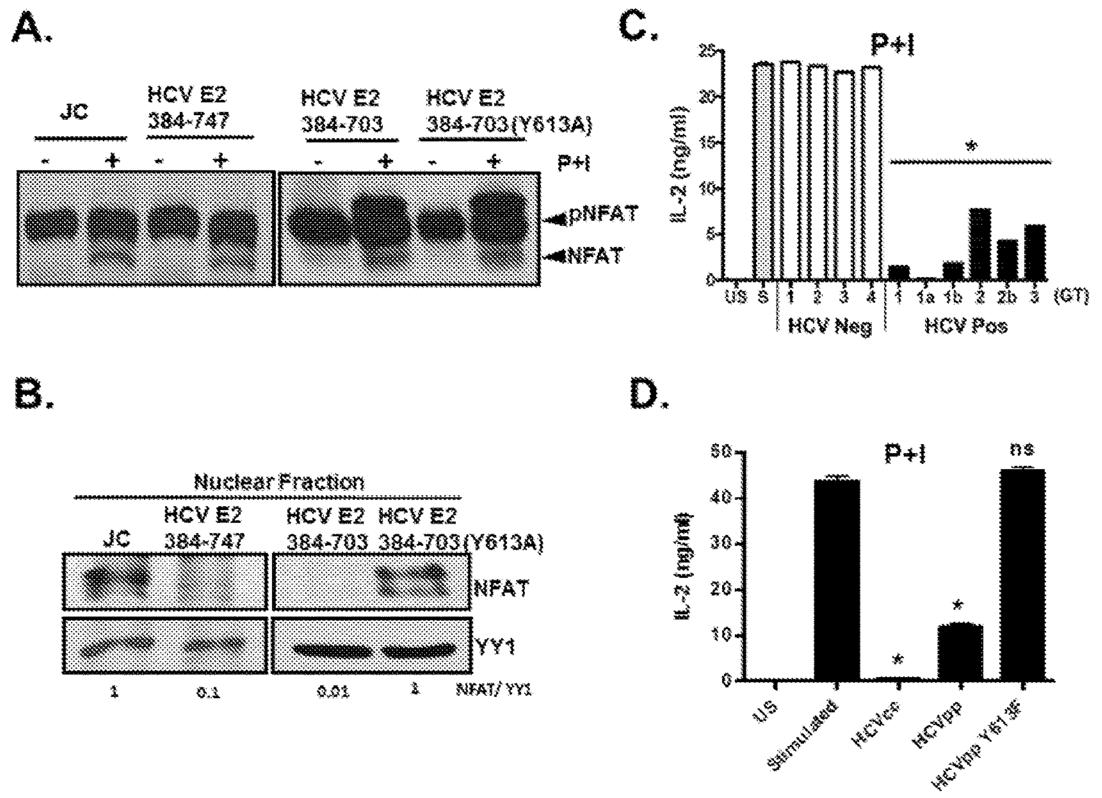
FIGS. 8A-D. HCV E2 protein inhibits NFAT nuclear translocation. Dephosphorylation (FIG. 8A) and nuclear translocation (FIG. 8B) of the nuclear factor of activated T cells (NFAT) in Jurkat control cells or HCV E2 expressing cells as determined by immunoblot. The nuclear transcription factor Yin Yang 1 (YY1) served as the loading control for nuclear localization. P+I mediated IL-2 was release from primary healthy donor peripheral blood mononuclear cells (PBMCs) incubated with serum obtained from HCV positive (HCV+) humans infected with genotype (GT; 1, 1a, 1b, 2, 2b, and 3) HCV negative (HCV−) human subjects (C1-C4) (FIG. 8C) or cell-culture derived HCV particles (HCVcc) and retroviral particles pseudotyped with HCV envelope (E1-E2; HCVpps) or with HCV envelope containing the Y613F mutation (HCVpp Y613F) (FIG. 8D). US=unstimulated, and S=stimulated (no serum). Data represent the average of three technical replicates. The standard deviation is shown. Each study was repeated with different donors with consistent results. *P<0.01.

To determine the mechanism by which phospho-HCV E2 inhibited P+I induced IL-2 release, the activation and nuclear translocation of the nuclear factor of activated T cells (NFAT), a transcription factor required for IL-2 mRNA transcription was assessed. Upon P+I stimulation, NFAT was activated (dephosphorylated) similarly in control and HCV E2 protein expressing Jurkat cells (FIG. 8A). However, nuclear translocation of active NFAT was reduced in HCV E2-expressing cells compared to that in control cells (FIG. 8B). Since Y613 on E2 protein was phosphorylated by Lck and phospho-HCV E2 was required for reduced nuclear translocation of NFAT, interaction between NFAT and phosphorylated HCV E2 protein was assessed. HCV E2 protein did not precipitate NFAT in either unstimulated or TCR stimulated Jurkat cells (FIG. 10C). NFAT nuclear import and export is regulated by large number of cellular proteins and non-coding RNAs, including importin-β, tubulin-α, calcineurin, protein kinase D2 (PKD2), CSE1L, and others (Sharma et al., 2011). No direct interaction between E2 or phospho-E2 with the factors studied to date was observed in immune precipitation studies (FIG. 18C). These data suggest HCV E2 upon phosphorylation at Y613 by Lck inhibits NFAT nuclear translocation resulting into impaired distal TCR signaling.

Next, the effect of HCV enveloped particles on distal TCR signaling in primary human T cells was assessed. Following P+I stimulation, IL-2 release from healthy human PBMCs was inhibited by HCV particles obtained from serum (FIG. 8C), and by infectious and defective HCV particles (HCVcc and HCVpp, respectively) (FIG. 8D). Since mutation of Y613 to phenylalanine (Y613F) reversed the HCV E2-mediated inhibition of distal TCR signaling in Jurkat cells (FIG. 7A), retroviral particles were pseudotyped with native E1-E2 or E1-E2 with the Y613F mutation (HCVpp Y613F). IL-2 release was restored in cells incubated with the Y613F mutant following P+I stimulation of healthy PBMCs (FIG. 8D). Together, these data identify a single residue (Y613) on HCV envelope protein that is essential for inhibition of distal TCR signaling.

Taken together, these data confirm that HCV RNA-containing serum, HCVcc, HCVpp, HCV E2 protein, but not HCV E2 RNA inhibit distal TCR signaling in primary human T cells and the CD4+ human T cell line. This inhibition requires Lck phosphorylation of Y613 of HCV E2 protein, and does not require viral replication, as HCVpp inhibit distal signaling.

Yellow Fever Virus (YFV) RNA and Envelope Proteins Inhibit T Cell Signaling.

Figure 21:
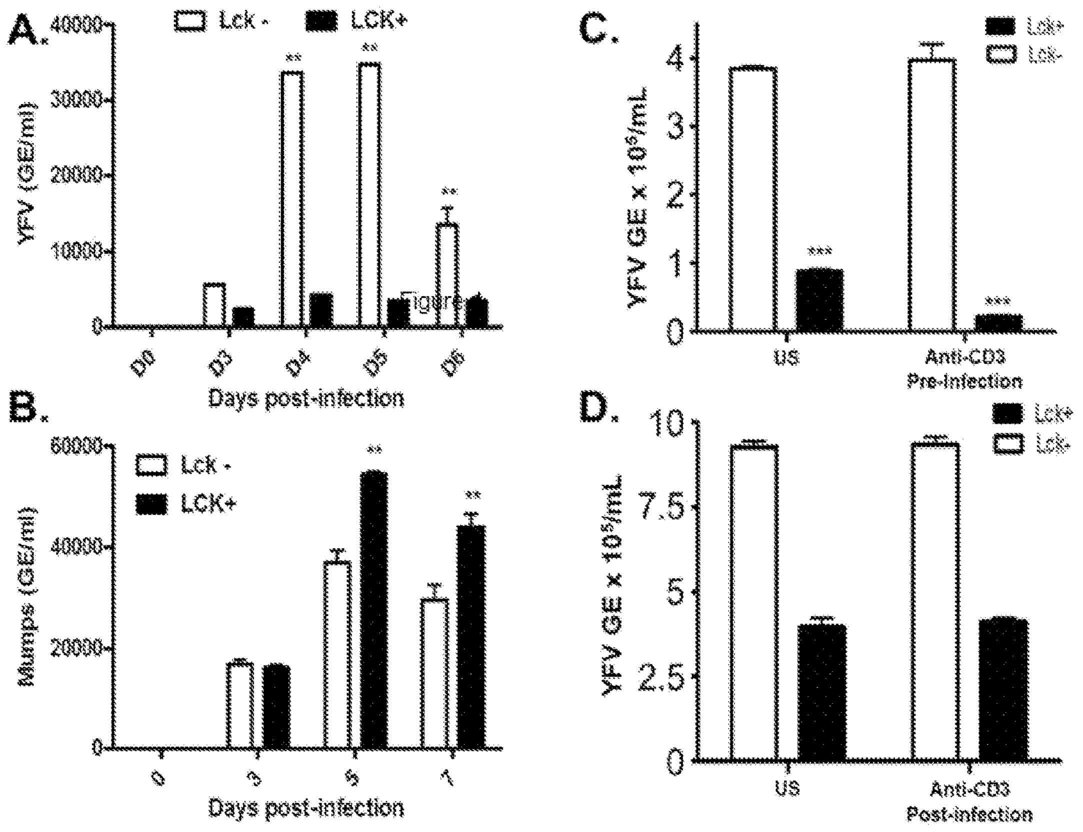
FIGS. 21A-D. Effect of Lck deficiency on YFV and mumps virus replication. YFV (vaccine strain 17D) replicated well in cells lacking Lck (JCAM (Lck−), but less well in Jurkat cells expressing Lck (Lck+) (FIG. 21A), while mumps replicated in Jurkat cells with and without Lck (FIG. 21B). Activating T cells prior to infection resulted in reduced YFV replication (FIG. 21C), and infecting prior to activation suppressed further replication (FIG. 21D).
Figure 22:
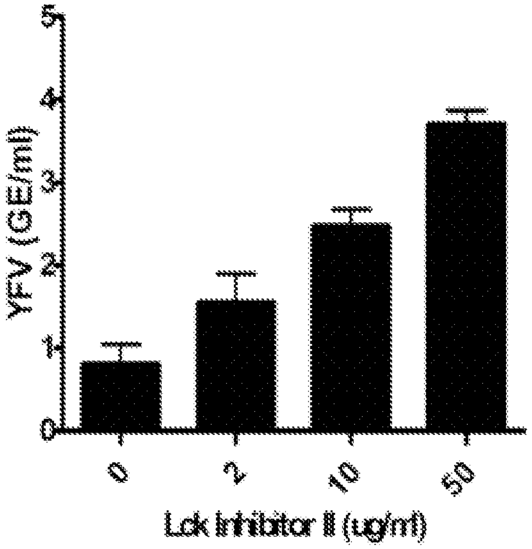
FIG. 22. Inhibition of Lck resulted in enhanced YFV replication. GE/mL=genome equivalents/mL. GE correlates well with infectivity as measured by $TCID_{50}$ assays.

A major problem with the HCV and GBV-C studies are that neither virus replicates well in vitro, and although HCV is found in lymphocytes in vivo, it does not replicate extensively in lymphocytes. We previously showed that the vaccine strains of YFV (17D) and mumps (Jeryl Lyn) strains replicate in PBMCs and CD3+ (T) cells in vitro (Xiang et al., 2009; Mohr et al., 2008). Bioinformatic analyses revealed that both viruses have conserved motifs predicted to serve as a substrate for Lck (Xue et al., 2011). To examine a potential interaction with Lck, we first studied replication of YFV and mumps in Jurkat cells with and without Lck. YFV produced less virus in the presence of Lck, while mumps replicated to higher level in Lck containing cells (FIGS. 21A-B). Stimulation of TCR with anti-CD3 prior to YFV reduced replication in cells expressing Lck (FIG. 1C), and anti-CD3 activation after YFV infection blocked further replication (FIG. 21D). The process was dependent on Lck activity, as Lck inhibition with either an Lck inhibitor or siRNAs significantly increased YFV replication in TCR-stimulated primary human cells (FIG. 22).

Figure 23:
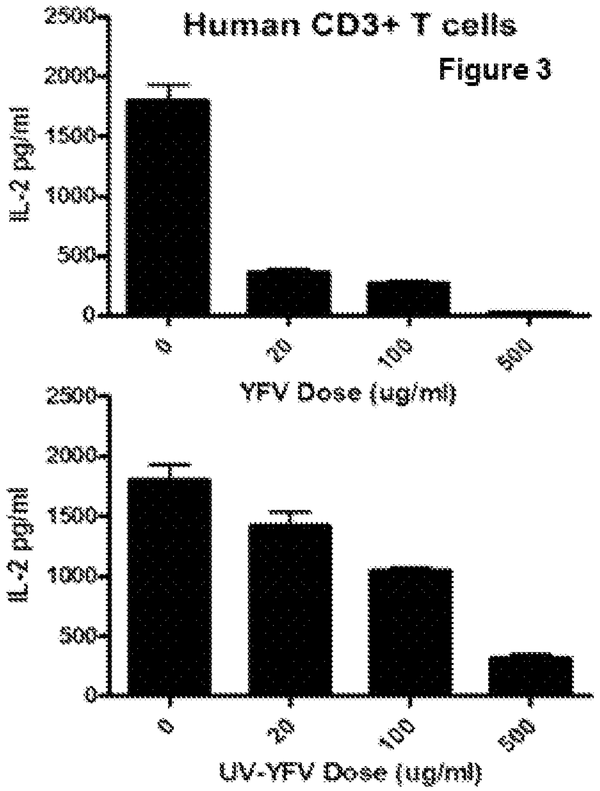
FIG. 23. IL-2 released by primary human T cells following TCR stimulation (anti-C3/CD28) in cells infected with YFV or incubated with UV-inactivated YFV.
Figure 24:
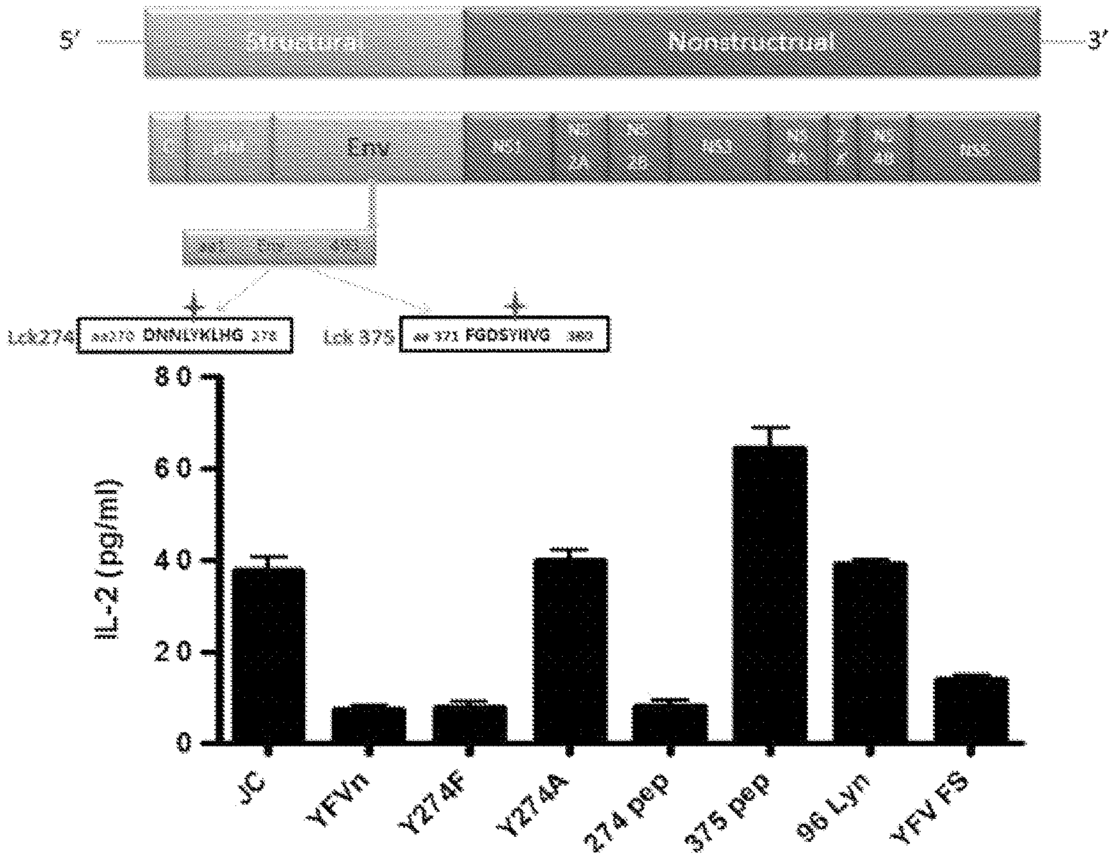
FIG. 24. YFV genome organization is shown, with Envelope (red) and two conserved tyrosines predicted to be Lck substrates shown. IL-2 response post anti-CD3/CD28 stimulation is shown for the Jurkat cell controls (JC), the native YFV envelope YFVn, the full-length env with Y274F and Y274A mutations, peptides containing predicted Lck substrate sites (274 pep; 35 pep), a peptide containing a predicted Lyn site (96 Lyn), and the YFV envelope coding region with a frame shift that expresses RNA, but not YFV envelope protein (YFV FS).
Figure 25:
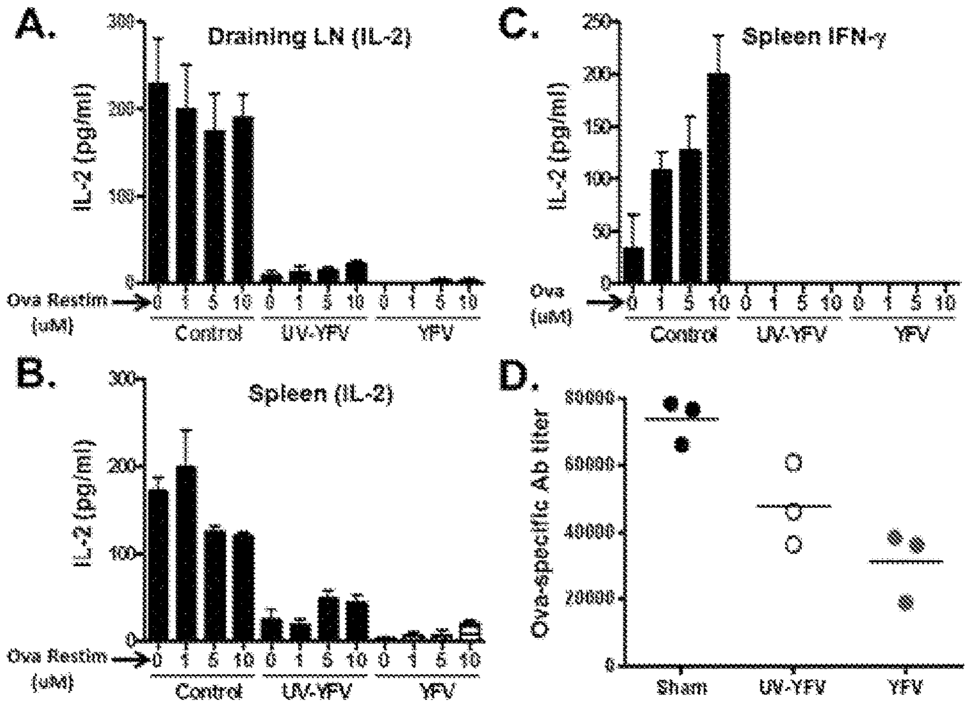
FIG. 25. Effects of YFV infection in mice. Mice were immunized with control media, UV-inactivated YFV or infectious YFV as described in the text. Spleen and draining lymph nodes were removed after the ova-alum immunization and boost as described, and stimulated ex vivo with ova at the concentrations noted. IL-2 and IFN-γ release from the different tissues are shown and had opposite effect. YFV reduced cytokine secretion. Ova-specific antibodies were also reduced in YFV immunized mice.
Figure 26:
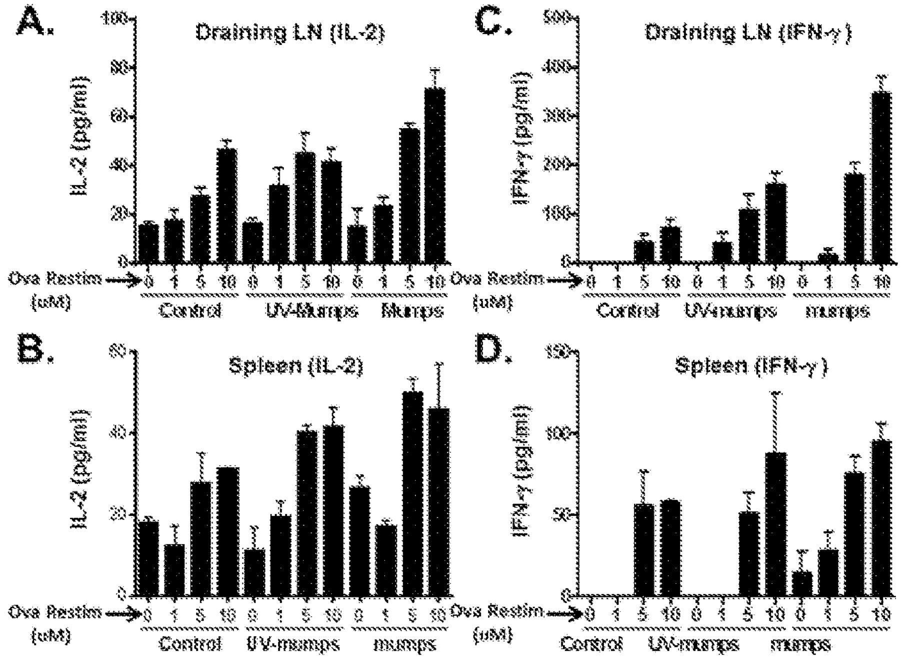
FIG. 26. Effects of mumps infection in mice. Mice were immunized with control media, UV-inactivated mumps or infectious mumps virus as described in the text. Spleen and draining lymph nodes were removed after the ova-alum immunization and boost as described, and stimulated ex vivo with ova at the concentrations noted. IL-2 and IFN-γ release from the different tissues are shown and had opposite effect. Mumps increased cytokine secretion.
Figure 27:
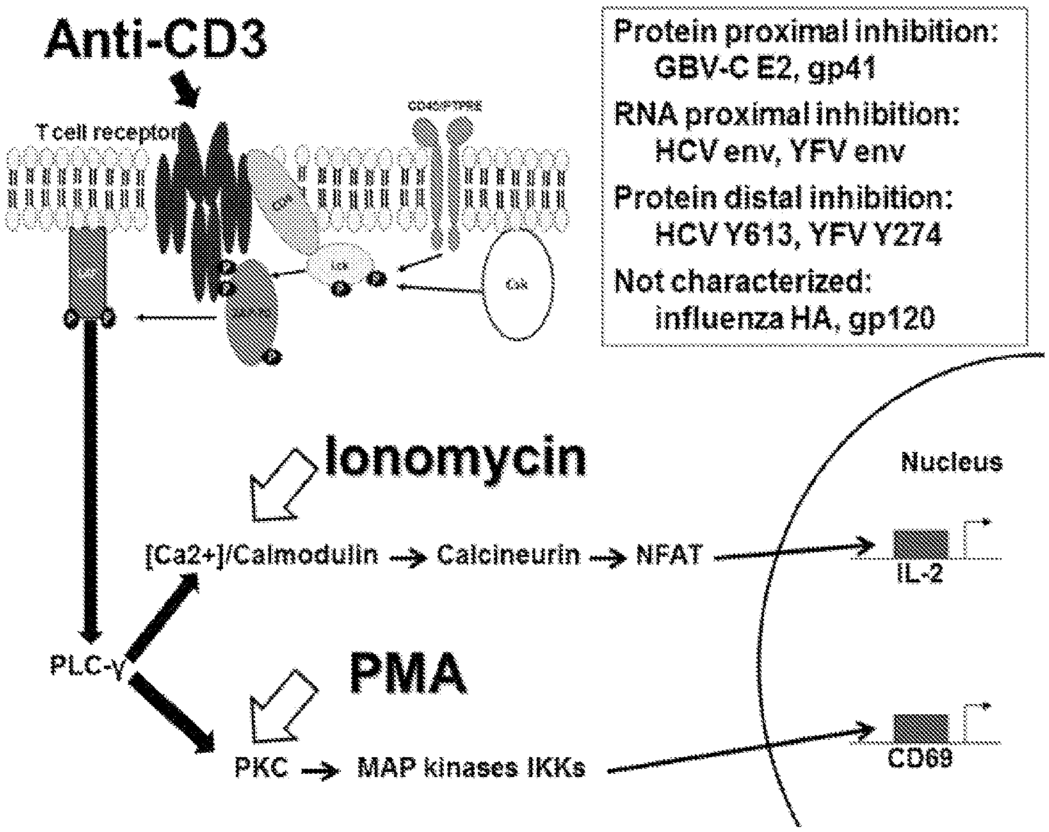
FIG. 27. Summary of findings of viral envelope protein and RNA interactions with TCR signaling pathways. Protein and RNA (HCV, YFV, GBV-C, HIV 41) inhibit proximal signaling while protein and Lck reduce distal TCR signaling.

YFV infection of primary human CD3+ (T) cells prior to anti-CD3 activation reduced TCR-signaling as measured by IL-2 release (FIG. 23). Of note, replication was not required for this TCR inhibitory effect, as UV-inactivated YFV with no measurable infectivity also inhibited TCR signaling in this assay, but to a lesser extent (FIG. 23). An infectious YFV clone was obtained, and the envelope coding region was amplified and expressed it in the tet-off expression system. Like HCV, there are 2 conserved tyrosines predicted to serve as Lck substrates Y274 and Y375 (FIG. 24). Y274 was required for inhibition. Like HCV, YFV inhibited both proximal (TCR-mediated) and distal TCR (P+I-induced) signaling. Thus, we made a frameshift construct and found that like HCV, env-encoding RNA inhibited proximal signaling (FIG. 24). Of note, mutation of a single nucleotide in the RNA coding region (in the Y274F mutant) did not restore proximal signaling, yet mutation of two residues (in the Y274A mutant) did (FIG. 24). Surprisingly, analysis of the coding sequence at Y274 reveals homology with the same phosphatase regulated by HCV env (PTPRE). These data are very new, and I am in the process of validating the presence of viral-derived short RNAs in infected cells.

Figure 5:
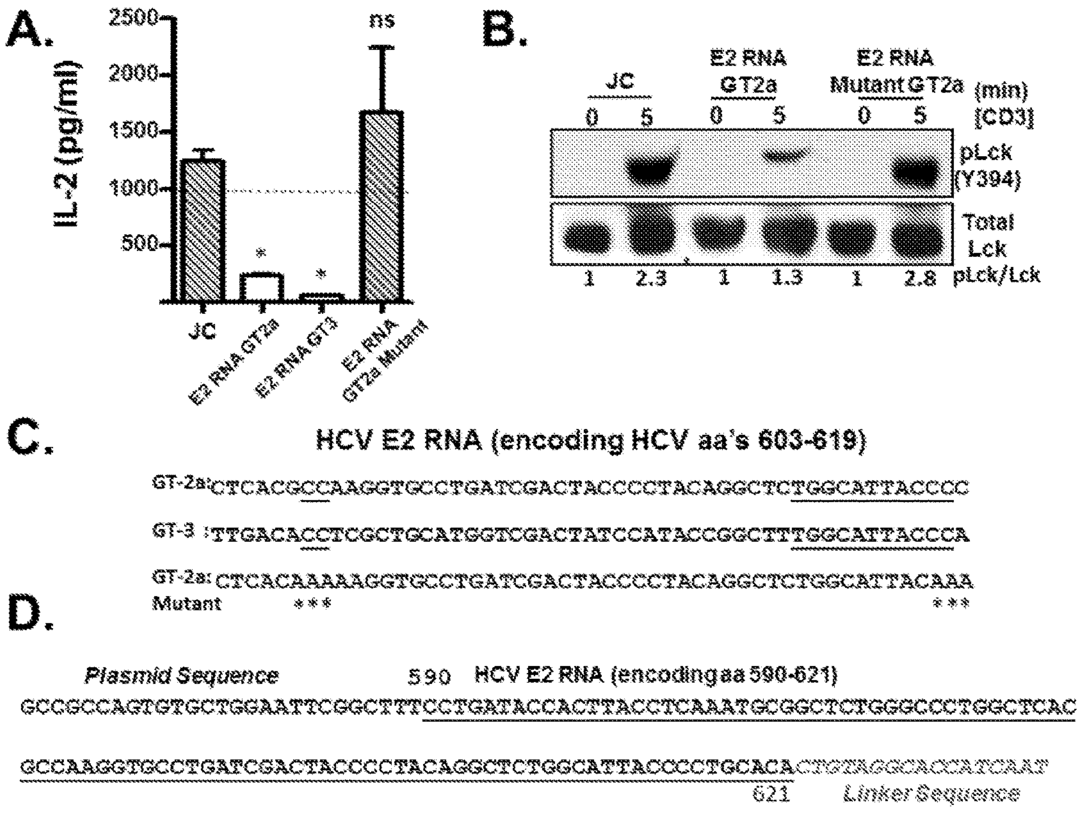
FIGS. 5A-D. HCV envelope (E2) coding RNA is sufficient to inhibit proximal T cell receptor (TCR) signaling. Jurkat cells were generated that stably expressed HCV envelope (E2) RNA (coding aa 384-703) with a frame-shift mutation to abolish protein expression from isolates belonging to genotype (GT) 2a and GT3, or the GT 2a sequence in which four cytodine residues were changed to alanine residues. TCR induced IL-2 release from these Jurkat cells were measured after 24 hour stimulation with anti-CD3/CD28 (FIG. 5A). Activation of lymphocyte specific tyrosine kinase (Lck) was measured by immunoblotting for phosphoY394 following anti-CD3 stimulation (FIG. 5B). Total Lck served as the loading control. The RNA sequence of the HCV E2 (aa 603-619) coding region from the different HCV genotypes (GT) and mutants are shown in FIG. 5C (GT-2a=SEQ ID NO: 7; GT-3=SEQ ID NO: 8; GT-2a mutant=SEQ ID NO: 9). Conserved sequences are underlined and mutations introduced into the GT 2a sequence noted by * (FIG. 5C). Small RNAs were amplified following 3'-linker ligation and specific cDNA synthesis. Small RNAs were cloned and sequenced, and the HCV E2 region encoding (aa 590-621) was detected in Jurkat cells expressing HCV E2 protein.
Figure 6:
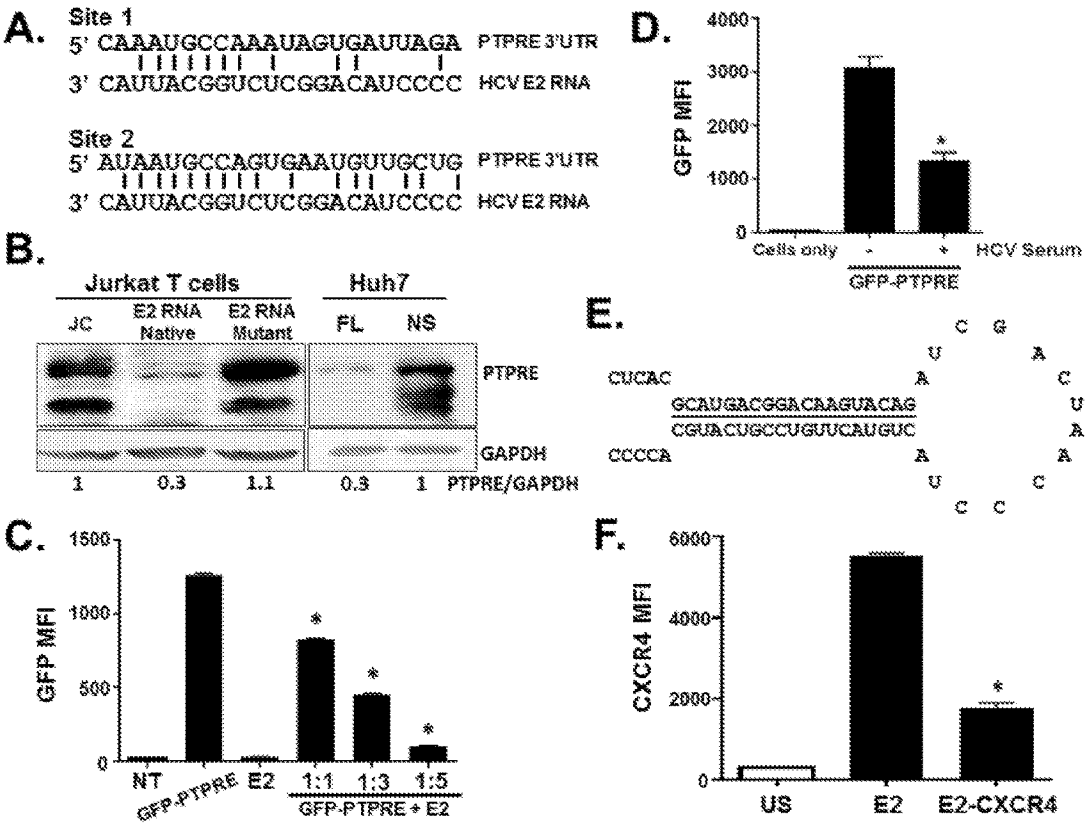
FIGS. 6A-F. HCV E2 RNA inhibits protein tyrosine phosphatase receptor type E (PTPRE) expression. Sequence alignment of two sites within PTPRE 3' untranslated region (UTR) predicted to bind to HCV E2 RNA (aa 603-619) region (FIG. 6A; Site 1—PTPRE 3'UTR=SEQ ID NO: 11, HVC E2 RNA=SEQ ID NO: 12; Site 2—PTPRE 3'UTR=SEQ ID NO: 13, HVC E2 RNA=SEQ ID NO: 14). Immunoblot analysis of PTPRE protein levels in control, HCV E2 RNA or HCV E2 mutant RNA expressing Jurkat cells, or Huh7 cells expressing full length HCV replicon (FL) or non-structural protein (NS) expressing replicon. The upper band represents full-length PTPRE with transmembrane domain (isoform-1) and lower band represents cytoplasmic PTPRE (isoform-2). GAPDH serves as a loading control (FIG. 6B). GFP expression by HEK 293 cells co-transfected with 1 μg of plasmid DNA encoding GFP alone or GFP with PTPRE 3'UTR sequence shown in panel A and 5 μg of plasmid DNA encoding HCV E2 (FIG. 6C) or incubated with HCV-positive serum (FIG. 6D) and GFP expression measured after 72 hours. Data represent the average of three technical replicates and each study was repeated at least three times with consistent results. The region of HCV E2 targeting PTPRE was replaced with sequences targeting the cellular chemokine receptor CXCR4 (FIG. 6E; SEQ ID NO: 15), and a Jurkat cell line stably expressing this sequence was generated. CXCR4 was reduced in Jurkat cells expressing this HCV E2 sequence targeting CXCR4, but not Jurkat cells expressing the native HCV E2 RNA sequence (FIG. 6F). *P<0.01.

Mice were immunized IP with either YFV or mumps virus. Initial studies were in Balb/C mice; however, studies were repeated in C57/black 6 mice with similar results. All data shown are in black 6 mice. Stock viruses were both produced in Vero cells. Experiments were controlled by immunizing with sham infected Vero cell culture supernatant. In addition, UV-inactivated YFV and mumps virus were tested. The viral titer (prior to inactivation) and protein concentrations of the different inocula were normalized. Following IP immunization with YFV, TCR-activation of splenocytes was measured longitudinally for 18 days, and TCR signaling was found to decrease by day 4, reach the nadir at day 10-12, and then increase by day 18—though not to baseline. Subsequently, after YFV immunization ovalbumin (in alum) was administered, and 7 days later a second dose of ova in alum was given. Animals were sacrificed 7 days after the boost, and splenocytes and draining lymph nodes were examined for immune responses. Mice immunized with YFV had significantly reduced IL-2, IFN-γ, and ova-specific antibodies compared to the cell culture controls (FIGS. 5-6). These studies have been repeated twice, and in all studies the effects were reproducible. Because of concern that immunization with any viral preparation might lead to global impaired immune responses, and the fact that mumps virus enhanced activation in the in vitro system, mice were immunized with mumps vaccine strain (Jeryl Lynn; replication competent and UV-inactivated). The first studyimmunized 3 mice in each group, and cytokine levels increased following ova stimulation ex vivo (IFN-γ and IL-2 shown in FIG. 6; IL-4, IL-13).

Figure 7:
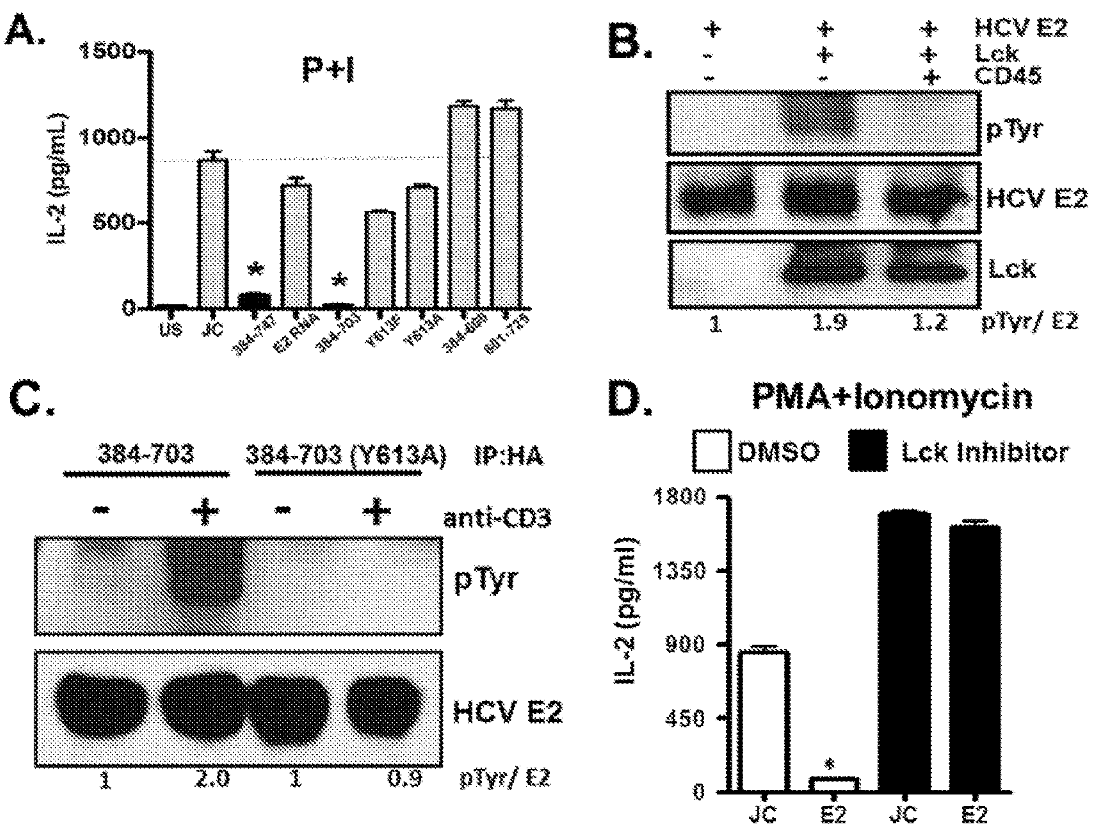
FIGS. 7A-D. HCV E2 protein inhibits distal T cell receptor (TCR) signaling. PMA+Ionomycin (P+I) mediated IL-2 release by Jurkat cells expressing full-length or various truncated or tyrosine 613 mutant HCV E2 protein fragments as indicated (FIG. 7A). Recombinant HCV E2 protein was phosphorylated by Lck in an in vitro kinase reaction, and was dephosphorylated by the CD45 phosphatase (FIG. 7B). HCV E2 protein (native, or Y613A mutant) expressed in Jurkat cells was precipitated before (−) or after (+) TCR stimulation with anti-CD3. E2 and phospho-E2 were detected by immunoblot with E2 specific antibody or anti-phosphotyrosine antibody respectively (FIG. 7C). P+I mediated IL-2 release control Jurkat cells (JC) or HCV E2-expressing Jurkat cells (384-747) which had been incubated in 100 μg/mL Lck inhibitor or the vehicle control (DMSO) (FIG. 7D). Data represent the average of three technical replicates. The standard deviation is shown. Each study was repeated at least three times with consistent results. *P<0.01.

These data indicate that viral envelope coding RNA and env proteins from several viruses interfere with TCR signaling, potentially delaying or reducing env-specific immune responses and facilitating replication. Although HCV and YFV share this phenotype, different mechanisms appear to be utilized by different viruses. FIG. 7 summarizes the data showing the different viral proteins or RNA tested and where they inhibit TCR signaling. Influenza HA and HIV gp120 have been reported to interfere with TCR signaling as well, but the mechanism of these interactions is not studied.

Example 3—Discussion

HCV establishes persistent infection through complex and incompletely understood mechanisms. A strong T cell response correlates with effective control and clearance of HCV infection; however, the majority of infected individuals fail to clear viremia (Rehermann, 2009). Chronic infection is associated with a reduction in HCV-specific intrahepatic and peripheral blood T cells, suggesting that HCV proteins, RNA, or both inhibit T cell function. Here the inventors As disclosed herein, HCV particles directly reduced T cell activation via inhibition of the T cell receptor (TCR) signaling pathway. Serum, HCV RNA-containing EV from HCV-infected individuals and HCVcc inhibited TCR signaling in human T cells. Inhibition of TCR signaling did not require replication, as replication incompetent HCVpp inhibited TCR signaling. The relative inhibition of TCR signaling by HCV positive sera was stronger than cell culture derived HCVcc or HCVpp. This is not surprising, since HCV positive sera contain TCR inhibitory cytokines (IL-10, TGF-β) that are not present in HCVcc, purified EVs and HCVpp (Nelson et al., 1997 and Reiser et al., 1997). Nevertheless, in the absence of these serum factors, HCVcc, HCV positive EVs and HCVpp also inhibited TCR signaling in PBMCs and purified T cells, thus viral E2 protein and RNA were sufficient to alter TCR signaling.

HCV RNA encoding E2 and E2 protein itself independently inhibited TCR signaling at two distinct sites within the TCR signaling pathway. HCV E2 RNA inhibited proximal TCR signaling by reducing activation of Lck, and inhibition required highly conserved nucleotide sequences flanking the conserved E2 Y613. The RNA region contains conserved residues from a structure processed by Dicer into a vd-sRNA. Mutation of four of the conserved residues abolished the predicted RNA secondary structure and restored TCR signaling. Conserved sequences in the vd-sRNA sequence were predicted to target a PTPRE, a phosphatase involved in Src kinase signaling.

PTPRE translation was significantly reduced in lymphocyte cells expressing HCV E2 RNA and in hepatocytes expressing the HCV full-length genome. PTPRE regulates Src signaling through Grb2 (Toledano-Katchalski and Elson, 1999), and Grb2 deficient cells have impaired Lck activation (Jang et al., 2010), suggesting that HCV-derived, short RNA interferes with PTPRE translation leading to reduced TCR signaling. HCV replication in hepatocytes is enhanced by inhibition of Src kinases (Supekova et al., 2008), thus knockdown of hepatocyte PTPRE which regulates Src kinases by this HCV-derived short RNA may also facilitate viral replication in hepatocytes in addition to interfering with T cell signaling in lymphocytes. The addition of HCV RNA-containing serum to 293 cells targeted PTPRE sequences when added to GFP compared to HCV RNA negative serum, illustrating the biological relevance of this observation.

Figure 28:
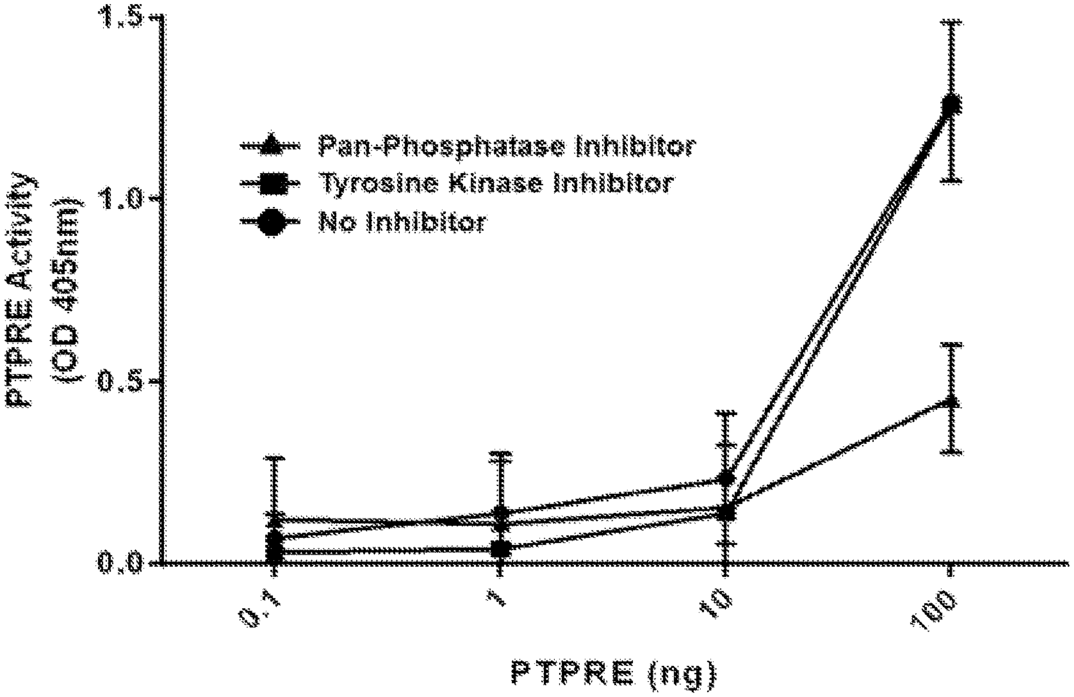
FIG. 28. ELISA based assay of PTPRE activity. Recombinant PTPRE (100 ng) incubated with pNPP substrate for 1 hr at 37° C. in fresh phosphatase dilution buffer. A blank well with everything except active PTPRE was also prepared. Absorbance read at 405 nm, and values represent the PTPRE containing wells minus the blank wells.

Using an ELISA based assay of PTPRE activity, it was shown that a pan-phosphatase inhibitor potently inhibits PTPRE (FIG. 28).

A second mechanism of inhibition of TCR signaling involved E2 protein phosphorylation. Four lines of evidence in the studies herein support a role for Lck-mediated phosphorylation of HCV E2 protein at Y613. First, E2 was phosphorylated in vitro by Lck. Second, native E2 protein expressed in Jurkat cells was phosphorylated following TCR engagement yet E2 with an Y613A mutation was not. Third, an Lck inhibitor rescued the HCV E2 protein-mediated effect on NFAT translocation following P+I activation, and finally, mutation of Y613 to alanine or phenylalanine restored distal TCR signaling. Phosphorylated HCV E2 inhibited distal TCR signaling by reducing NFAT nuclear translocation. NFAT nuclear import and export is regulated by large number of cellular proteins and non-coding RNAs (Sharma et al., 2011). Phospho-E2 may interfere with any of these factors, or combinations of factors, resulting in impaired NFAT nuclear translocation.

Figure 9:
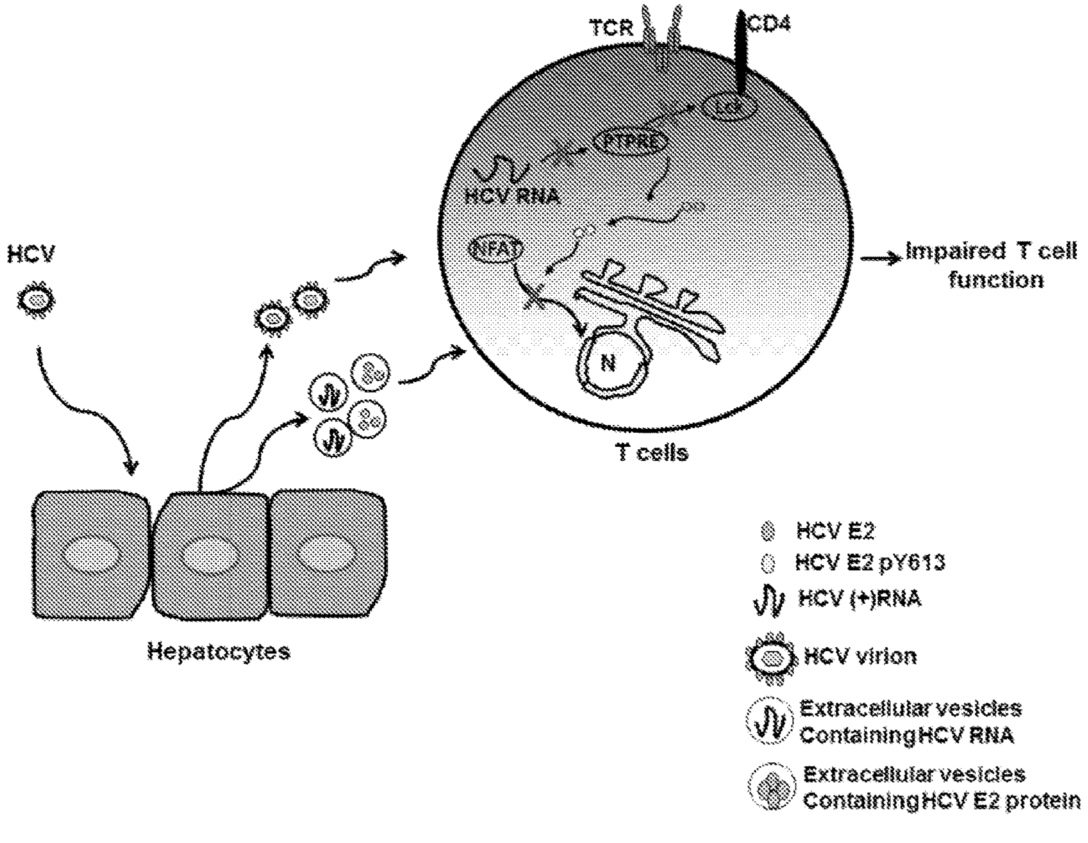
FIG. 9. Proposed model for inhibition of T cell receptor (TCR) signaling during HCV infection. HCV infection of hepatocytes results in the release of progeny HCV virions and extracellular vesicles containing HCV RNA and/or E2 protein. Viral RNA and/or E2 protein is released into T cells during particle interactions. HCV envelope RNA is processed into small RNA that inhibits protein tyrosine phosphatase E (PTPRE) expression, which results into impaired Lck activation following TCR engagement and defect in proximal TCR signaling. HCV E2 protein competes for Lck-mediated phosphorylation and phosphorylated HCV E2 at Y613 inhibits NFAT nuclear translocation, inhibiting distal TCR signaling. Inhibition of proximal and distal TCR signaling by HCV E2 RNA and protein contributes to impaired T cell function during HCV infection.

Together, the results indicate that HCV E2 Y613 served as an Lck substrate, and that Lck-mediated phosphorylation of Y613 was required for distal TCR signaling inhibition. Although, the amount of viral RNA and E2 protein transferred to the target T cells is unlikely to be comparable to that in the Jurkat cells expressing E2, significant inhibition of T cell activation was measured in cells incubated with serum, EVs or viral particles (HCVccs and HCVpps) following stimulation with a potent TCR agonist (CD3/CD28 antibodies). Thus the small amount of E2 protein and RNA present in serum and EVs is sufficient to reduce TCR activation. Although E1 could influence T cell activation inhibition, E2 protein was sufficient to inhibit distal TCR signaling, and mutation of the Y613 residue restored TCR signaling in the context of E2 protein expression (Y613A, Y613F) or HCV particles (HCVpp; Y613F). A model illustrating HCV particle interactions and the steps of E2 RNA and protein inhibition of TCR signaling is shown in FIG. 9. Furthermore, the observation that HCV E2 RNA and protein inhibit TCR-mediated activation at two distinct steps in the signaling cascade highlights the role of TCR during HCV infection. The RNA and amino acid sequences involved are highly conserved, thus TCR inhibition is synergistically inhibited in cells expressing both E2 RNA and protein.

During HCV infection, the concentration of serum HCV RNA-containing particles is high, frequently greater than one million copies of viral RNA per milliliter (Schijman et al., 2004 and Matthews-Greer, 2001). Thus there are abundant interactions between viral RNA-containing particles and lymphocytes. In addition to virions, HCV RNA is also present in extracellular vesicles (Ramakrishnaiah et al., 2013; Cosset and Dreux, 2014 and Dreux et al., 2012). Extracellular vesicles containing HCV, HPgV or hepatitis A virus RNA have been reported to deliver viral RNA into uninfected cells and initiate infection (Ramakrishnaiah et al., 2013; Cosset and Dreux, 2014; Chivero et al., 2014 and Feng et al., 2013). Although, in vitro effects of HCV sera on TCR appears to be potent and dose-dependent (FIG. 1C), the inhibitory effects of HCV RNA and protein are not complete in vivo because it is believed that the concentration of HCV RNA and protein in lymphocytes is low. Thus, the inhibitory effect of HCV particles does not appear to lead to severe immune deficiency. Nevertheless, there is evidence of general immune suppression during HCV infection. HCV infected subjects have blunted immune response against vaccine antigens like HBV and reduction in organ transplant rejection (Rehermann, 2013; Corell et al., 1995; Moorman et al., 2011 and Shi et al., 2014). The reduction in T cell activation and IL-2 release mediated by HCV particles may contribute to impaired T cell proliferation, differentiation and effector function observed ies (Rios-Olivares et al., 2006 and Folgori et al., 2006), which may aid in the establishment of acute infection and help maintain viral persistence in chronic infection. Furthermore, efficient T cell activation is involved in the generation of an effective immune response against pathogens, including vaccine antigens. Mutation of TCR inhibitory motifs within HCV E2 RNA and protein may lead to the design of improved envelope-based HCV vaccines.

All of the compositions and methods disclosed and claimed herein can be made and executed without undue experimentation in light of the present disclosure. While the compositions and methods of this disclosure have been described in terms of various embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 4,879,236
U.S. Pat. No. 5,440,013
U.S. Pat. No. 5,446,128
U.S. Pat. No. 5,475,085
U.S. Pat. No. 5,618,914
U.S. Pat. No. 5,650,298
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,925,565
U.S. Pat. No. 5,928,906
U.S. Pat. No. 5,929,237
U.S. Pat. No. 5,935,819
U.S. Pat. No. 6,261,569
Agnello et al., *Proc. Nat'l Acad. Sci. USA* 96(22):12766-71, 1999.
Ahmed et al., *BMC Bioinformatics* 14 Suppl 14:S9, 2013.
Almendro, et al., *J Immunol.,* 157(12):5411-21, 1996.
Ausubel et al., *Current Protocols in Molecular Biology*, Greene Publishing Associates and Wiley Interscience, N.Y., 1994.
Baichwal and Sugden, In: *Gene Transfer*, Kucherlapati (Ed.), NY, Plenum Press, 117-148, 1986.
Bartenschlager and Lohmann, 81(7):1631-48, 2000.
Berzsenyi et al., *J Hepatol* 55, 536-544, 2011.
Bhattarai and Stapleton *Trends Microbiol* 20, 124-130, 2012.
Bhattarai et al., *J Immunol* 190, 6351-6359, 2013.
Bhattarai et al., *J Immunol.,* 189: 2211-2216, 2013.
Bhattarai et al., *J Immunol.,* 189:2211-2216, 2012a.
Bhattarai et al., *J Infect Dis* 206, 1469-1472, 2012.
Bowen and Walker, *Nature* 436, 946-952, 2005.
Bradley et al., *J. Med. Virol.* 34(3):206-208, 1991.
Bukong et al., *PLoS Pathog* 10:e1004424, 2014.
Carbonelli et al., *FEMS Microbiol. Lett.,* 177(1):75-82, 1999.
Cerny and Chisari, *Hepatology* 30:595-601, 1999.
Chandler et al., *Proc Natl. Acad. Sci. USA,* 94(8):3569-601, 1997.
Chen and Okayama, *Mol. Cell Biol.,* 7:2745-2752, 1987.
Chen et al., *Gastroenterology* 116, 135-143, 1999.
Chivero et al., *J Gen Virol* 95:1307-1319, 2014.
Cocea, *Biotechniques,* 23(5):814-6, 1997.
Corell et al., *Lancet* 346:1497-1498, 1995.
Cosset and Dreux, *J Hepatol* 60:674-675, 2014.
Cox et al., C. *Hepatology* 42, 104-112, 2005.
Davis and van der Merwe, *Trends Immunol* 32:1-5, 2011.
Deeks et al., *Blood,* 104:942-947, 2004.
Doganiuc et al., *Alchohol Clin. Exp. Res.* 27:1023-1031, 2003.
Dreux et al., *Cell Host Microbe* 12:558-570, 2012.
Eckels, et al., *Hum. Immunol.* 60:187-199, 1999.
Fabbri et al., *Proc Natl Acad Sci USA* 109:E2110-2116, 2012.
Farci et al., *Proc. Natl. Acad. Sci. USA* 93:15394-15399, 1996.
Fechheimer et al., *Proc. Nat'l Acad. Sci. USA,* 84:8463-8467, 1987.
Feng et al., *Nature* 496:367-371, 2013.
Flint and Keating, *Rev. Med. Virol.* 10(2):101-117, 2000.
Flint et al., *J. Virol.* 73(8):6235-44, 1999.
Flint et al., *J. Virol.* 73(8):6782-90, 1999.
Folgori et al., *Gut* 55: 1012-1019, 2006.
Fornasieri et al., *Clin Exp Immunol* 122, 400-403, 2000
Fournillier et al., *J. Virol.* 75:12088-12097, 2001.
Fraley et al., *Proc. Natl. Acad. Sci. USA,* 76:3348-3352, 1979.
Freeman et al., *J Hepatol* 38, 349-356, 2003.
George et al., *J. Infect. Dis.,* 193:451-454, 2006.
Ghosh and Bachhawat, In: *Liver diseases, targeted diagnosis and therapy using specific receptors and ligands*, (Wu G, Wu C ed.), NY, Marcel Dekker, 87-104, 1991.
Gil-Henn and Elson, *J Biol Chem* 278:15579-15586, 2003.
Gopal, *Mol. Cell Biol.,* 5:1188-1190, 1985.
Graham and Van Der Eb, *Virology,* 52:456-467, 1973.

Grakoui et al., *Science* 302, 659-662, 2003.
Granot-Attas et al., *Src. Mol Biol Cell* 20:4324-4334, 2009.
Greene et al., *Immunology Today,* 10:272, 1989 Grossman, et al., *Nat Med,* 12:289-295, 2006.
Gruener et al., *J Virol* 75, 5550-5558, 2001.
Hadlock et al., *J. Virol.* 74(22):10407-16, 2000.
Hahn, *Curr. Opin. Immunol.* 15:443-449, 2003.
Harland and Weintraub, *J. Cell Biol.,* 101:1094-1099, 1985.
Hazenberg et al., *AIDS,* 17:1881-1888, 2003.
Hijikata et al., *J. Virol.* 67(4):1953-58, 1993.
Hunt et al., *J Infect Dis,* 187:1534-1543, 2003.
Hunt et al., *J Infect Dis,* 197:126-133, 2008.
Jang et al., *Proc Natl Acad Sci USA* 107:10620-10625, 2010.
Kaneda et al., *Science,* 243:375-378, 1989.
Kanto, et al., *J. Immunol.* 162:5584-5591, 1999.
Kobayashi et al., *J. Gastroenterol.* 33:500-507, 1998.
Kraus et al., *FEBS Lett.,* 428(3):165-70, 1998.
Krishnada, et al., *Int. Immunol.* 22:491-502, 2010.
Kuhl et al., *Cell,* 50:1057, 1987.
Lauer and Walker, *N. Engl. J. Med.* 345:41-52, 2001.
Lauer et al., *Gastroenterology* 127, 924-936, 2004.
Lavanchy, *Liver Int,* 29 Suppl 1, 74-81, 2009.
Lee et al., *DNA Cell Biol.,* 16(11):1267-1275, 1997.
Levenson et al., *Hum. Gene Ther.,* 9(8):1233-6, 1998.
Lewis et al., *Cell* 120:15-20, 2005.
Li and Lemon, *Semin Immunopathol* 35, 53-72, 2013.
Liang, *Nat Med* 19, 869-878, 2013.
Lindenbach et al., *Science* 309:623-626, 2005.
Lohmann et al., *Science* 285:110-113, 1999.
Maidana-Giret et al., *AIDS,* 23:2277-2287, 2009.
Major and Feinstone, Hepatology 25(6):1527-38, 1997.
Masciopinto et al., *Eur J Immunol,* 34:2834-2842, 2004.
Matthews-Greer et al., *Clin Diagn Lab Immunol* 8:690-694, 2001.
Medzhitov and Janeway, *Semin Immunol* 10, 351-353, 2008.
Mohr et al., 15th International Symposium on Hepatitis C and Related Viruses, San Antonio, Tex. 2008.
Mohr et al., *J. Immunol.,* 185:4496-4505, 2010.
Monazahian et al., *J. Med. Virol.* 57(3):223-229, 1999.
Monazahian et al., *J. Med. Virol.* 57(3):223-9, 1999.
Moorman et al., *Vaccine* 29:3169-3176, 2011.
Nattermann et al., *AIDS,* 17:1457-1462, 2003.
Nelson et al., *J Viral Hepat* 4:29-35, 1997.
Netski et al., *Clin Infect Dis* 41, 667-675, 2005.
Ng et al., *Nuc. Acids Res.,* 17:601, 1989.
Nicolas and Rubenstein, In: *Vectors: A survey of molecular cloning vectors and their uses*, Rodriguez and Denhardt (eds.), Stoneham: Butterworth, 493-513, 1988.
Nicolau and Sene, *Biochim. Biophys. Acta,* 721:185-190, 1982.
Nomoto et al., *Gene,* 236(2):259-271, 1999.
Owsianka et al., *J. Gen. Virol.* 82(8)1877-83, 2001.
Parameswaran et al., *PLoS Pathog* 6:e1000764, 2010.
Park et al., *Nat Med* 19, 1638-1642, 2013.
Patel et al., *J. Gen. Virol.* 81(12):2873-83, 2000.
Petracca et al., *J. Virol.* 74(10):4824-30, 2000.
Pileri et al., *Science* 282(5390):938-941, 1998.
Potter et al., *Proc. Nat'l Acad. Sci. USA,* 81:7161-7165, 1984.
Prince et al., *J. Viral. Hepat.* 3(1):11-17, 1996.
Quinkert et al., *J Virol* 79: 13594-13605, 2005.
Radziewicz et al., *Gastroenterology* 134, 2168-2171, 2008.
Ramakrishnaiah et al., *Proc Natl Acad Sci USA* 110:13109-13113, 2013.
Randall et al., *Proc Natl Acad Sci USA* 104:12884-12889, 2007.
Rehermann *Semin Liver Dis* 27, 152-160, 2007.
Rehermann, *J Clin Invest* 119:1745-1754, 2009.
Rehermann, *Nat Med* 19:859-868, 2013.
Reiser et al., *J Hepatol* 26:471-478, 1997.
Remington's Pharmaceutical Sciences, 15th Ed., 33:624-652, 1990.
Remington's Pharmaceutical Sciences, 18th Ed. Mack Printing Company, 1389-1404, 1990,
Ridgeway, In: *Vectors: A survey of molecular cloning vectors and their uses*, Rodriguez and Denhardt (Eds.), Stoneham:Butterworth, 467-492, 1988.
Rios-Olivares et al., *Drug Alcohol Depend* 85:236-243, 2006.
Rippe et al., *Mol. Cell Biol.,* 10:689-695, 1990.
Roskoski, *Biochem Biophys Res Commun* 331:1-14, 2005.
Rydze et al., *Antivir Ther* 17:1271-1279, 2012.
Schijman et al., *Clin Diagn Lab Immunol* 11:433-435, 2004.
Schmidt et al., *J Infect Dis* 176, 20-26, 1997.
Schmidt et al., *J. Infect. Dis.* 6(1):20-26, 1997.
Schwarze-Zander et al., *Antivir. Ther.,* 15:745-752, 2010.
Semmo et al., *Hepatol.* 41:1019-1028, 2005.
Serti et al., *Cell. Mol. Life Sci.* 68:505-522, 2011.
Sharma et al., *Proc Natl Acad Sci USA* 108:11381-11386, 2011.
Shi et al., *J Immunol* 192:649-657, 2014.
Shimakami et al., *Proc Natl Acad Sci USA* 109:941-946, 2012.
Shoukry et al, *J Exp Med* 197, 1645-1655, 2003.
Soderholm and Sallberg, *J Infect Dis* 194, 1724-1728, 2006.
Spangenberg et al., *Hepatology* 42, 828-837, 2005.
Stapleton et al., *AIDS* 23:605-610, 2009.
Stapleton et al., In *6th International AIDS Society Conference on HIV Pathogenesis, Treatment and Prevention*. Rome, Italy., 2011.
Stapleton et al., *J. Gen. Virol.,* 92:233-246, 2011.
Stapleton et al., *PLoS One* 7:e50563, 2012.
Supekova et al., *J Biol Chem* 283:29-36, 2008.
Temin, In: *Gene Transfer*, Kucherlapati (ed.), NY: Plenum Press, 149-188, 1986.
Terilli and Cox *Curr HIV/AIDS Rep* 10, 51-58, 2013.
Thimme et al., *Proc Natl Acad Sci USA* 99, 15661-15668, 2002.
Thimme et al., *J Exp Med* 194, 1395-1406, 2001.
Thomssen et al., *Med. Microbiol. Immunol.* 181(5):293-300, 1992.
Thomssen et al., *Med. Microbiol. Immunol.* 182(6):329-334, 1993.
Toledano-Katchalski and Elson, *Oncogene* 18: 5024-5031, 1999.
Tomova, et al., *Anticancer Res.* 29:5241-5244, 2009.
Tu et al., *Cell Immunol* 284, 98-103, 2013.
Tur-Kaspa et al., *Mol. Cell Biol.,* 6:716-718, 1986.
Urbani et al., *J Hepatol* 48, 548-558, 2008.
Vinikoor et al., *J Acquir Immune Defic Syndr,* 2013
Wang et al., *J Infect Dis* 166, 1167-1169, 1992.
Wang et al., *Vaccine* 31, 2238-2245, 2013.
Wedemeyer et al., *J Immunol* 169, 3447-3458, 2002.
Williams et al., *N. Engl. J. Med.,* 350:981-990, 2004.
Wu and Wu, *Biochem.,* 27:887-892, 1988.
Wu and Wu, *J. Biol. Chem.,* 262:4429-4432, 1987.
Wu et al., *Biochem. Biophys. Res. Commun.,* 233(1):221-6, 1997.
Wu et al., *J. Med. Virol.,* 52:83-85. 1997.
Wunschmann et al., *J. Virol.* 74(21):10055-62, 2000.
Xiang et al., *J Virol* 72:2738-2744, 1998.
Xiang et al., *J. Immunol.* 183:7860-9, 2009.
Xiang et al., *J. Viral Hepat.,* 6:S16-S22, 1999.
Xiang et al., *J. Virol.* 72(4):2738-44, 1998.

Xiang et al., *J. Virol.* 74:9125-9133, 2000.
Xiang et al., *N. Engl. J. Med.*, 345:707-714, 2001.
Xiang et al., *PLoS One* 3: e2580, 1-10, 2008.
Xiang et al., *Proc. Natl. Acad. Sci USA*, 103:15570-15575, 2006.
Xiang et al., *Virology* 430:53-62, 2012.
Xue et al., *Mol Cell Proteomics* 7:1598-1608, 2008.
Xue et al., *Protein Eng. Des. Sel.* 24:255-60, 2011.
Yang et al., *Proc. Natl. Acad. Sci USA*, 87:9568-9572, 1990.
Zignego et al., *Dig Liver Dis* 39 Suppl 1, S38-45, 2007.

What is claimed is:

1. A method of inhibiting immune cell activation comprising administering to a mammalian subject in need thereof a viral RNA segment comprising a nucleic acid encoding a T cell immune-inhibitory domain selected from the group consisting of HCV E2 sequences, YFV envelope, and HIV gp41 sequences, wherein said nucleic acid inhibits said immune cell activation.

2. The method of claim 1, wherein said nucleic acid comprises about 16, 17, 18, 19, 20, 21, 22, 23, 24, 25, 27, 30, 35, 40, 45, 50, 51, 75, 100, 150, 175, 200, 225, 250, 300, 400 or 500 consecutive bases of the T cell immune-inhibitory domain.

3. The method of claim 1, wherein the nucleic acid encodes HCV E2 sequences.

4. The method of claim 3, wherein the viral RNA segment further encodes non-HCV E2 sequences, non-GBV-C E2 sequences, non-YFV envelope sequences or non-HIV gp41 sequences.

5. The method of claim 1, wherein the immune cell is a T cell.

6. The method of claim 1, wherein said subject is a non-human mammal.

7. The method of claim 1, wherein said subject is a human.

8. The method of claim 1, wherein administering comprises intravenous, intra-arterial, oral, subcutaneous, topical or intraperitoneal administration.

9. The method of claim 1, further comprising administering a second anti-inflammatory agent.

10. The method of claim 1, wherein said viral RNA segment is provided in combination with a gene therapy vector.

11. The method of claim 1, further comprising administering a gene therapy vector.

12. The method of claim 10, wherein said gene therapy vector comprises a viral gene therapy vector.

13. The method of claim 1, wherein said viral RNA segment comprises at least one non-natural base.

14. The method of claim 1, wherein said viral RNA segment comprises a Dicer substrate.

15. The method of claim 1, wherein said nucleic acid is administered at 0.1-500 mg/kg/d.

16. The method of claim 1, wherein said nucleic acid is administered daily or weekly.

17. The method of claim 1, wherein said nucleic acid is derived from Human Immunodeficiency Virus envelope gp120/160, Yellow Fever Virus envelope protein, Bovine Viral Diarrhea Virus envelope protein, Classical Swine Fever Virus envelope protein, influenza envelope protein, Dengue Virus envelope protein, West Nile Virus envelope protein, and Japanese Encephalitis Virus envelope protein.

18. A method of performing gene transfer into a subject comprising administering to said subject:

a) an expression cassette comprising a heterologous gene segment under the control of a promoter operable in cells of said subject and b) a viral RNA segment comprising a nucleic acid sequence encoding a T cell immune-inhibitory domain selected from the group consisting of HCV E2 sequences, YFV envelope, and HIV gp41 sequences, wherein said nucleic acid inhibits immune cell activation.

19. A pharmaceutical composition comprising a nucleic acid having the sequence:

(SEQ ID NO: 3)
CTCACGCCAAGGTGCCTGATCGACTACCCCTACAGGCTCTGGCATTATCC;

(SEQ ID NO: 4)
CTCACGCCAAGGTGCCTGATCGACTACCCCTACAGGCTCTGGCATTAC-CCC;
or (SEQ ID NO: 5)
GACAACAACCTTTACAAACTACATGGT.

or comprising a nucleic acid sequence selected from GCATTATCC (SEQ ID NO: 38), GCAUUAUCC (SEQ ID NO: 39), GCATTACCCC (SEQ ID NO: 40), GCAUUACCCC (SEQ ID NO: 41), CUUUACAAAA (SEQ ID NO: 42), or CTTTACAAA (SEQ ID NO: 43), wherein said nucleic acid consists essentially of at least about 20 base pairs and no more than about 55 base pairs.

20. The method of claim 5, wherein said T cell is a helper T cell, suppressor T cell, or a killer T cell.

* * * * *